US007704686B2

(12) United States Patent
Morimoto et al.

(10) Patent No.: US 7,704,686 B2
(45) Date of Patent: Apr. 27, 2010

(54) METHODS OF IDENTIFYING IMMUNOREGULATORY AGENTS, IMMUNOREGULATORY AGENTS, AND USES THEREOF

(75) Inventors: Chikao Morimoto, Tokyo (JP); Kei Ohnuma, Tokyo (JP)

(73) Assignee: Toudai TLO, Ltd., Tokyo (JP)

( * ) Notice: Subject to any disclaimer, the term of this patent is extended or adjusted under 35 U.S.C. 154(b) by 162 days.

(21) Appl. No.: 10/584,837

(22) PCT Filed: Dec. 28, 2004

(86) PCT No.: PCT/JP2004/019846

§ 371 (c)(1),
(2), (4) Date: Feb. 13, 2007

(87) PCT Pub. No.: WO2005/063170

PCT Pub. Date: Jul. 14, 2005

(65) Prior Publication Data

US 2007/0259824 A1 Nov. 8, 2007

Related U.S. Application Data

(60) Provisional application No. 60/532,723, filed on Dec. 29, 2003.

(51) Int. Cl.
*A61K 48/00* (2006.01)
(52) U.S. Cl. .............................. 435/6; 435/325; 435/375
(58) Field of Classification Search ........................ None
See application file for complete search history.

(56) References Cited

U.S. PATENT DOCUMENTS 6,017,729 A    1/2000  Anderson et al.
7,205,409 B2 *  4/2007  Pei et al. ..................... 546/153

OTHER PUBLICATIONS

Williams et al. Dipeptidyl peptidase IV on activated T cells as a target molecule for therapy of rheumatoid arthritis (Clin Exp Immunol 2003, vol. 131: 68-74).*
Meester et al. CD26, let it cut or cut it down. Immunology Today, 1999, vol. 20: 367-375.*
BIOSIS, Accession No. PREV199192004874, Biosis abstract for Valle, A. et al., *Int. Immunol.* 3:229-236, Oxford University Press (1991).
BIOSIS, Accession No. PREV199799590112, Biosis abstract for Blazquez, M.V. et al., *Protoplasma 197*:26-33, Springer-Verlag Wien (1997).
BIOSIS, Accession No. PREV200300053191, Biosis abstract for Bozinovski, S. et al., *J. Biol. Chem.* 277:42808-42814, The American Society for Biochemistry and Molecular Biology, Inc. (Nov. 2002).
Bosisio, D. et al., "Stimulation of toll-like receptor 4 expression in human mononuclear phagocytes by interfon-γ: a molecular basis for priming and synergism with bacterial lipopolysaccharide," *Blood* 99:3427-3431, The American Society of Hematology (May 2002).

Burns, K. et al., "Inhibition of Interleukin 1 Receptor/Toll-like Receptor Signaling through the Alternatively Spliced, Short Form of MyD88 Is Due to Its Failure to Recruit IRAK-4," *J. Exp. Med.* 197:263-268, The Rockefeller University Press (2003).
Cao, Z. et al., "IRAK: A Kinase Associated with the Interleukin-1 Receptor," *Sci. 271*:1128-1131, American Association for the Advancement of Science (1996).
Cooke, E.-L. et al., "Functional analysis of the interleukiin-1 -receptor-associated kinase (IRAK-1) in interleukin-1β-stimulated nuclear factor κb (NF-κB) pathway activation: IRAK-1 associates with the NF-κB essential modulator (NEMO) upon receptor stimulation," *Biochem. J. 359*:403-410, Portland Press on behalf of the Biochemical Society (2001).
Hegen, M. et al., "Cross-linking of CD26 by antibody induces tryosine phosphorylation and activation of mitogen-activated protein kinase," *Immunol. 90*:257-264, Blackwell Scientific Publications, Inc. (1997).
MEDLINE Accession No. NLM11960013, Medline abstract for Li, S. et al., *Proc. Nat'l Acad. Sci. USA 99*:5567-5572, National Academy of Sciences (Apr. 2002).
Burns, K., et al., "Tollip, a new component of the IL-1RI pathway, links IRAK to the IL-1 receptor," *Nat. Cell Biol.* 2:346-351, Nature Publishing Group (2000).
Cho, K.A., et al., "Senescent Phenotype Can Be Reversed by Reduction of Caveolin Status," *J. Biol. Chem. 278*:27789-27795, American Society for Biochemistry and Molecular Biology (Jul. 2003).
Christopherson, K.W., et al., "Suppression or Deletion of CD26 (DPPIV) Activity on Donor Cells Greatly Enhances the Efficiency of Mouse Hematopoietic Stem & Progenitor Cell Homing and Engraftment In Vivo," *Blood 102*:38a, American Society of Hematology (Nov. 2003).
Elliott, M.H., et al., "Cholesterol-Dependent Association of Caveolin-1 with the Transducin α Subunit in Bovine Photoreceptor Rod Outer Segments: Disruption by Cyclodextrin and Guanosine 5'-0-(3-Thiotriphosphate)," *Biochemistry 42*:7892-7903, American Chemical Society (Jul. 2003).

(Continued)

*Primary Examiner*—Kimberly Chong
(74) *Attorney, Agent, or Firm*—Sterne, Kessler, Goldstein & Fox P.L.L.C.

(57) ABSTRACT

The present invention provides methods of identifying a substance that down-regulates or up-regulates an immune response and kits used for the identification methods. A method of this invention comprises detecting a substance that inhibits or enhances the interaction between CD26 and caveolin-1. Another method comprises detecting a substance that inhibits or enhances the interaction between caveolin-1 and Tollip. Still another method comprises detecting a substance that inhibits or enhances the interaction among caveolin-1, Tollip, and IRAK-1. The present invention also relates to immunoregulatory agents comprising a substance that down-regulates an immune response, such as siRNA against caveolin-1 or Tollip. The invention further provides immunoregulatory agents comprising a substance that up-regulates an immune response. These agents are useful for treating inflammatory diseases, autoimmune diseases, or other immune-mediated disorders.

9 Claims, 19 Drawing Sheets

OTHER PUBLICATIONS

Ho, L., et al., "In Vitro and in Vivo Antitumor Effect of the Anti-CD26 Monoclonal Antibody 1F7 on Human CD30+ Anaplastic Large Cell T-Cell Lymphoma Karpas 299," *Clin. Cancer Res. 7*:2031-2040, The American Association for Cancer Research (2001).

Ikushima, H., et al., "Internalization of CD26 by mannose 6-phosphate/insulin-like growth factor II receptor contributes to T cell activation," *Proc. Natl. Acad. Sci. USA 97*:8439-8444, National Academy of Sciences (2000).

Iwata, S., et al., "CD26/dipeptidyl peptidase IV differentially regulates the chemotaxis of T cells and monocytes toward RANTES: possible mechanism for the switch from innate to acquired immune response," *Int. Immunol. 11*:417-426, The Japanese Society for Immunology (1999).

Kameoka, J., et al., "Direct Association of Adenosine Deaminase with a T Cell Activation Antigen, CD26," *Science 261*:466-469, American Association for the Advancement of Science (1993).

Marella, M., et al., "Filipin Prevents Pathological Prion Protein Accumulation by Reducing Endocytosis and Inducing Cellular PrP Release," *J. Biol. Chem. 277*:25457-25464, American Society for Biochemistry and Molecular Biology (Jul. 2002).

Martin, M.U., et al., "Summary and comparison of the signaling mechanisms of the Toll/interleukin-1 receptor family," *Biochim. Biophys. Acta 1592*:265-280, Elsevier Science B.V. (Nov. 2002).

Mizokami, A., et al., "Increased Population of High Fluorescence 1F7 (CD26) Antigen on T cells in Synovial Fluid of Patients with Rheumatoid Arthritis," *J. Rheumatol. 23*:2022-2026, Journal of Rheumatology Publishing Company (1996).

Morimoto, C., et al., "1F7, A Novel Cell Surface Molecule, Involved in Helper Function of CD4 Cells," *J. Immunol. 143*:3430-3439, American Association of Immunologists (1989).

Morimoto, C., et al., "The structure and function of CD26 in the T-cell immune response," *Immunol. Rev. 161*:55-70, Munksgaard (1998).

Nomura, R., et al., "Tyrosine-phosphorylated Caveolin-1: Immunolocalization and Molecular Characterization," *Mol. Biol. Cell 10*:975-986, American Society for Cell Biology (1999).

Ohnuma, K., et al., "Soluble CD26/Dipeptidyl Peptidase IV Induces T cell Proliferation Through CD86 Up-Regulation on APCs," *J. Immunol. 167*:6745-6755, American Association of Immunologists (2001).

Ohnuma, K., et al., "CD26 up-regulates expression of CD86 on antigen-presenting cells by means of caveolin-1," *Proc. Natl. Acad. Sci. USA 101*:14186-14191, National Academy of Sciences (2004).

Soong, G., et al., "Selective recruitment of toll like receptor components mediates airway epithelial responses to bacteria," *FASEB J. 17*:A655, The Federation of American Societies for Experimental Biology, Abstract No. 405.5 (Apr. 2003).

Sunaga, N., et al., "RNAi-mediated knockdown of caveolin-1 and c-myc leads to growth inhibition of human tumor cells," *Proc. Am. Assoc. Cancer Res. 44*:192-193, American Association for Cancer Research (Jul. 2003).

Tanaka, T., et al., "Cloning and Functional Expression of the T Cell Activation Antigen CD26," *J. Immunol. 149*:481-486, The American Association of Immunologists (1992).

Tanaka, T., et al., "The costimulatory activity of the CD26 antigen requires dipeptidyl peptidase IV enzymatic activity," *Proc. Natl. Acad. Sci. USA 90*:4586-4590, National Academy of Sciences (1993).

Tanaka, T., et al., "Enhancement of antigen-induced T-cell proliferation by soluble CD26/dipeptidyl peptidase IV," *Proc. Natl. Acad. Sci. USA 91*:3082-3086, National Academy of Sciences (1994).

Torimoto, Y., et al., "Biochemical Characterization of CD26 (Dipeptidyl Peptidase IV): Functional Comparison of Distinct Epitopes Recognized by Various Anti-CD26 Monoclonal Antibodies," *Mol. Immunol. 29*:183-192, Pergamon Press (1992).

Trigatti, B.L., et al., "Identification of Caveolin-1 as a Fatty Acid Binding Protein," *Biochem. Biophys. Res. Commun. 255*:34-39, Academic Press (1999).

Volpe, F., et al., "The IL1 receptor accessory protein is responsible for the recruitment of the interleukin-1 receptor associated kinase to the IL1/IL1 receptor I complex," *FEBS Lett. 419*:41-44, Elsevier Science B.V. (1997).

PCT International Search Report for International Application No. PCT/JP2004/019846, European Patent Office, Netherlands, mailed on Aug. 3, 2005.

\* cited by examiner

Fig1
A
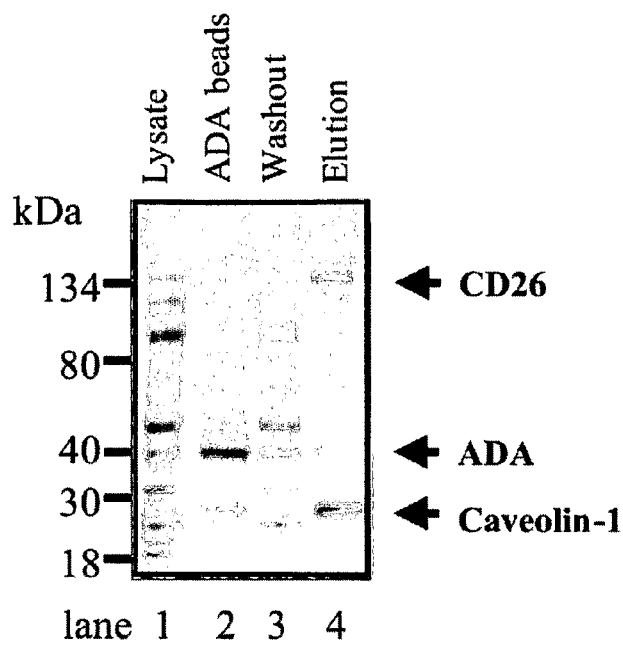
B
IP: Caveolin    IP: CD26
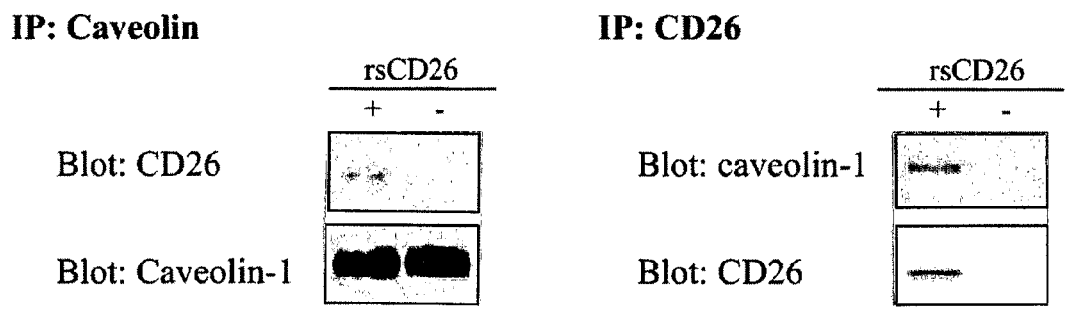
C
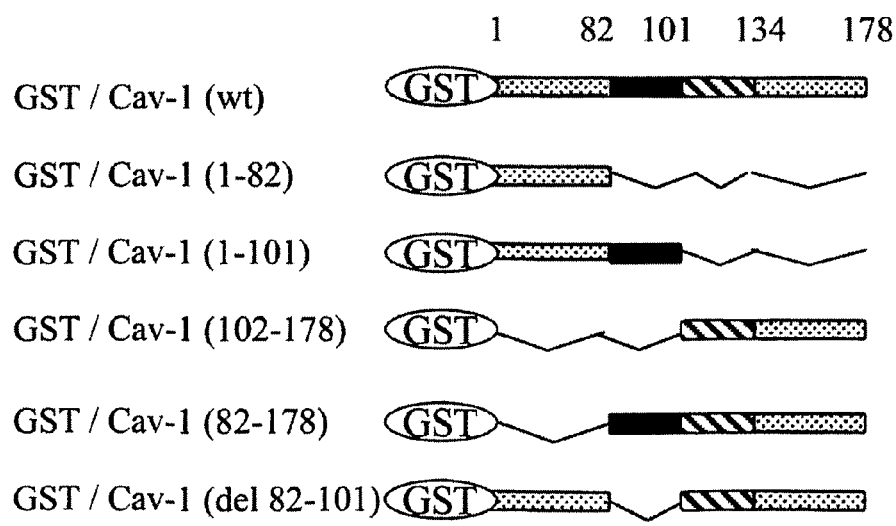

Fig1
D
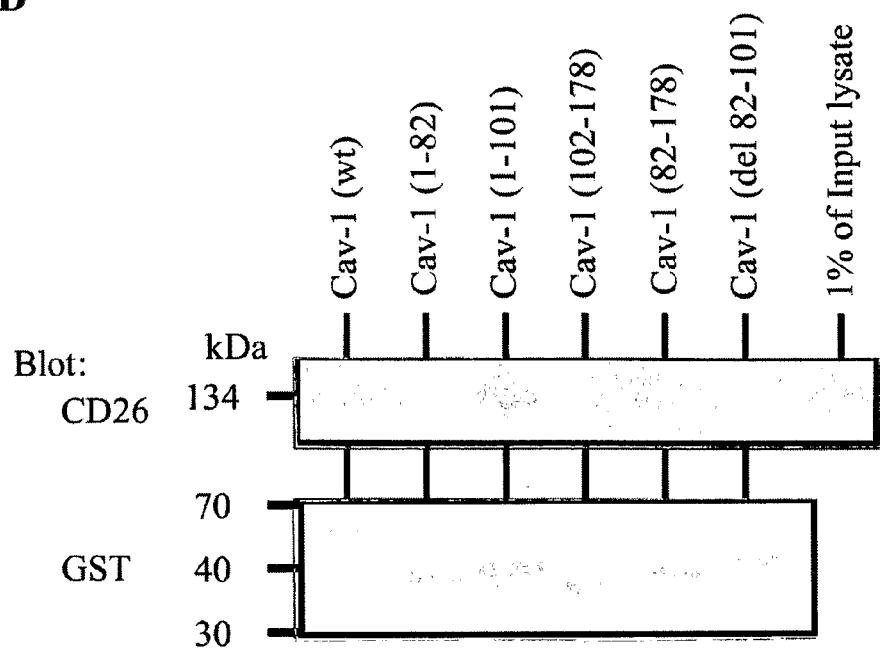
E
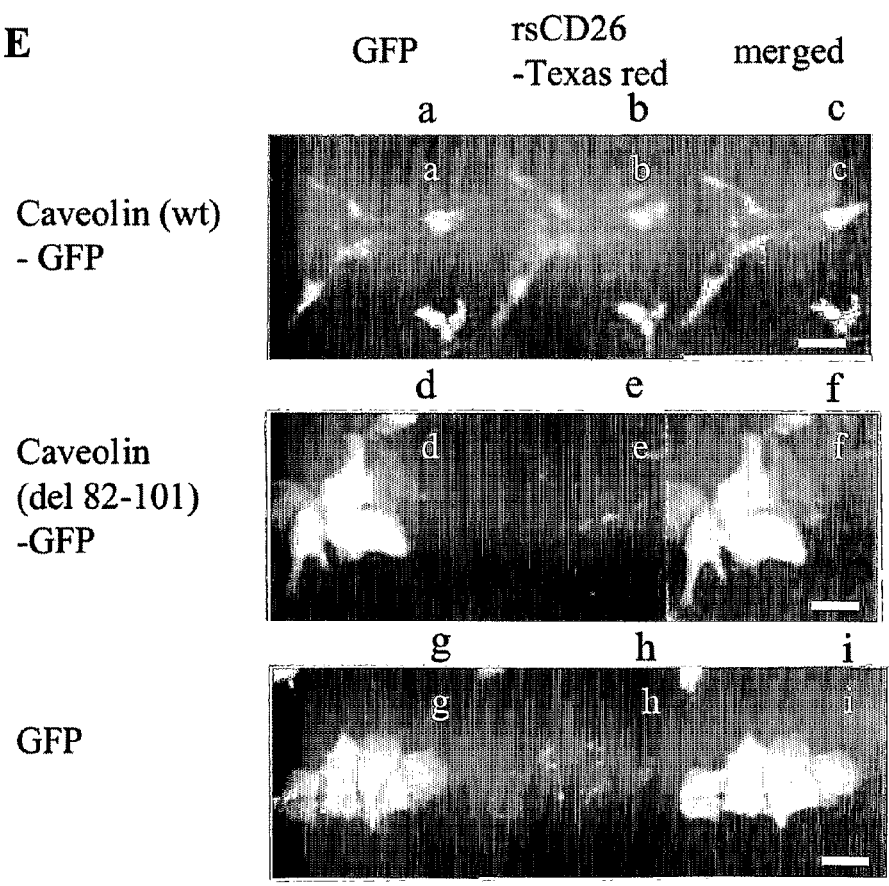

Fig1
F
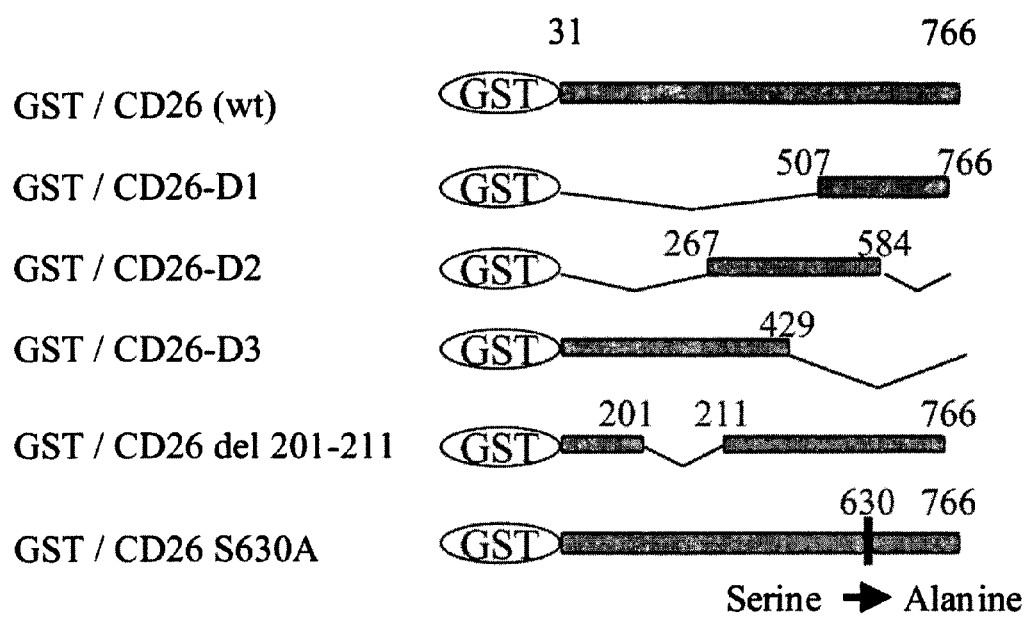
G
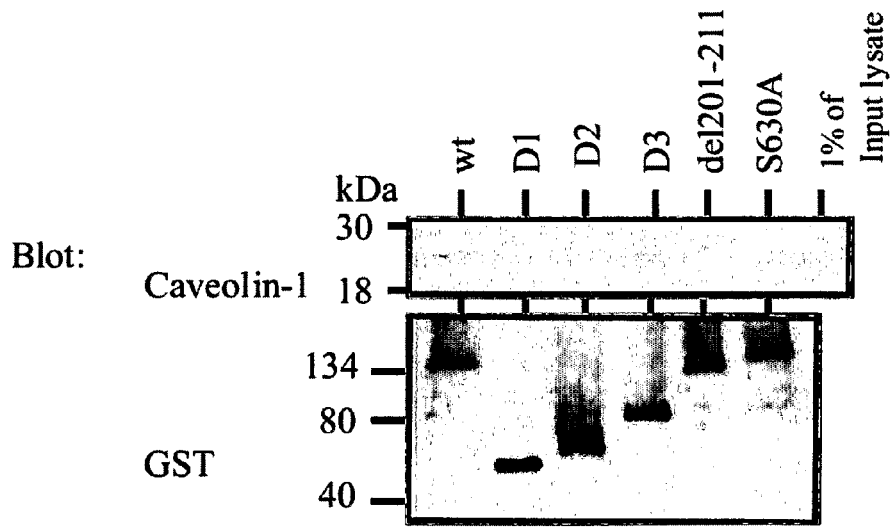

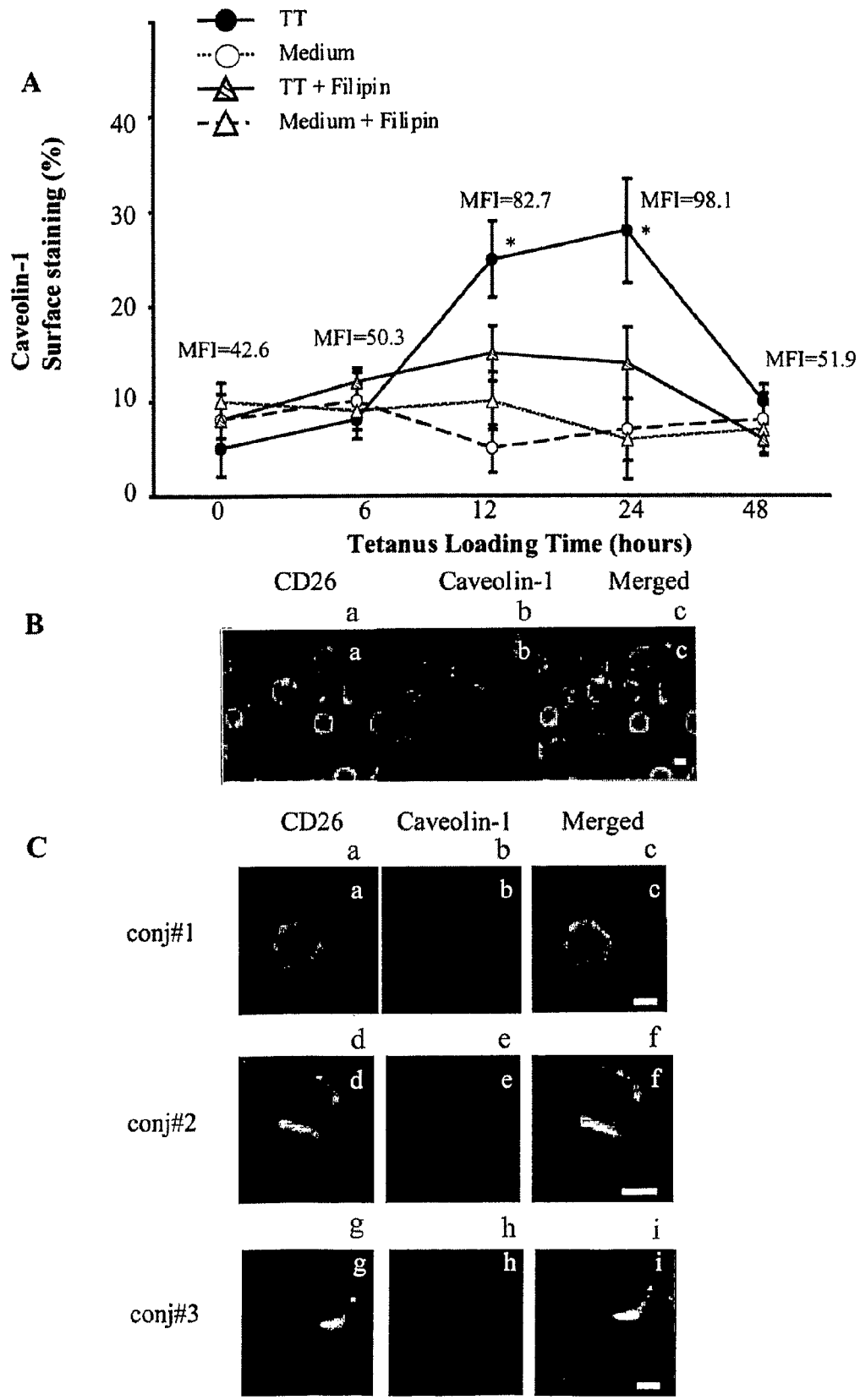

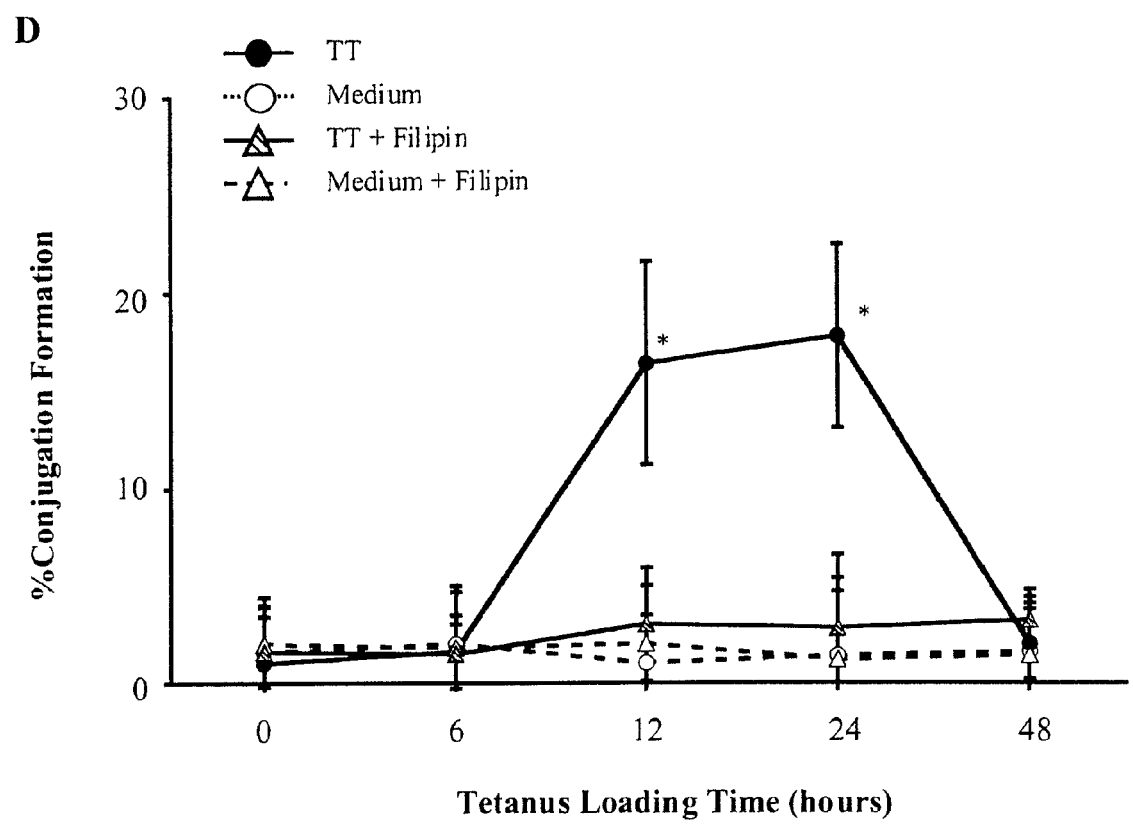

Fig3
A
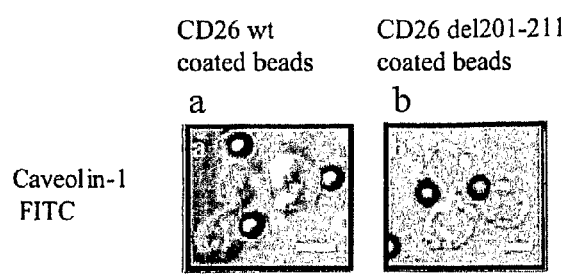
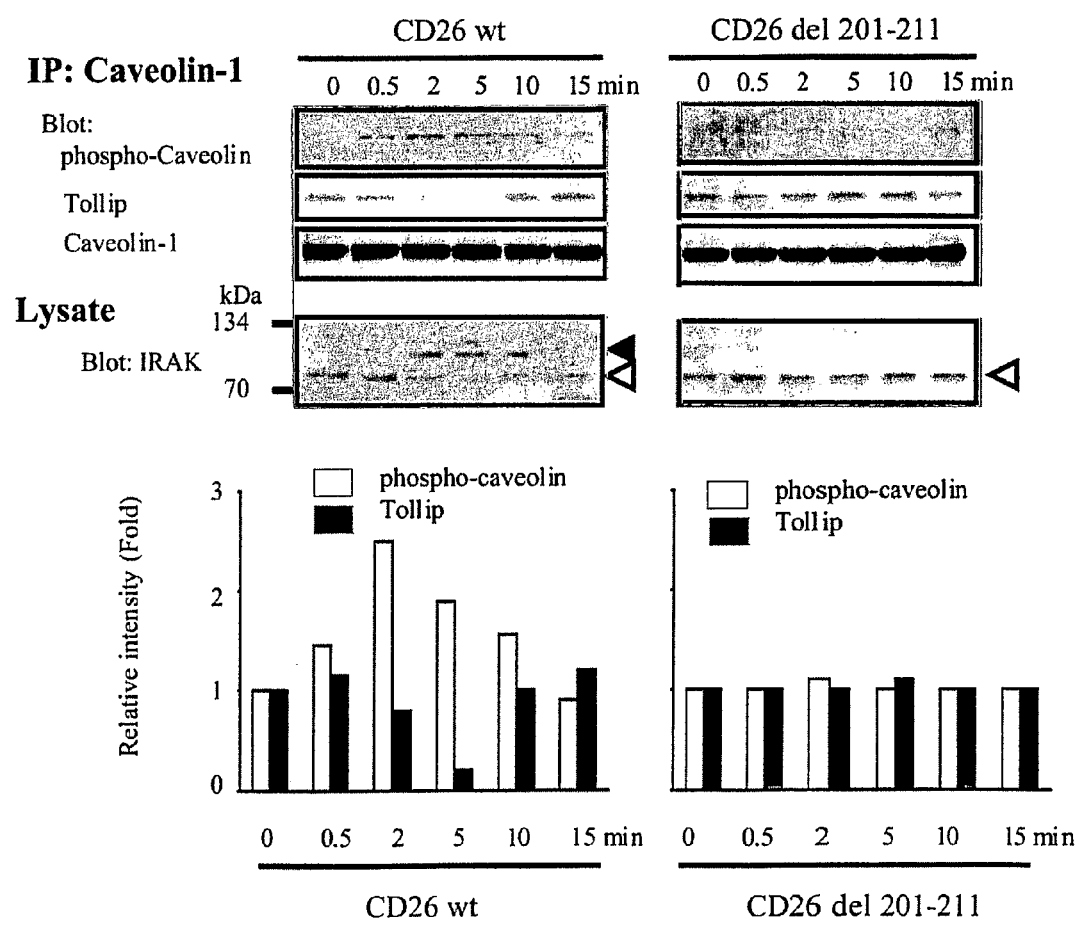

Fig3
D
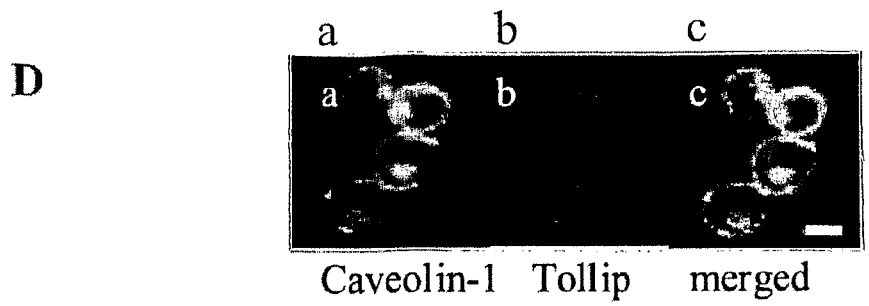
Caveolin-1   Tollip   merged
E  THP-1 cell lysate
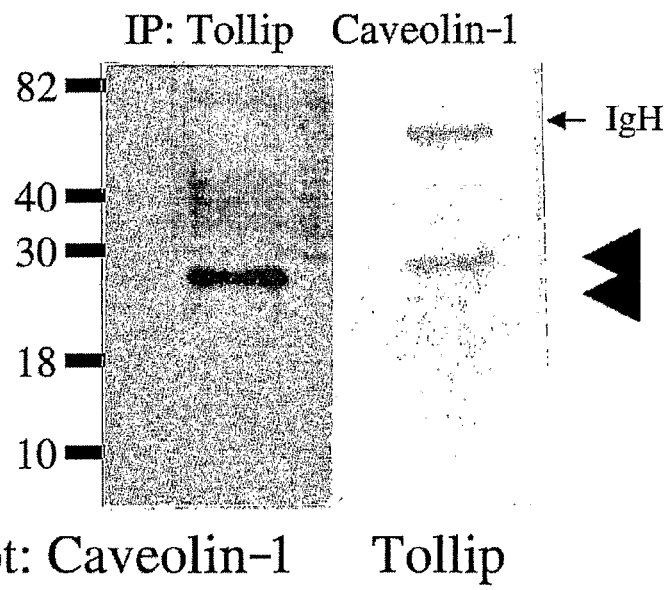
F
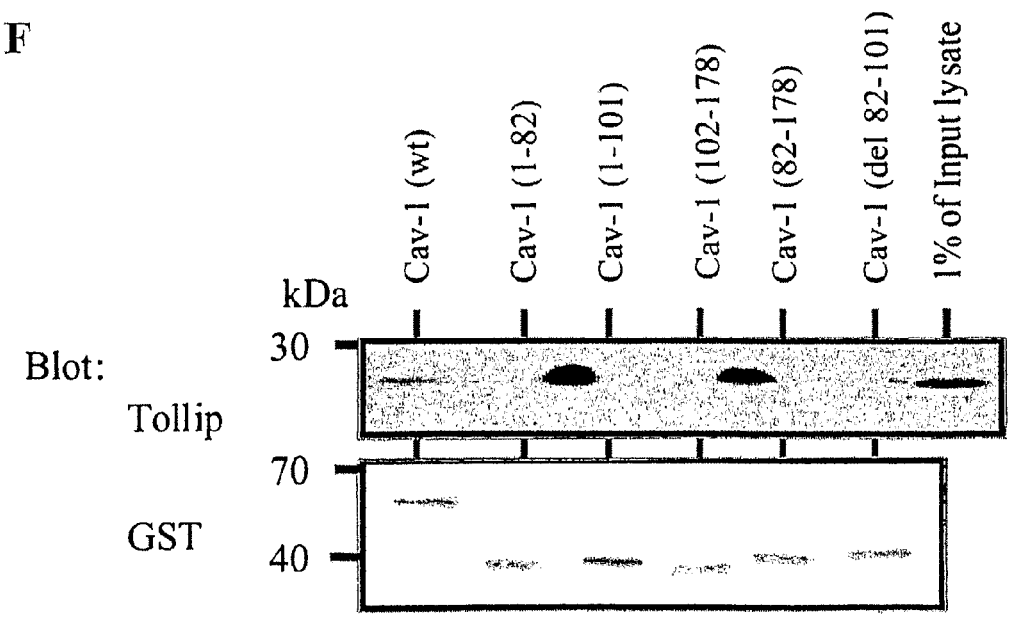

Fig3
G
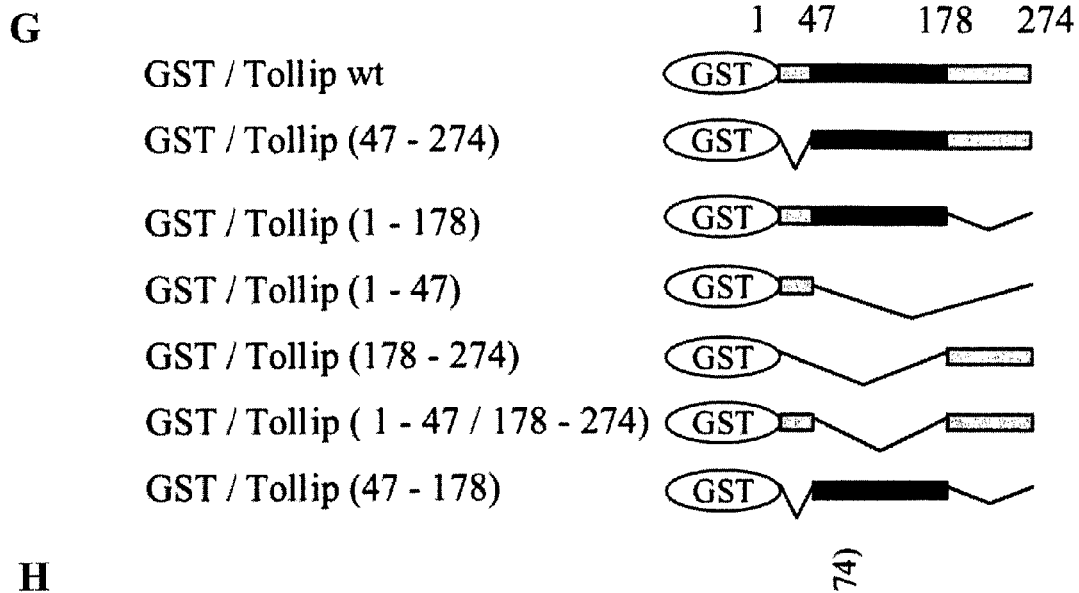
H
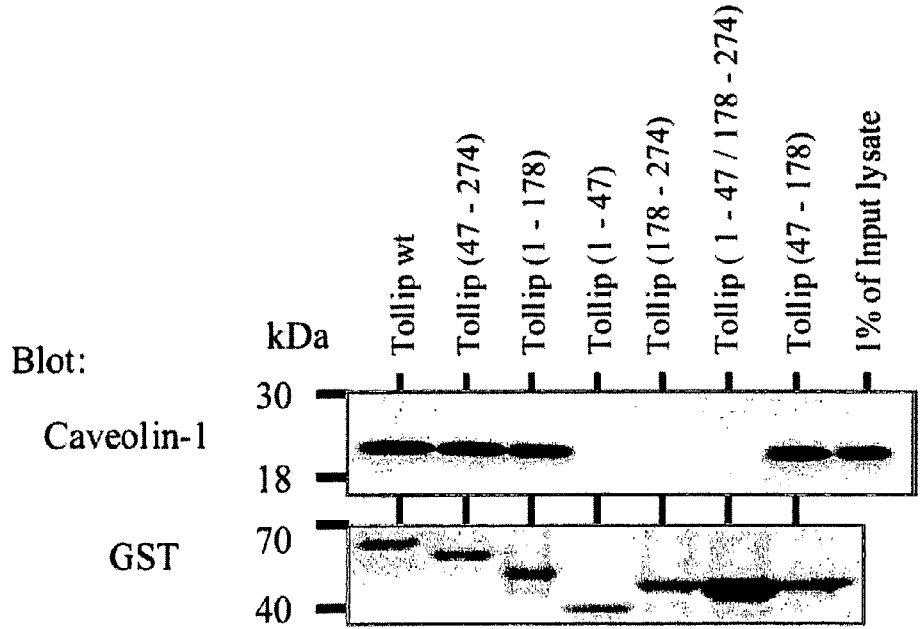

Fig 4
A
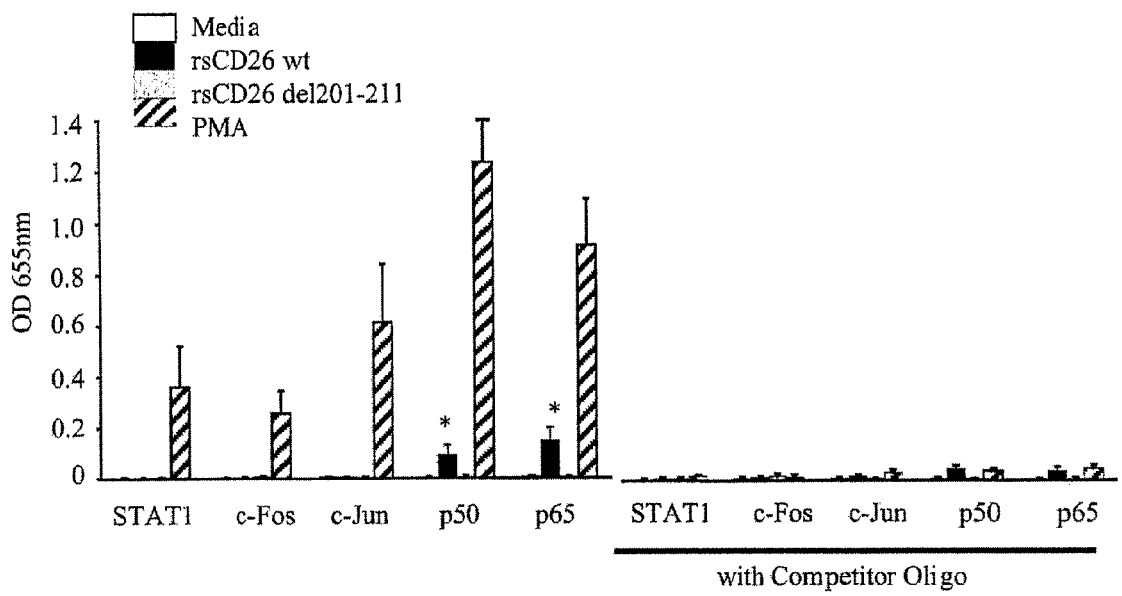
B
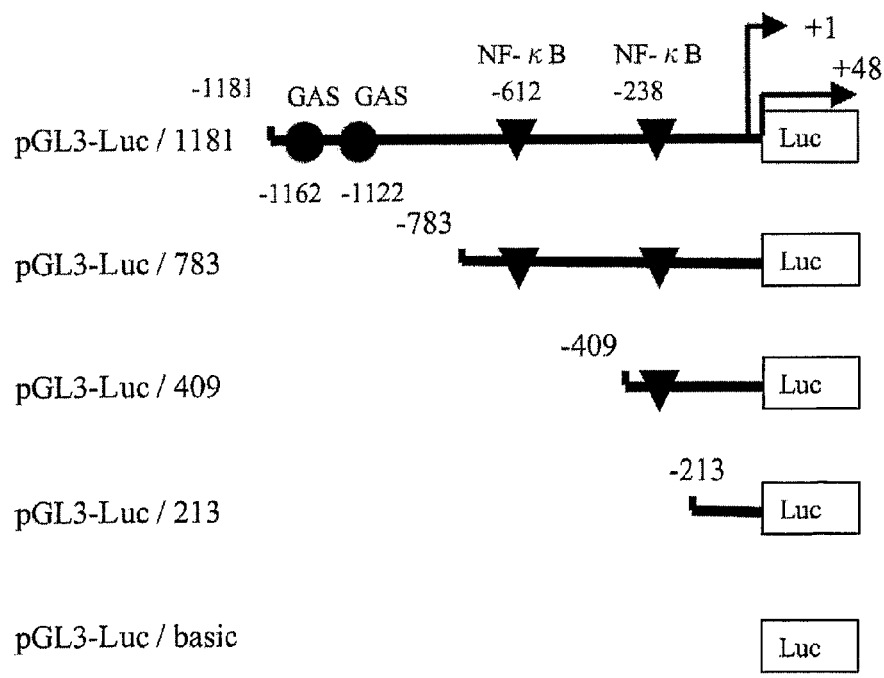

Fig4
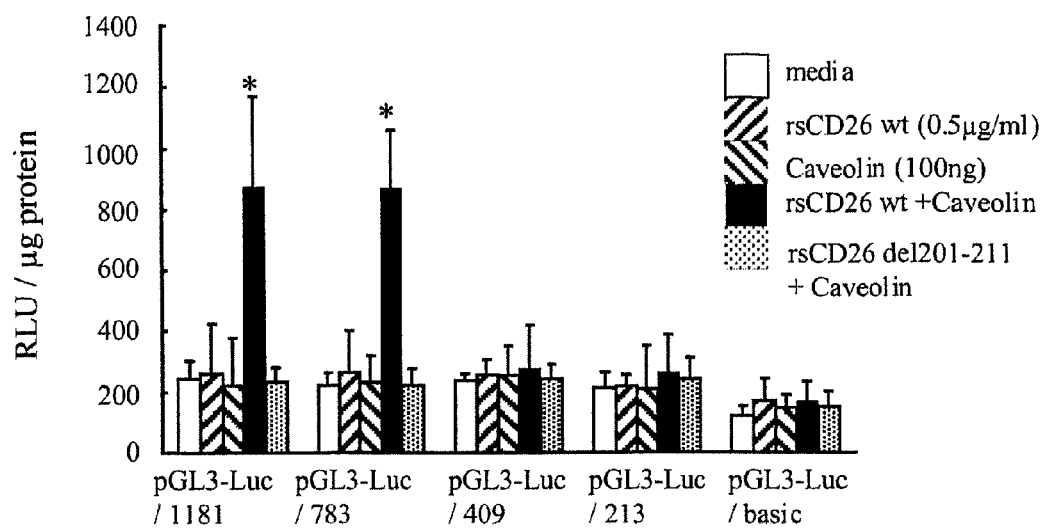
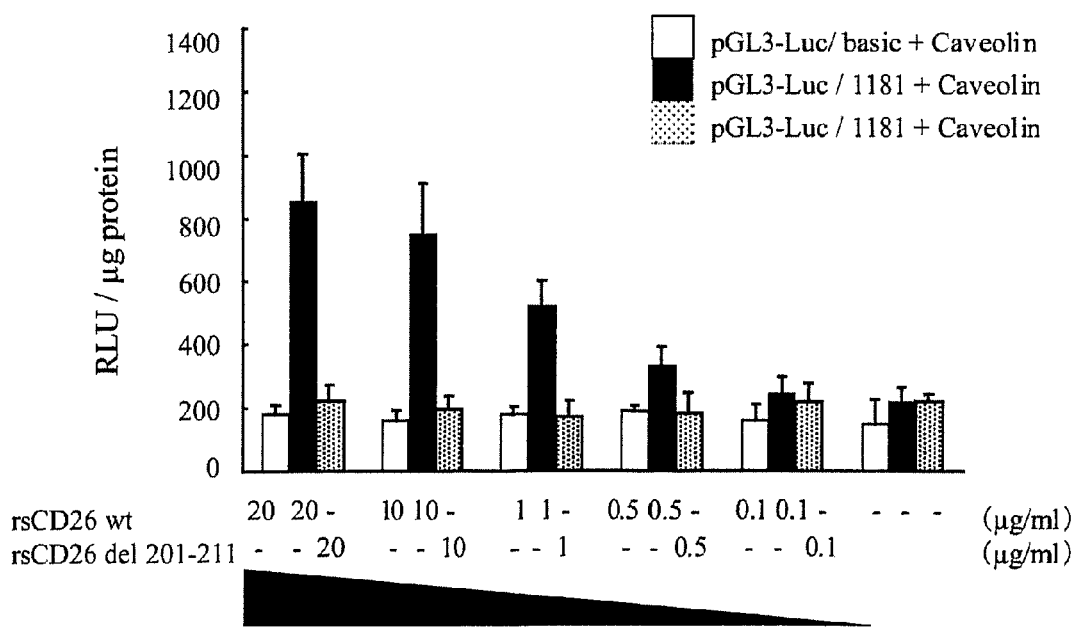

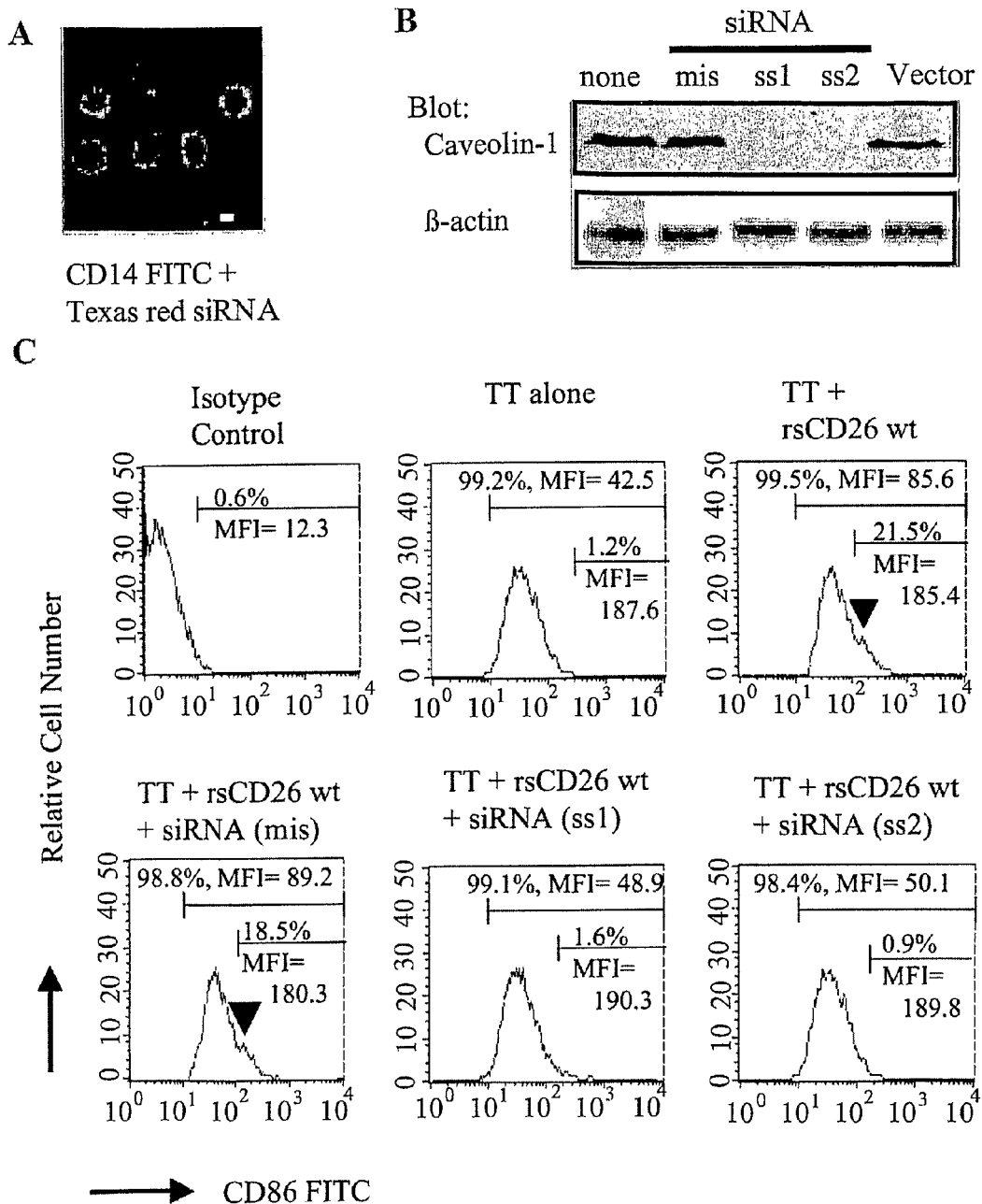

SEQUENCE LISTING

```
<160> NUMBER OF SEQ ID NOS: 12

<210> SEQ ID NO 1
<211> LENGTH: 59
<212> TYPE: DNA
<213> ORGANISM: Artificial Sequence
<220> FEATURE:
<223> OTHER INFORMATION: an artificially synthesized primer sequence

<400> SEQUENCE: 1
ggacgcgttt tagcattttg gtctaaacta atttataatt atttagcctt atttctcca         59

<210> SEQ ID NO 2
<211> LENGTH: 45
<212> TYPE: DNA
<213> ORGANISM: Artificial Sequence
<220> FEATURE:
<223> OTHER INFORMATION: an artificially synthesized primer sequence

<400> SEQUENCE: 2
ggacgcgttt ggaatttaaa atgttcaaaa tgatttgtct ggatg                        45

<210> SEQ ID NO 3
<211> LENGTH: 38
<212> TYPE: DNA
<213> ORGANISM: Artificial Sequence
<220> FEATURE:
<223> OTHER INFORMATION: an artificially synthesized primer sequence

<400> SEQUENCE: 3
ggacgcgttt ggttgtggaa attggcaggg ttaggtgg                                38

<210> SEQ ID NO 4
<211> LENGTH: 37
<212> TYPE: DNA
<213> ORGANISM: Artificial Sequence
<220> FEATURE:
<223> OTHER INFORMATION: an artificially synthesized primer sequence

<400> SEQUENCE: 4
ggacgcgtat tcaggctcat cttaacgtca tgtctgg                                 37

<210> SEQ ID NO 5
```

```
<211> LENGTH: 32
<212> TYPE: DNA
<213> ORGANISM: Artificial Sequence
<220> FEATURE:
<223> OTHER INFORMATION: an artificially synthesized primer sequence

<400> SEQUENCE: 5
cgctcgagtg tgctagtccc tgttacagca gc                                     32

<210> SEQ ID NO 6
<211> LENGTH: 23
<212> TYPE: DNA
<213> ORGANISM: Artificial Sequence
<220> FEATURE:
<223> OTHER INFORMATION: an artificially synthesized oligonucleotide for
      siRNA
<220> FEATURE:
<221> NAME/KEY: misc_feature
<223> OTHER INFORMATION: combined DNA/RNA sequence
<220> FEATURE:
<221> NAME/KEY: misc_feature
<222> LOCATION: (22)..(23)
<223> OTHER INFORMATION: n is 2'-deoxythymidine

<400> SEQUENCE: 6
aacaacaagg ccauggcaga cnn                                               23

<210> SEQ ID NO 7
<211> LENGTH: 23
<212> TYPE: DNA
<213> ORGANISM: Artificial Sequence
<220> FEATURE:
<223> OTHER INFORMATION: an artificially synthesized oligonucleotide for
      siRNA
<220> FEATURE:
<221> NAME/KEY: misc_feature
<223> OTHER INFORMATION: combined DNA/RNA sequence
<220> FEATURE:
<221> NAME/KEY: misc_feature
<222> LOCATION: (22)..(23)
<223> OTHER INFORMATION: n is 2'-deoxythymidine

<400> SEQUENCE: 7
aaggagaucg accuggucaa cnn                                               23

<210> SEQ ID NO 8
<211> LENGTH: 23
<212> TYPE: DNA
<213> ORGANISM: Artificial Sequence
<220> FEATURE:
<223> OTHER INFORMATION: an artificially synthesized oligonucleotide for
      siRNA
<220> FEATURE:
<221> NAME/KEY: misc_feature
<223> OTHER INFORMATION: combined DNA/RNA sequence
<220> FEATURE:
<221> NAME/KEY: misc_feature
<222> LOCATION: (22)..(23)
<223> OTHER INFORMATION: n is 2'-deoxythymidine

<400> SEQUENCE: 8
uacaagaagg gcauggcaga cnn                                               23

<210> SEQ ID NO 9
<211> LENGTH: 23
<212> TYPE: DNA
<213> ORGANISM: Artificial Sequence
<220> FEATURE:
<223> OTHER INFORMATION: an artificially synthesized oligonucleotide for
      siRNA
<220> FEATURE:
```

```
<221> NAME/KEY: misc_feature
<223> OTHER INFORMATION: combined DNA/RNA sequence
<220> FEATURE:
<221> NAME/KEY: misc_feature
<222> LOCATION: (22)..(23)
<223> OTHER INFORMATION: n is 2'-deoxythymidine

<400> SEQUENCE: 9
aaguuggcca agaauuacgg cnn                                            23

<210> SEQ ID NO 10
<211> LENGTH: 22
<212> TYPE: DNA
<213> ORGANISM: Artificial Sequence
<220> FEATURE:
<223> OTHER INFORMATION: an artificially synthesized oligonucleotide for
      siRNA
<220> FEATURE:
<221> NAME/KEY: misc_feature
<223> OTHER INFORMATION: combined DNA/RNA sequence
<220> FEATURE:
<221> NAME/KEY: misc_feature
<222> LOCATION: (21)..(22)
<223> OTHER INFORMATION: n is 2'-deoxythymidine

<400> SEQUENCE: 10
aacaaggauc cgccaucaac nn                                             22

<210> SEQ ID NO 11
<211> LENGTH: 23
<212> TYPE: DNA
<213> ORGANISM: Artificial Sequence
<220> FEATURE:
<223> OTHER INFORMATION: an artificially synthesized oligonucleotide for
      siRNA
<220> FEATURE:
<221> NAME/KEY: misc_feature
<223> OTHER INFORMATION: combined DNA/RNA sequence
<220> FEATURE:
<221> NAME/KEY: misc_feature
<222> LOCATION: (22)..(23)
<223> OTHER INFORMATION: n is 2'-deoxythymidine

<400> SEQUENCE: 11
uaguucgcca aguauuaccg cnn                                            23

<210> SEQ ID NO 12
<211> LENGTH: 11
<212> TYPE: PRT
<213> ORGANISM: Homo sapiens

<400> SEQUENCE: 12

Trp Val Tyr Glu Glu Glu Val Phe Ser Ala Tyr
1               5                   10
```

METHODS OF IDENTIFYING IMMUNOREGULATORY AGENTS, IMMUNOREGULATORY AGENTS, AND USES THEREOF

TECHNICAL FIELD

The present invention relates to a method for identifying an immunoregulatory agent. This invention also relates to immunoregulatory agents and their uses. In particular, the invention relates to a pharmaceutical composition comprising an immunoregulatory substance and its use for treating disorders related to an immune response.

BACKGROUND ART

The immune system functions are one of the biological function systems most essential to understanding the phenomenon of life. Essentially divided into self and non-self, the immune system is a biological defense mechanism with more than a trillion cells that control the maintenance of the living body by complex and dynamic processes, and without a tissue structure. However, because of this complexity and subtlety, failure of these functions generates a variety of diseases, including therapeutically difficult diseases. It is important to understand the inflammatory reactions in infectious diseases, auto-immune diseases accompanying tissue destruction, and rejection during transplantation.

Antigen invasion into cells in the first stages of inflammation is nonspecific, or occurs via antibody and complement receptors. Antigens taken up into cells are processed into peptide fragments, and presented to T cells as a complex with major histocompatibility complex (MHC) class II molecules. In these antigen presenting cells (APCs) are dendritic cells, macrophages, B cells, Langerhans cells, interdigitating cells, monocytes in peripheral blood, and so on; that is, the so-called professional APCs. Depending on differences in the expression levels of the coreceptor molecules CD80 and CD86, and differences in the type of cytokines that are produced, a bias will arise in subsequent helper T cell (Th cell) divisions. Th2 types, which are mainly concerned with humoral immunity under the influence of IL-4, are dominant over Th1 types, which play a large role in cellular immunity under the influence of interleukin-12 (IL-12). In this way, primary effector cells are activated, or antibody production is induced, and sensitization is established. At the same time, memory T cells and memory B cells are produced. Primary effector cells, starting from Th1 cells, include cytotoxic T lymphocytes (CTL), mast cells, monocytes, macrophages, basophils, neutrophils, NK cells, platelets and the like. The action of cytokines, chemokinds, chemical mediators and such, which are produced by the activation of primary effector cells, activates vascular endothelial cells in the inflamed area. The activation of secondary effector cells, such as monocytes, macrophages, neutrophils, eosinophils and so on, is induced, and inflammation arises. Finally, the inflammation reaction is suppressed by phagocytosis of causative substances or effector cell apoptosis by Fas/Fas-L at the inflamed region, and transduction of immunoreceptor tyrosine-based inhibitory motif (ITIM) inhibition signals by CTLA-4 and FcγRIIB and so on.

The onset mechanism of autoimmune diseases is still unknown, however, research is progressing into where the cause of the above-mentioned process may lie. Despite the fact that in inflammation induction in post-organ transfer rejection and graft-versus-host-disease (GVHD) is very clearly caused by the invasion of foreign antigens, these diseases are still not completely controlled.

Other than Th cells and CTL cells, as mentioned above, auto-antibody production and a variety of effector functions of complements, cytokines and the like contribute to the inflammation reactions accompanying tissue destruction that occurs with immune abnormalities such as autoimmune disease and rejection, GVHD and so on. To control these effector functions for disease therapies, a number of immunesuppression therapies have been attempted. Many of these targeted T cells, and thus, the focus in controlling immune abnormalities is becoming control of effector T cells. Therefore, the study of T cells as inflammation effector cells can be said to be extremely important for the treatment of immune abnormalities.

Based on the above, the present inventors focused on studies of CD26. CD26 positive T cells are Th1 type cells, a subset that very easily migrates to the inflamed region. They contribute to autoimmune diseases such as rheumatoid arthritis, and immune abnormalities such as rejections and GVHD, and are known to accumulate in diseased regions. Thus, by furthering the understanding of CD26 positive T cells, more pathology-specific therapeutic methods can be established.

CD26 is a widely distributed 110-kDa cell surface glycoprotein consisting of 766 amino acids with known dipeptidyl peptidase IV (DPPIV, EC3.4.14.5) activity in its extracellular domain (Morimoto, et al., 1998; von Bonin et al., 1998). This enzyme is capable of cleaving amino-terminal dipeptides with either L-proline or L-alanine at the penultimate position. The expression of CD26 is enhanced after activation of T cells in a resting state. In addition, the CD4+CD26$^{high}$ T cells respond maximally to recall antigens such as tetanus toxoid (Morimoto, et al., 1989). Accumulating evidence suggests that DPPIV enzyme activity plays a role in the immune response (Oravecz et al., 1997; Iwata, et al., 1999). Crosslinking of CD26 and CD3 with solid-phase immobilized monoclonal antibodies (mAbs) can induce T cell costimulation and IL-2 production by either human CD4+ T cells or Jurkat T cell lines transfected with CD26 cDNA (Tanaka, et al., 1992; Fleischer, et al., 1994). In addition, anti-CD26 antibody treatment of T cells leads to a decrease in the surface expression of CD26 via its internalization, and such modulation results in an enhanced proliferative response to anti-CD3 or anti-CD2 stimulation as well as enhanced tyrosine phosphorylation of signaling molecules such as CD3ζ and p56-Lck (Hegen, et al., 1997). Moreover, DPPIV enzyme activity is required for the CD26-mediated T cell costimulation (Tanaka, et al., 1993). A recent report showed that internalization of CD26 after crosslinking is mediated in part by the mannose-6-phosphate/insulin-like growth factor II receptor (M6P/IGF-IIR), and that the interaction of CD26 and M6P/IGFIIR plays a role in CD26-induced T cell costimulation (Ikushima, et al., 2000).

Maximal T cell activation requires both an antigen (Ag)-specific stimulus provided by an MHC peptide complex and a costimulatory signal (Lenschow, et al., 1996). Engagement of CD28 on the surface of T cells by B7-1 (CD80) or B7-2 (CD86) expressed on antigen presenting cells (APC) provides a potent costimulatory signal (Yokochi, et al., 1982; Azuma, et al., 1993; Freeman, et al., 1993; Lenschow, et al., 1996; McAdam, et al., 1998). CD28-B7 interactions lead to T cell proliferation, differentiation, and cytokine secretion (McAdam, et al., 1998; Chambers, 2001). In contrast, engagement of CTLA-4 on activated T cells by B7-1 or B7-2 results in an inhibition of T cell responses (Croft, et al., 1992; Walunas, et al., 1994; Krummel, et al., 1995). However, only CD28 is constitutively expressed, and hence it has an important role in the generation of T cell immune response (Fraser, et al., 1992; Caux, et al., 1994; Hathcock, et al., 1994; yi-qun, et al., 1996; Hakamada-Taguchi, et al., 1998; Manickasingham, et al., 1998).

Recombinant soluble CD26 (rsCD26) reportedly enhanced proliferative responses of peripheral blood lymphocytes (PBLs) to stimulation with the soluble antigen tetanus toxoid (TT) (Tanaka, et al., 1994). A more recent report demonstrated that the target cells of rsCD26 were the CD14 positive monocytes in the peripheral blood, and that rsCD26 could upregulate CD86 expression, but not CD80 or HLA-DR antigen levels on monocytes (Ohnuma, et al., 2001). M6P/IGF-IIR is thought to be one of the platform molecules for CD26 interaction with APC. However, while both DPPIV-positive and DPPIV-negative rsCD26 were taken up by monocytes via M6P/IGF-IIR, only DPPIV-positive rsCD26 displayed an effect of CD86 upregulation on monocytes, thus suggesting that additional factors may interact with CD26 to directly induce CD86 upregulation on monocytes. Moreover, the molecular mechanism for the maximal response of CD4+ $CD26^{high}$ T cells to the memory antigens has not yet been clarified.

Caveolin-1 is the primary coat protein of caveolae, and is involved as a regulator of signal transduction through binding of its scaffolding domain to key signaling molecules in various cells (Smart, et al., 1999; Peiro, et al., 2000; Carver, et al., 2003). Although CD26 was present in caveolae of fibroblast-like synoviocytes (Riemann, et al., 2001), its direct binding or signaling event was not demonstrated in immune cells.

DISCLOSURE OF THE INVENTION

An objective of this invention is to provide a molecule that interacts with CD26 to directly induce CD86 upregulation on monocytes.

The present inventors attempted to identify CD26-interacting molecules directly involved in the upregulation of CD86 and found that CD26 bound caveolin-1 on APC, and identified that residues 201 to 211 in CD26 along with the serine catalytic site at residue 630, which constitute a pocket structure of CD26/DPPIV (Rasmussen, et al., 2003), contributed to binding to the scaffolding domain of caveolin-1. Following binding of CD26 to caveolin-1 on APC, caveolin-1 was phosphorylated and released Toll-interacting protein (Tollip) from caveolin-1 into the cytosol. Moreover, release of Tollip from caveolin-1 led to phosphorylation of RAK (interleukin-1 receptor (IL-1R) associated serine/threonine kinase), which links to activated NF-κB, followed by upregulation of CD86 and subsequent engagement of CD28 molecule on T cells. CD86 upregulation resulted in potent T cell-APC interaction, leading to the development of activated memory T cells locally and activation of the immune response, and the consequence of various inflammatory diseases. Furthermore, the inventors found that caveolin-1 binds to Tollip and IRAK-1 in APC simultaneously.

The inventors showed here that CD26 was directly bound to caveolin-1 using a series of CD26 and caveolin-1 deletion mutants, and that caveolin-1 was phosphorylated following binding to CD26. Caveolin-1 was reported to be an integral membrane protein with a cytoplasmic N-terminal domain and a cytoplasmic C-terminal domain (Smart, et al., 1999). As shown in FIG. 2A, the N-terminal domain of caveolin-1 was expressed on cell surface of monocytes 12-24 hrs after tetanus toxoid was loaded. Since tetanus toxoid was trafficked in cells through caveolae (Montesano, et al., 1982; Pelknans, et al., 2002), caveolin-1 may be transported with the peptide-MHC complex developed in APC, and be expressed on cell surface by antigen-processing machinery for T cell contact (Grakoui, et al., 1999; Turley, et al., 2000). The data shown in FIG. 2C indicates that CD26 on activated memory T cells directly faced caveolin-1 on TT-loaded monocytes in the contact area, which was revealed as the immunological synapse for T cell-APC interaction. It is conceivable that the interaction of CD26 with caveolin-1 on antigen-loaded monocytes resulted in the upregulation of CD86, therefore enhancing the subsequent interaction of CD86 and CD28 on T cells to induce antigen-specific T cell proliferation and activation.

By studying the crystal structure of CD26/DPPIV, the horizontal helix of residues 201-207 was situated in front of the DPPIV enzyme active site at the serine residue 630. This small horizontal cavity allowed substrate amino acids to reach the active-site serine residue 630 and is involved in the DPPIV activity of CD26 (Rasmussen, et al., 2003). In this regard, this horizontal cavity has an essential role in caveolin-1 binding as well as DPPIV enzyme activity. In particular, CD26 mutants del 201-211 and S630A, in which this cavity was destroyed, had lost the ability to associate with caveolin-1 (FIGS. 1G, 1H, 3A, and 3B), and did not exert an effect on CD86 upregulation on monocytes (Ohnuma, et al., 2001). In addition, binding of CD26 to caveolin-1 was inhibited by the competitive inhibitor of DPPIV, valine-pyrrolidide (FIG. 1H-*m*, n, o). The valine-pyrrolidide (Val-Pyr) is bound in a smaller pocket within the DPPIV enzymatic active site (Rasmussen, et al., 2003), and two glutamic acids in the horizontal helix of CD26, Glu205 and Glu206, form salt bridges to the free amino group of Val-Pyr. Thus Val-Pyr blocks the accessibility of amino acids to the enzymatic cavity. These findings explain the previous work showing that CD26 lacking DPPIV enzymatic activity could not induce the enhancement of TT-mediated T cell proliferation as well as upregulation of CD86.

One striking feature presented in this invention is that caveolin-1 was associated with Tollip in monocytes (FIGS. 3B-H). It was reported previously that Tollip was involved in IL-1R/Toll-like receptor mediated signaling, and that it linked IRAK to NF-κB, JNK and p38 MAP kinase (Cao, et al., 1996; Burns, et al., 2000). Other investigators described that Tollip was associated with Toll-like IL-1R/Toll-like receptor and IRAK complexes, and that removal of Tollip from the complexes would allow signaling to continue by freeing activated IRAK to bind to downstream TRAF6 (Zhang, et al., 2002). Although IRAK was not detected in the complex of caveolin-1 and Tollip, CD26 and caveolin-1 were associated, and caveolin-1 was aggregated in the contact area, followed by caveolin-1 phosphorylation. Phosphorylated caveolin-1 subsequently released Tollip presumably due to conformational changes, and Tollip found in the cytoplasm then associated with IRAK for phosphorylation. The present inventors have now found that caveolin-1 and Tollip are complexed with IRAK-1 to form a triad (FIGS. 7A, C, and D).

We next explored the role of the 5'-flanking region of the human CD86 gene in regulating expression of this gene following the interaction of CD26-caveolin-1. The cloning and functional analysis of a 1.3 kilo-base pairs fragment upstream of the transcriptional site of the CD86 gene indicated that two NF-κB binding sites were required for the upregulation of CD86 after CD26-caveolin-1 interaction (FIG. 4C). Moreover, in transcription factor assay of TT-loaded monocytes stimulated with CD26, levels of NF-κB (p50 and p65) were detected to be significantly higher than those of STAT-1, or AP-1 (c-Fos, c-Jun) (FIG. 4A). In this regard, several other factors, such as IFNγ, TNFα, or CD40-CD154 ligation, were also reported to be involved in the upregulation of CD86 (Berberish, et al., 1994; Li, et al., 1999; Gordon, 2002).

Since loss of caveolae in monocytes was not reported in a caveolin-1 knock-out mouse model (Drab, et al., 2001), and the role and distribution of CD26 in human may be different from that of mouse (Morimoto, et al., 1998), we utilized the RNAi method to analyze directly the function of native caveolin-1 in purified human monocytes. During the past several years, it is shown that RNAi is very effectively utilized in mammalian cells with sequence-specific, small (19- to 22-nucleotides) double strand RNAs (Elbashir, et al., 2001). Although this approach helps to identify the mammalian gene function, one important limitation is that siRNA-based technology only provides a "knock-down" of the targeted protein but not a "knockout". Caveolin-1 is expressed constitutively in monocytes as well as other human tissues including endothelia, fibroblasts, and adipocytes, and treatment of purified human monocytes with siRNA resulted in knockout of caveolin-1 and inhibition of CD86 upregulation following stimulation with CD26-coated beads (FIGS. 5A-D). siRNA against Tollip in monocytes attenuated TT-loaded T cell proliferation induced by CD26 (FIGS. 8B and C). Therefore, our findings strongly suggest that caveolin-1 and Tollip are directly involved in CD86 upregulation in monocytes.

On the basis of our results and previously reported findings, we propose a model to describe the signaling events in monocytes triggered by CD26-caveolin-1 interaction (FIG. 6A). In this model, caveolin-1 is exposed to cell surface after tetanus toxoid is trafficked in monocytes, and CD26 induces aggregation and phosphorylation of caveolin-1 expressed in T cell-APC contact area, removal of Tollip and subsequent phosphorylation of IRAK. This sequence of events allows for activation of NF-κB and transcription of the CD86 gene. Finally, the induction of CD86 expression and the interaction of CD86 on monocytes and CD28 on T cells resulted in the antigen-specific T cell activation and proliferation. In another model (FIG. 9), Tollip recruits IRAK-1 to caveolin-1 and release IRAK-1 following stimulation with CD26, bringing about CD86 upregulation. With regards to T cell-APC local interaction and immune response (FIG. 6B), entry of recall antigens via caveolae into APC leads to presentation of antigen peptides on MHC class II molecules and exposure of caveolin-1. Then, APC induces the activation of memory T cells through TCR and costimulatory molecules such as CD86/CD80-CD28, leading to formation of mature immunological synapse. Following the association between caveolin-1 on APC and CD26 on memory T cells, CD86 is upregulated on APC surface, and memory T cells are subsequently activated via the costimulatory effect of CD26 on enhancement of TCR activation (Hegen, et al., 1997). By enhancing TCR activation by CD26-caveolin-1 interaction, prolongation of immunological synapse may be maintained (Huppa, et al., 2003).

Patients with autoimmune diseases such as rheumatoid arthritis, multiple sclerosis and Graves' disease have been found to have increased numbers of CD26$^{high}$ T cells in inflamed tissues as well as in their peripheral blood (Hafler, et al., 1985; Eguchi, et al., 1989; Mizokami, et al., 1996). In addition, enhancement of CD26 expression in these autoimmune diseases may correlate with disease severity. These findings imply that CD26$^{high}$ T cells play a role in the inflammation process and subsequent tissue damage in such diseases. In endothelial cells, inhibition of the scaffolding domain of caveolin-1 reduced inflammation by inhibition of eNOS (endothelial nitric oxide synthase), which was bound to caveolin-1 (Bucci, et al., 2000). The present invention provides a new approach to the treatment of autoimmune diseases or other immune-mediated disorders by directly interfering with activated memory T cell and APC interaction. Moreover, targeting the interaction of the pocket structure of CD26 and the scaffolding domain of caveolin-1 may lead to novel therapeutic approaches utilizing agonists or antagonists regulating antigen-specific immune response in not only immune-mediated disorders, but also cancer immunotherapy and viral vaccination as strategies to enhance immune response.

In one aspect, the present invention provides methods for identifying a substance that down-regulates or up-regulates an immune response and kits used for the methods. A method of this invention comprises detecting a substance that inhibits the interaction between CD26 and caveolin-1, in particular the interaction between the pocket structure of CD26 and the scaffolding domain of caveolin-1. Another method comprises detecting a substance that inhibits or enhances the interaction between caveolin-1 and Tollip, in particular the interaction between the scaffolding domain of caveolin-1 and the C2 domain of Tollip. Still another method comprises detecting a substance that inhibits or enhances the interaction among caveolin-1, Tollip, and IRAK, in particular the interaction between the scaffolding domain of caveolin-1 and the C2 domain of Tollip, and/or the interaction between the CUE domain of Tollip and the CT domain of IRAK-1.

The present invention also relates to immunoregulatory agents that inhibit or enhance the CD26 signaling pathway. The term "immunoregulatory agents" used herein include inhibitors, potentiators, antagonists, and agonists. Immunoregulatory agents that inhibit the CD26 signaling pathway may comprise an siRNA against caveolin-1 or an siRNA against Tollip as an active ingredient. The active ingredient may also be a substance obtained by the identification methods as mentioned above.

In addition, the present invention provides uses of immunoregulatory agents for treating inflammatory diseases, autoimmune diseases, or other immune-mediated disorders.

The words "a", "an", and "the" as used herein mean "at least one" unless otherwise specifically indicated.

One aspect of the invention involves methods of determining whether a substance modulates an immune response in an animal by modulating the stimulatory actions of CD26 on the immune system. This aspect involves methods of determining whether a substance modulates any action of CD26 or any downstream factor in the signaling pathway of CD26. In one embodiment, methods are provided for identifying a substance that down-regulates an immune response in an animal, comprising determining whether a substance inhibits an interaction between factors in the CD26 signaling pathway. In one embodiment, methods of determining whether a substance inhibits the interaction between CD26 and caveolin-1, in particular the interaction between the pocket structure of CD26 and the scaffolding domain of caveolin-1, are provided. In another embodiment, methods of determining whether a substance inhibits the interaction between caveolin-1 and Tollip, in particular the interaction between the scaffolding domain of caveolin-1 and the C2 domain of Tollip, are provided. In a further embodiment, methods of determining whether a substance inhibits the interactions between caveolin-1, Tollip, and IRAK-1, in particular the interactions between the scaffolding domain of caveolin-1 and the C2 domain of Tollip, and/or the interaction between the CUE domain of Tollip and the CT domain of IRAK-1, are provided. In one embodiment, the methods are screening assays, wherein more than one substance is tested. In another embodiment, libraries of substances are tested.

Any method known in the art for identifying inhibitors of protein interactions or signaling may be used in the present invention. Techniques useful for the detection of protein interactions, e.g., binding, are well known in the art, and include, but are not limited to, immunoprecipitation, Western blotting, two hybrid systems, fluorescent microscopy, and affinity chromatography. See, e.g., Harlow et al., Antibodies: A Laboratory Manual, Cold Spring Harbor Laboratory, Cold Spring Harbor, N.Y., (1988); Sambrook et al., Molecular Cloning—A Laboratory Manual, 2nd ed., Vol. 1-3 (1989); Ausubel et al., Current Protocols in Molecular Biology, John Wiley & Sons, New York 3rd Edition, (2000). Protein interaction assays may be carried out using whole cells, cell extracts or isolated proteins. Any cells which express the proteins of interest (e.g., CD26, caveolin-1, Tollip, IRAK-1, NF-κB, CD86) may be used. The cells may express such proteins naturally (e.g., immune system cells such as T cells and monocytes) or recombinantly. Cells may be established cell lines (e.g., Jurkat T cells, THP-1 monocytes), newly created cell lines, or cells isolated from subjects, e.g., humans. For assays involving isolated proteins, the proteins may be naturally occurring or recombinantly expressed proteins. The proteins may be recombinantly expressed in eukaryotic or prokaryotic cells. The proteins may be isolated by purification methods routinely used in the art, e.g., immunoprecipitation, affinity chromatography, size exclusion chromatography, or ion exchange chromatography. The proteins used in the assays may be wild type proteins or may be mutants comprising one or more additions, deletions, or substitutions. Full length proteins or truncated proteins comprising interaction domains may be used. For example, the scaffolding domain (amino acid residues 82-101) of caveolin-1 may be used. Similarly, the pocket structure of CD26 comprising the caveolin-binding consensus motif (amino acid residues 201-211) and amino acid residue 630 may be used. The C2 domain of Tollip (amino acid residues 47-178) may also be used. The proteins may be modified to include tags that are useful for purification and identification, e.g., glutathione-S-transferase, hemagglutinin, Flag, or one or more his.

Substances that may be tested in the methods for inhibitory activity include, but are not limited to, proteins, peptides, antibodies, nucleic acids, oligonucleotides, natural products, organic molecules, extracts, and libraries of these substances.

The effect of substances on protein:protein binding may be assayed by any method known in the art. Substances may be tested for the ability to block any binding interaction in the CD26 signaling pathway, e.g., the binding of CD26 and caveolin-1, in particular the binding of the pocket structure of CD26 and the scaffolding domain of caveolin-1, the release of Tollip from caveolin-1, the binding of Tollip and IRAK-1, or the binding of caveolin-1 and IRAK-1, in particular the binding between the scaffolding domain of caveolin-1 and the C2 domain of Tollip, and/or the binding between the CUE domain of Tollip and the CT domain of IRAK-1.

An example of a suitable assay is immunoprecipitation, e.g., using an antibody specific for a protein of interest to precipitate the protein of interest and any protein bound to it from a cell extract. For example, a GST-linked CD26 or caveolin-1 protein can be added to monocytes or an extract from monocytes and then precipitated using an anti-GST antibody. The precipitated protein is then separated by electrophoresis and any proteins that were precipitated along with the GST-linked protein are identified by Western blotting. The ability of a substance to block the immunoprecipitation of a protein indicates an inhibitory action on the binding of the protein to the antibody-bound protein.

Another assay that may be used to analyze protein:protein binding is affinity chromatography. A protein of interest may be linked to a suitable support material. Suitable support materials (e.g., Sepharose beads) and linkers are well known in the art. The protein of interest may also be bound by a binding partner which itself is linked to a support material (e.g., CD26 bound to adenosine deaminase-linked Sepharose beads). The linked protein is then contacted with a cellular extract such that proteins in the extract may bind to the linked protein. After washing away unbound proteins, any proteins that remain bound to the protein of interest may be eluted and identified, e.g., by Western blotting or peptide mass fingerprinting. The ability of a substance to block the binding of a protein to the linked protein indicates an inhibitory action on the binding of the protein to the protein of interest.

A further suitable assay is the two hybrid system. In this cell-based assay one protein of interest (e.g., CD26) is prepared as a fusion protein with a transcriptional activation domain and a second protein of interest (e.g., caveolin-1) which binds to the first protein of interest is prepared as a fusion protein with a DNA binding domain. When the two proteins of interest bind to each other the transcriptional activation domain and the DNA binding domain are brought together and alter the expression of a reporter gene linked to a regulatory element recognized by the DNA binding domain. The ability of a substance to block the binding of the two proteins of interest and thereby alter the expression of the reporter gene indicates an inhibitory action on the binding of the two proteins of interest.

In addition to protein binding, other types of assays that relate to the CD26 signaling pathway are included within the invention. These include detecting the phosphorylation of caveolin-1 or IRAK-1. Antibodies specific to the phosphorylated and non-phosphorylated forms of these proteins are commercially available (Santa Cruz Biotechnology, Inc., Santa Cruz, Calif.; BD Transduction, Santa Cruz, Calif.) or more be raised using routine techniques well known in the art. The antibodies may be used to detect the level of the phosphorylated and unphosphorylated forms of each protein in whole cells, cell extracts, or solutions of purified proteins and other components. The ability of a substance to block the phosphorylation of caveolin-1 or IRAK-1 in response to activation of the CD26 signaling pathway indicates an inhibitory action on CD26 signaling.

Assays related to DNA binding and gene activation in the CD26 signaling pathway may also be used. Stimulation of the CD26 pathway results in activation of NF-κB and upregulation of CD86 (B7-2) expression. Assays that detect the activation of the DNA binding activity of NF-κB, e.g., the binding of NF-κB to polynucleotides comprising one or more NF-κB response elements in a reporter gene construct can be used to identify inhibitors of CD26 signaling. For example, assays can be performed using nuclear extracts from CD26-stimulated antigen presenting cells and oligonucleotides comprising one or more NF-κB response element in a DNA binding assay. Whole cell assays may also be employed. For example, the upstream regulatory region of the CD86 gene contains two NF-κB response elements. A reporter gene construct comprising the CD86 upstream region may be used to identify inhibitors of the NF-κB activation that follows stimulation of the CD26 pathway by detecting a change in expression of the reporter gene. Any suitable reporter gene known in the art may be used, e.g., luciferase, green fluorescent protein, and β-galactosidase. The ability of a substance to inhibit the increase in reporter gene expression indicates an inhibitory action on CD26 signaling.

The increase in the level of NF-κB protein or its two subunits (p50 and p65) in response to CD26 signaling can also be used to identify inhibitors of the CD26 pathway. The ability of a substance to inhibit the increase in p50 and p65 levels indicates an inhibitory action on CD26 signaling.

The measurement of expression of CD86, e.g., in whole cells in which the CD26 pathway has been stimulated, can be used to identify inhibitors of the CD26 signaling pathway. The cells may naturally express CD86 or may comprise a recombinant vector comprising the CD86 gene. The ability of a substance to inhibit the increase in CD86 expression indicates an inhibitory action on CD26 signaling.

The co-localization of interacting proteins (e.g., caveolin-1 and Tollip) can be assayed in living cells by transfecting cells with proteins fused to a sequence detectable in living cells, e.g., green fluorescent protein. The ability of a substance to block the co-localization of interacting proteins in the CD26 pathway indicates an inhibitory action on CD26 signaling.

Assays involving the detection of cellular interactions may also be used. For example, the interaction of T cells expressing CD26 and antigen presenting cells (e.g., monocytes) expressing caveolin-1 may be detected as a method of identifying inhibitors of the interaction between CD26 and caveolin-1. Activated T cells and antigen-loaded monocytes may be mixed to form conjugates, stained with fluorescently labeled antibodies, and the recruitment of CD26 and caveolin-1 to the contact area of the cells detected by confocal laser microscopy. To mimic the interaction of activated T cells and antigen-loaded antigen presenting cells, antigen presenting cells may be stimulated by contacting the cells with soluble CD26 or CD26-coated beads. The ability of a substance to block the recruitment of CD26 and caveolin-1 to the contact area of the cells indicates an inhibitory action on CD26 signaling.

In one aspect of the invention, kits are provided for identifying modulators of the CD26 signaling pathway. In certain embodiments, kits are provided that may be used to identify substances that inhibit or enhance the interaction between CD26 and caveolin-1, in particular the interaction between the pocket structure of CD26 and the scaffolding domain of caveolin-1, substances that inhibit or enhance the interaction between caveolin-1 and Tollip, in particular the interaction between the scaffolding domain of caveolin-1 and the C2 domain of Tollip, or substances that inhibit or enhance the interactions between caveolin-1, Tollip, and IRAK-1, in particular the interactions between the scaffolding domain of caveolin-1 and the C2 domain of Tollip, and/or the binding between the CUE domain of Tollip and the CT domain of IRAK-1. The kits may be used to determine the level or function of at least one factor in the CD26 signaling pathway, e.g., CD26, caveolin-1, Tollip, IRAK-1, NF-κB, or CD86. In this embodiment, a kit is provided, with one or more containers comprising at least one agent which may be used to determine the level or function of at least one factor in the CD26 signaling pathway. Agents include, but are not limited to, one or more proteins, protein fragments, or hybrid proteins selected from CD26, caveolin-1, Tollip, IRAK-1, NF-κB, or CD86, one or more nucleic acids encoding proteins, protein fragments, or hybrid proteins selected from CD26, caveolin-1, Tollip, IRAK-1, NF-κB, or CD86, one or more antibodies that specifically bind to proteins, protein fragments, or hybrid proteins selected from CD26, caveolin-1, Tollip, IRAK-1, NF-κB, or CD86, reporter gene constructs, or cells. In various other embodiments, the kit can also comprise, e.g., a buffering agent, a preservative, or a protein or nucleic acid stabilizing agent. The kit also can comprise components necessary for detecting the agent (e.g., an enzyme or a substrate). The kit also can contain a control sample or a series of control samples which can be assayed and compared to the test sample. Each component of the kit is usually enclosed within an individual container and all of the various containers are within a single package along with instructions for carrying out identification assays.

One aspect of the present invention is a method for treating, ameliorating, or preventing a disorder related to an immune response in an animal comprising administering to the animal a therapeutically effective amount of an immunoregulatory agent that inhibits or enhances the CD26 signaling pathway. Another aspect of the present invention is a method for treating, ameliorating, or preventing a disorder related to an immune response in an animal comprising administering to the animal a therapeutically effective amount of an immunoregulatory agent that inhibits or enhances the CD26 signaling pathway and one or more therapeutic agents, which therapeutic agents are currently being used, have been used, or are known to be useful in the treatment, amelioration, or prevention of a disorder related to an immune response. On embodiment of the invention encompasses the use of an immunoregulatory agent that inhibits the CD26 signaling pathway in the manufacture of a medicament for treating, ameliorating, or preventing a disorder related to an immune response in an animal. In preferred embodiments of the invention, the disorder is an autoimmune disorder, an inflammatory disorder, acute or chronic GVHD (graft-versus-host-disease) or transplant rejection.

The methods described herein are useful for the treatment or amelioration of autoimmune disorders including, but not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behget's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barré syndrome, Hashimoto's thyroiditis, idiopathic pulmonary fibrosis, idiopathic thrombocytopenia purpura, IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, rheumatoid arthritis, sarcoidosis, scleroderma, progressive systemic sclerosis, Sjögren's syndrome, Goodpasture's syndrome, stiffman syndrome, systemic lupus erythematosus, lupus erythematosus, Takayasu's arteritis, temporal arteritis, giant cell arteritis, ulcerative colitis, uveitis, vasculitides such as dermatitis herpetiformis vasculitis, vitiligo, and Wegener's granulomatosis.

The methods described herein are useful for the treatment or amelioration of inflammatory disorders including, but not limited to, asthma, encephalitis, inflammatory bowel disease (e.g., Crohn's disease and ulcerative colitis), chronic obstructive pulmonary disease, inflammatory osteolysis, allergic disorders, septic shock, pulmonary fibrosis (e.g., idiopathic pulmonary fibrosis), inflammatory vasculitides (e.g., polyarteritis nodosa, Wegener's granulomatosis, Takayasu's arteritis, temporal arteritis, and lymphomatoid granulomatosus), post-traumatic vascular angioplasty (e.g., restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

The methods described herein are useful for the treatment, amelioration, or prevention of acute or chronic GVHD (graft-versus-host-disease), or a transplant rejection including, but not limited to, a liver transplant rejection, a kidney transplant rejection, a bone transplant rejection, a skin transplant rejection, a heart transplant rejection, a blood transfusion rejection, and an eye transplant rejection.

The term "disorder related to an immune response," as used herein, refers to disorders or diseases caused by the body's immune response. In a specific embodiment, a disorder related to an immune response is a disorder caused by an abnormal or uncontrolled T cell-mediated response. In another specific embodiment, the disorder is caused by an abnormal or uncontrolled B cell-mediated response.

The term "immunoregulatory agent that inhibits the CD26 signaling pathway," as used herein, refers to any agent that interferes with any signal or interaction involving factors in the CD26 pathway such that an immune response is lessened, eliminated, or prevented.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of an inflammatory disorder or an autoimmune disorder characterized by inflammation, a therapeutically effective amount preferably refers to the amount of a therapeutic agent that reduces the inflammation of a joint, organ or tissue by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. With respect to the treatment of psoriasis, a therapeutically effective amount preferably refers to the amount of a therapeutic agent that reduces a human's Psoriasis Area and Severity Index (PASI) score by at least 20%, at least 25%, at least 30%, at least 35%, at least 40%, at least 45%, at least 50%, at least 55%, at least 60%, at least 65%, at least 70%, at least 75%, at least 80%, or at least 85%. Alternatively, with respect to the treatment of psoriasis, a therapeutically effective amount preferably refers to the amount of a therapeutic agent that improves a human's global assessment score by at least 25%, at least 35%, at least 30%, at least 40%, at least 45%, at least 50%, at least 55%, at least 60%, at least 65%, at least 70%, at least 75%, at least 80%, at least 85%, at least 90%, or at least 95%. With respect to the treatment of rheumatoid arthritis, a therapeutically effective amount preferably refers to the amount of a therapeutic agent that reduces a human's Disease Activity Score (DAS) score by at least 20%, at least 35%, at least 30%, at least 40%, at least 45%, at least 50%, at least 55%, at least 60%, at least 65%, at least 70%, at least 75%, at least 80%, or at least 85%. With respect to the treatment of systemic lupus erythematosus, a therapeutically effective amount preferably refers to the amount of a therapeutic agent that reduces a human's Systemic Lupus Activity Measure (SLAM) score by at least 20%, at least 35%, at least 30%, at least 40%, at least 45%, at least 50%, at least 55%, at least 60%, at least 65%, at least 70%, at least 75%, at least 80%, or at least 85%.

The term "transplant rejection," as used herein, refers to the rejection of a genetically non-identical tissue, organ, or graft by a recipient's immune system.

The terms "treat," "treatment," and "treating," as used herein, refer to the amelioration of one or more symptoms associated with a disorder related to an immune response that results from the administration of one or more therapeutic agents. In certain embodiments, such terms refer to a reduction in the swelling of one or more joints, or a reduction in the pain associated with an immune-mediated disorder resulting from the administration of one or more therapeutic agents to an animal with such a disorder. In other embodiments, such terms refer to a reduction in a human's PASI score, DAS score, or SLAM score. In other embodiments, such terms refer to an improvement in a human's global assessment score.

The terms "prevent," "preventing," and "prevention," as used herein, refer to a decrease in the occurrence of pathology from a disorder related to an immune response in an animal. The prevention may be complete, e.g., the total absence of pathology from a disorder related to an immune response in an animal. The prevention may also be partial, such that the occurrence of pathology from a disorder related to an immune response in an animal is less than that which would have occurred without the present invention.

The term "synergistic," as used herein, refers to an effect obtained when a first agent and a second agent are administered together (e.g., at the same time or one after the other) that is greater than the additive effect of the first agent and the second agent when administered individually. The synergistic effect allows for lower doses of the first agent and/or the second agent to be administered or provides greater efficacy at the same doses. The synergistic effect obtained can be at least 10%, at least 20%, at least 30%, at least 40%, at least 50%, at least 60%, at least 70%, at least 80%, at least 90%, at least 100%, at least 125%, at least 150%, at least 175%, at least 200%, at least 250%, at least 300%, at least 350%, at least 400%, or at least 500% more than the additive effect of the first agent and the second agent when administered individually.

In one aspect of the invention, immunoregulatory agents which are small interfering RNA (siRNA) molecules targeted to factors in the CD26 signaling pathway are provided. siRNAs are double stranded RNA molecules which are complementary to the sequence of a target gene and inhibit expression of the protein encoded by the gene. The synthesis and use of siRNAs to inhibit gene expression are well known in the art. See, e.g., U.S. Pat. No. 6,506,559 and Elbashir, et al., 2001. In one embodiment, the siRNA comprises a sequences from the open reading frame of the target gene of the type AA(N19), wherein N is any nucleotide. The sequence may further comprise a 2 nucleotide 3'overhang of 2'-deoxythymidine (dTdT) in order to generate a symmetric duplex. In one embodiment, siRNAs targeted to caveolin-1 are provided. In a particular embodiment, the siRNAs targeted to caveolin-1 consist of the sequence of SEQ ID NO:6 or SEQ ID NO:7. In one embodiment, siRNAs targeted to Tollip are provided. In a particular embodiment, the siRNAs targeted to Tollip consist of the sequence of SEQ ID NO:9 or SEQ ID NO:10.

siRNAs targeted to factors in the CD26 signaling pathway (e.g., caveolin-1, Tollip) may be used to study the CD26 pathway by inhibiting expression of the targeted factors. The siRNAs may also be used to treat immune disorders as described above.

The immunoregulatory agents of the present invention can be substances that are obtained by the identification methods as described above. Such substances include DPPIV inhibitors, such as valine-pyrrolidide, and caveolae trafficking inhibitors, such as filipin.

The immunoregulatory agents of the present invention may be linked to a carrier molecule to enhance the cellular uptake of the compounds. Examples of such carrier molecules include carrier peptides such as those described by Fulda et al., Nature Med. 8:808 (2002), Arnt et al., J. Biol. Chem. 277:44236 (2002), and Yang et al., Cancer Res. 63:831 (2003), fusogenic peptides (see, e.g., U.S. Pat. No. 5,965,404), and viruses and parts of viruses such as empty capsids and virus hemagglutinin (see, e.g., U.S. Pat. No. 5,547,932). Other carrier molecules include ligands for cell surface receptor such as asialoglycoprotein (which binds to the asialoglycoprotein receptor; see U.S. Pat. No. 5,166,320) and antibodies to cell surface receptors such as antibodies specific for T-cells, e.g., anti-CD4 antibodies (see U.S. Pat. No. 5,693,509).

Compositions within the scope of this invention include all compositions wherein the immunoregulatory agents of the present invention are contained in an amount which is effective to achieve its intended purpose. While individual needs vary, determination of optimal ranges of effective amounts of each component is within the skill of the art. The actual dosage and treatment regimen can be readily determined by the ordinary skilled physician, taking into account the route of administration, age, weight, and health of the subject, as well as the stage of the disorder, and, of course, any side effects of the agents, efficacy of the agents, and in accordance with customary medical procedures and practices. Typically, the agents may be administered to mammals, e.g. humans, orally at a dose of 0.0025 to 50 mg/kg, or an equivalent amount of the pharmaceutically acceptable salt thereof, per day of the body weight of the animal being treated for the disorder. Preferably, about 0.01 to about 10 mg/kg is orally administered to treat, ameliorate, or prevent the disorder. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of each agent. The unit dose may be administered one or more times daily as one or more tablets or capsules each containing from about 0.1 to about 10, conveniently about 0.25 to 50 mg of the agents.

In addition to administering immunoregulatory agents as raw chemicals, the agents of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil such as almond oil, is admixed. A typical example of such a cream is one which includes approximately: 40 parts water, 20 parts beeswax, 40 parts mineral oil, and 1 part almond oil.

Ointments may be formulated by mixing a solution of the active ingredient in a vegetable oil, such as almond oil with warm soft paraffin and allowing the mixture to cool. A typical example of such an ointment is one which includes approximately: 30% almond oil and 70% white soft paraffin by weight.

The combination therapies of the invention comprise an immunoregulatory agent that inhibits or enhances the CD26 signaling pathway and at least one other therapeutic agent which has a different mechanism of action than the immunoregulatory agent that inhibits or enhances the CD26 signaling pathway. The mechanisms of therapeutic agents other than the immunoregulatory agent that inhibits or enhances the CD26 signaling pathway which can be used in the combination therapies of the present invention can be found in the art (see, e.g., Hardman et al., eds., Goodman & Gilman's The Pharmacological Basis Of Basis Of Therapeutics 10th Ed, Mc-Graw-Hill, New York, 2002; Physician's Desk Reference (PDR) 58th Ed., Medical Economics Co., Inc., Montvale, N.J. (2004) (www.pdr.net), and the emedicine website. The combination therapies of the present invention also comprise an immunoregulatory agent that inhibits or enhances the CD26 signaling pathway and at least one other therapeutic agent which improves the therapeutic effect of the immunoregulatory agent that inhibits or enhances the CD26 signaling pathway by functioning together with the immunoregulatory agent that inhibits or enhances the CD26 signaling pathway to have an additive or synergistic effect. An immunoregulatory agent that inhibits or enhances the CD26 signaling pathway may be administered prior to (e.g., 0.5 hours, 1 hour, 2 hours, 4 hours, 6 hours, 12 hours, 24 hours, 36 hours, 48 hours, 5 days, 1 week, 2 weeks, 1 month or more before), subsequent to (e.g., 0.5 hours, 1 hour, 2 hours, 4 hours, 6 hours, 12 hours, 24 hours, 36 hours, 48 hours, 5 days, 1 week, 2 weeks, 1 month or more after), or concomitantly with the administration of one or more therapeutic agents other than an immunoregulatory agent that inhibits or enhances the CD26 signaling pathway.

In accordance with the present invention, an immunoregulatory agent that inhibits or enhances the CD26 signaling pathway may be advantageously utilized in combination with one or more therapeutic agents. Such combinational use may reduce adverse side effects associated with the administration of both the immunoregulatory agent that inhibits or enhances the CD26 signaling pathway and the other therapeutic agent. For example, the administration of an immunoregulatory agent that inhibits or enhances the CD26 signaling pathway may reduce the dosage and/or frequency of administration of one or more dosages of known therapeutic agents for the treatment or amelioration of a particular disorder related to an immune response.

Examples of therapeutic agents used to treat or ameliorate rheumatoid arthritis include, but are not limited to, Remicade, corticosteroids, tacrolimus, bisphosphonates, NSAIDs (e.g., ibuprofen, fenprofen, indomethacin, and naproxen), anti-malarial drugs (e.g., hydroxychloroquine and sulfasalazine), Anakinra, azathioprine, Enbrel, Celebrex, and cyclophosphamide. Examples of therapeutic agents used to treat or ameliorate Crohn's disease include, but are not limited to, sulfasalazine (Azulfidine), aminosalicylates, steroids (e.g., prednisone), and infliximab. Examples of therapeutic agents used to treat or ameliorate systemic lupus erythematosus include, but are not limited to, NSAIDs, antimalarial drugs (e.g., hydroxychloroquine), corticosteroids, glucocorticoids (e.g., triamcinolone), methotrexate, and azathioprine. Examples of therapeutic agents used to treat or ameliorate asthma include, but are not limited to, corticosteroids (Azmacort, Vanceril, AeroBid, Flovent, prednisone, methylprednisone, and hydrocortisone), leukotriene inhibitors, aminophylline and theophylline. Examples of therapeutic agents used to treat or ameliorate autoimmune hepatitis include, but are not limited to, corticosteroids (e.g., prednisone), azathiopurine and mercaptopurine. Examples of therapeutic agents used to treat, ameliorate, or prevent transplant rejection include, but are not limited to, azathioprine, cyclosporine, mycophenolate mofetil, rapamune, corticosteroids, and OKT2 monoclonal antibodies. One example of a therapeutic agent used to treat or ameliorate multiple sclerosis is IFN-β-1a (Avonex).

Examples of therapeutic agents used to treat or ameliorate bullous systemic lupus include, but are not limited to, dapsone, corticosteroids (e.g., prednisone and triamcinolone), and methotrexate. Examples of therapeutic agents used to treat or ameliorate scleroderma include, but are not limited to, prednisone, azathioprine, methotrexate, cyclophosphamide, and penicillamine. Examples of therapeutic agents used to treat or ameliorate pyoderma gangrenosum include, but are not limited to, prednisone, azathioprine, cyclophosphamide, chlorambucil, tacrolimus, immune globulins, and thalidomide. Examples of therapeutic agents used to treat or ameliorate alopecia areata include, but are not limited to, cyclosporine, methoxsalen, anthralin, clobetiasol propionate, prednisone, triamcinolone, betamethasone, and minoxidil. Examples of therapeutic agents used to treat or ameliorate vitiligo include, but are not limited to, triamcinolone, hydrocortisone, prednisone, methoxsalen, and trioxsalen. Examples of therapeutic agents used to treat or ameliorate contact dermatitis include, but are not limited to, clobetasol, hydrocortisone, prednisone, triamcinalone, hydroxyzine, doxepin, and disulfuran. Examples of known treatments for psoriasis include, but are not limited to, hydroxyurea, methotrexate, cyclosporin, acitretin, ultraviolet B radiation phototherapy, photochemotherapy, topical corticosteroids (e.g., diflorasone diacetate, clobetasol propionate, halobetasol propionate, betamethasone dipropionate, fluocinonide, halcinonide, desoximetasone, triamcinolone acetonide, fluticasone propionate, flucinolone acetonide, flurandrenolide, mometasone furoate, betamethasone, aclometasome dipropionate, desonide, and hydrocortisone), dithranol (anthralin), coal tar, salicylic acid, topical retinoids (e.g., tazarotene), macrolide antibiotics (e.g., tacrolimus), anti-CD3 monoclonal antibodies, anti-CD4 monoclonal antibodies, anti-CD11a monoclonal antibodies, anti-IL-2Rα monoclonal antibodies, anti-ICAM 1 antibodies, anti-LFA1 antibodies, anti-CD80 monoclonal antibodies, CTLA4Ig, and emollients.

The immunoregulatory agent that inhibits or enhances the CD26 signaling pathway and one or more therapeutic agents of the combination therapies of the present invention can be administered concomitantly or sequentially to an animal. The immunoregulatory agent that inhibits or enhances the CD26 signaling pathway and one or more therapeutic agents of the combination therapies of the present invention can also be cyclically administered. Cycling therapy involves the administration of a first therapeutic agent for a period of time, followed by the administration of a second therapeutic agent for a period of time and repeating this sequential administration, i.e., the cycle, in order to reduce the development of resistance to one of the agents, to avoid or reduce the side effects of one of the agents, and/or to improve the efficacy of the treatment. The immunoregulatory agent that inhibits or enhances the CD26 signaling pathway and one or more therapeutic agents of the combination therapies of the invention can be administered to a subject concurrently. The term "concurrently" is not limited to the administration of therapeutic agents at exactly the same time, but rather it is meant that an immunoregulatory agent that inhibits or enhances the CD26 signaling pathway and the one or more therapeutic agents are administered to an animal in a sequence and within a time interval such that the immunoregulatory agent that inhibits or enhances the CD26 signaling pathway can act together with the other agent(s) to provide an increased benefit than if they were administered otherwise. The immunoregulatory agent that inhibits or enhances the CD26 signaling pathway and one or more therapeutic agents can be administered separately, in any appropriate form and by any suitable route. In preferred embodiments, the immunoregulatory agent that inhibits or enhances the CD26 signaling pathway and one or more therapeutic agents are administered within the same patient visit. The immunoregulatory agent that inhibits or enhances the CD26 signaling pathway and one or more therapeutic agents of the combination therapies can be administered to an animal in the same pharmaceutical composition. Alternatively, the immunoregulatory agent that inhibits or enhances the CD26 signaling pathway and one or more therapeutic agents of the combination therapies can be administered concurrently to an animal in separate pharmaceutical compositions. The immunoregulatory agent that inhibits or enhances the CD26 signaling pathway and one or more therapeutic agents may be administered to an animal by the same or different routes of administration.

The administration of the immunoregulatory agent that inhibits or enhances the CD26 signaling pathway may be continued concurrently with the administration of the one or more therapeutic agents. Additionally, the administration of the immunoregulatory agent that inhibits or enhances the CD26 signaling pathway may be continued beyond the administration of the one or more therapeutic agents.

In certain embodiments of the invention, the method of administering an immunoregulatory agent that inhibits or enhances the CD26 signaling pathway in combination with one or more therapeutic agents may be repeated at least once. The method may be repeated as many times as necessary to achieve or maintain a therapeutic response, e.g., from one to about ten or more times. With each repetition of the method the immunoregulatory agent that inhibits or enhances the CD26 signaling pathway and the one or more therapeutic agents may be the same or different from that used in the previous repetition. Additionally, the time period of administration of the immunoregulatory agent that inhibits or enhances the CD26 signaling pathway and the manner in which it is administered can vary from repetition to repetition.

In certain embodiments, a therapeutic or pharmaceutical composition of the invention is administered prior to or after the presence of the symptoms or diagnosis of the disorder. For example, the pharmaceutical compositions of the invention may be administered prior to transplant surgery.

Animals which may be treated according to the present invention include all animals which may benefit from administration of the compounds of the present invention. Such animals include humans, pets such as dogs and cats, and veterinary animals such as cows, pigs, sheep, goats and the like.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications, and publications cited herein are incorporated by reference.

BRIEF DESCRIPTION OF THE DRAWINGS

FIG. 1A is a photograph of the indicated fractions that were subjected to SDS-PAGE followed by silver staining. Total cell lysate (Lysate) of THP-1 cells, an eluted fraction from mock purification (ADA beads), a flow-through fraction (Washout) from an eluted fraction of CD26-ADA sepharose column for THP-1 cells (Elution). Proteins eluted from CD26-ADA sepharose columns were identified by MS analysis, indicated on the right.

FIG. 1B presents photographs showing immunoblotting of THP-1 cells cocultured with soluble CD26 (sCD26) and immunoprecipitated (IP) with either anti-caveolin-1 (right panel) or anti-CD26 antibodies (left panel).

FIG. 1C schematically represents the bacterially produced GST-fused caveolin-1 and its mutants. Residues 1-81 comprised the N-terminal region (right dotted square), residues 82-101 comprised the scaffolding domain (SCD) (black square), residues 102-134 comprised the transmembrane region (striped square), and residues 135-178 comprised the C-terminal region (left dotted square).

FIG. 1D presents photographs showing immunoblotting of GST-fused caveolin-1 and its mutants, which were incubated with J.CD26 cell lysate, with anti-CD26 antibody, followed by stripping and reprobing with anti-GST antibody.

FIG. 1E presents photographs showing transfected HEK293 cells incubated with Texas red conjugated sCD26 (rsVD26 Texas red), visualized with confocal laser microscopy. The cells were transfected with GFP-fased wild type caveolin-1 (wt) (a-c), deletion mutant lacking the SCD (del 82-101) (d-f), and GFP vector alone (g-i). Bars indicate 10 μm scale.

FIG. 1F schematically represents the GST-fused CD26 and its deletion mutants, produced by COS-7 cells and purified with GSH beads. Transmembrane and cytosolic regions were deleted. Residues 201-211 contain a caveolin-binding domain (CBD). To delete DPPIV enzymatic activity, serine at residue 630 was mutated for alanine residue (S630A).

FIG. 1G presents photographs showing immunoblotting of GST-fused CD26 and deletion mutants, which were incubated with THP-1 cell lysate, with anti-caveolin-1 antibody, followed by stripping and reprobing with anti-GST antibody.

FIG. 1H presents photographs showing transfected HEK293 cells incubated with Texas red conjugated caveolin-1, visualized with confocal laser microscopy. The cells were transfected with GFP-fused wild type CD26 (wt) (a-c), deletion mutant lacking the CBD (del 201-211) (d-f), DPPIV activity-deleted mutant (S630A) (g-i) and GFP vector alone (j-l). HEK293 cells transfected with GFP-fused wild type CD26 (wt) were incubated with DPPIV inhibitor valine-pyrrolidide (Val-Pyr) prior to adding Texas red conjugated caveolin-1 (m-o). Texas red conjugated ADA was added to BEK293 cells transfected with GFP-fused wild type CD26 (wt) which were incubated with Val-Pyr (p-r). Bars indicate 10 μm scale.

FIG. 2 shows caveolin-1 in monocytes was exposed to cell surface after tetanus toxoid (TT) treatment, and interacted with CD26 on activated T cells.

FIG. 2A shows time course detection of caveolin-1 on the cell surface of monocytes. Monocytes were incubated with (solid circle) or without (open circle) TT for the indicated time periods, or preincubated with Filipin for 30 min, followed by incubation with (solid triangle) or without (open triangle) TT for the indicated time periods. Data of % positive cells represent mean±standard errors (SE) from five independent experiments. Asterisks indicate points of significant increase. Representative numbers of mean fluorescence intensity (MFI) of caveolin-1 in TT-loaded monocytes were shown.

FIG. 2B presents photographs showing colocalization of CD26 and caveolin-1 in T activated T cells and TT-loaded monocytes. Bars indicate 10 μm scale.

FIG. 2C presents photographs showing colocalization of CD26 and caveolin-1 in conjugates of activated T cells and TT-loaded monocytes. Three representative conjugates were shown (conj#1-#3). Bars indicate 10 μm scale.

FIG. 2D shows quantification of cell conjugation between T cells and monocytes. Monocytes were incubated with (solid circle) or without (open circle) TT for the indicated time periods, or preincubated with Filipin for 30 min, followed by incubation with (solid triangle) or without (open triangle) TT for the indicated time periods. Data represent mean±SE of T cell-monocyte conjugation frequency in 500 random cells in a coverslip analyzed in five independent experiments. Asterisks indicate points of significant increase.

FIG. 3 shows CD26 induced phosphorylation of caveolin-1 in TT-loaded monocytes, followed by release of Tollip to phosphorylate IRAK.

FIG. 3A presents photographs detecting caveolin-1 on TT-loaded monocytes incubated with polystyrene latex beads coated with wild type CD26 (wt) (a) or deletion mutant CD26 lacking the CBD (del201-211) (b). Cells and beads were visualized by confocal laser microscopy. Panels were phase contrast photos merged with FITC views. Bars indicate 10 μm scale.

FIG. 3B presents photographs showing immunoblotting of caveolin-1 in CD26 (wt)-stimulated TT-loaded monocytes with anti-phospho-caveolin-1 or anti-Tollip antibodies, followed by stripping and reprobing with anti-caveolin-1 antibody, and photographs showing immunoblotting of monocyte lysates with anti-IRAK antibody (upper panel). Position of IRAK bands was indicated by open arrow heads, and supershifted bands of IRAK was indicated by solid arrow head. The bottom panel shows a bar graph showing the reciprocal intensities of phospho-caveolin (open bars) and Tollip (solid bars) immunoprecipitated by anti-caveolin-1.

FIG. 3C presents photographs showing immunoblotting of caveolin-1 in CD26 (del201-211)-stimulated TT-loaded monocytes with anti-phospho-caveolin-1 or anti-Tollip antibodies, followed by stripping and reprobing with anti-caveolin-1 antibody, and photographs showing immunoblotting of monocyte lysates with anti-IRAK antibody (upper panel). Position of IRAK bands was indicated by open arrow heads, and supershifted bands of IRAK was indicated by solid arrow head. The bottom panel shows a bar graph showing the reciprocal intensities of phospho-caveolin (open bars) and Tollip (solid bars) immunoprecipitated by anti-caveolin-1.

FIG. 3D presents photographs showing THP-1 cells transfected with GFP-caveolin-1 and stained with anti-Tollip and anti-rat-Ig Texas red antibodies, and visualized by confocal laser microscopy. Bars indicate 10 μm scale.

FIG. 3E presents a photograph showing immunoblotting of endogenous caveolin-1 and endogenous Tollip with respective antibodies.

FIG. 3F presents photographs showing immunoblotting of GST-fused caveolin-1 and deletion mutants, which were incubated with THP-1 cell lysate, with anti-Tollip antibody, followed by stripping and reprobing with anti-GST antibody.

FIG. 3G schematically represents the bacterially produced GST-fused Tollip and deletion mutants. Residues 47-178 (black square) are the C2 regions (protein kinase C conserved region 2), and residues 178-274 (left gray square) are the CUE domain (ubiquitin-conjugating enzyme binding domain).

FIG. 3H presents photographs showing immunoblotting of GST-fused Tollip and deletion mutants, which were incubated with THP-1 cell lysate, with anti-caveolin-1 antibody, followed by stripping and reprobing with anti-GST antibody.

FIG. 4 shows that CD26 stimulation on TT-loaded monocytes activated NF-κB to upregulate CD86.

FIG. 4A presents graphs showing the levels of transcriptional factors activated by CD26 in the presence of TT-loaded monocytes, detected by ELISA-based DNA-binding protein assay. Binding activity was revealed by OD value at 655 nm. Data represent mean±SE from triplicate experiments. Asterisks show points of significant increase.

FIG. 4B schematically represents luciferase chimera constructs of the 5'-flanking region of human CD86 gene and deletion mutants. The two GAS elements (gamma-interferon activation sites) at −1187 and −1127 are shown by filled circle, and the two NF-κB sites at −612 and −238 are filled triangle. The position of each construct relative to the transcription start site (+1) is indicated.

FIG. 4C presents a graph showing CD86 promoter activity of luciferase chimera mutants of 5'-flanking promoter region of human CD86 after CD26-caveolin-1 interaction, detected by luciferase assay. Luciferase activity is shown as being relative to one μg of applied protein. Data represent mean±SE from triplicate experiments. Asterisks indicate points of significant increase.

FIG. 4D presents a graph showing CD86 promoter activity after interaction of caveolin-1 with various doses of CD26. Luciferase activity is shown as being relative to one μg of applied protein. Data represent mean±SE from triplicate experiments.

FIG. 5A is a photograph showing purified monocytes transfected with Texas red conjugated siRNA, using HVJ-E vector. The cells are visualized by confocal laser microscopy.

FIG. 5B presents photographs showing immunoblotting of lysates of monocytes transfected with or without sense-siRNA or mismatched siRNA, with anti-caveolin-1 antibody, followed by stripping and reprobing with anti-β-actin antibody.

FIG. 5C presents histograms showing CD86 expression in monocytes that were transfected with siRNA and treated with TT, followed by stimulation with CD26. The representative histograms are shown from 5 independent experiments. Arrowheads indicate strong positive area.

FIG. 5D presents bar graphs showing mean fluorescence intensity (MFI) of cell surface CD86 as studied in FIG. 5C. Data represent mean±SE of five independent experiments. ** indicates points of no significant change by sense siRNA, whereas * shows points of significant increase.

BEST MODE FOR CARRYING OUT THE INVENTION

Figure 1:
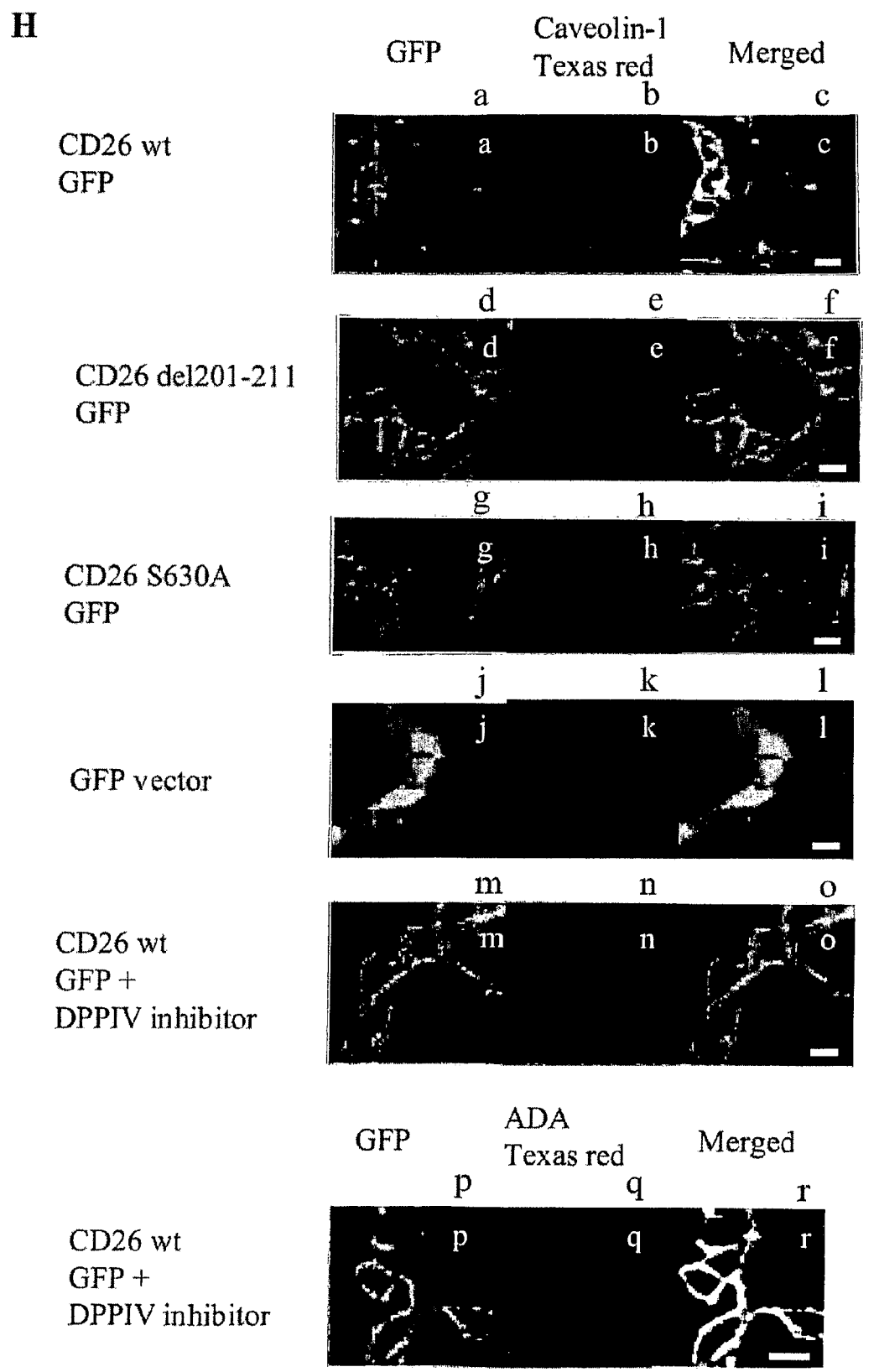
FIG. 1 shows purification and identification of CD26-binding proteins.

The following examples are presented to illustrate the present invention and to assist one of ordinary skill in making and using the same. The examples are not intended in any way to otherwise limit the scope of the invention.

Example 1

General Methods (1) Cell Lines and Isolation of Human Monocytes

HEK293 human embryonal kidney, and COS-7 monkey fibroblast cell lines were grown in Dulbecco's Modified Eagle Medium (DMEM) (Sigma-Aldrich, St. Louis, Mo.) containing 10% fetal calf serum (FCS), 100 U/ml penicillin (Life Technologies Inc., Grand Island, N.Y.) and 100 μg/ml streptomycin (Life Technologies Inc.) at 37° C., 5% $CO_2$. THP-1 human monocyte cell lines were grown in RPMI-1640 medium (Sigma-Aldrich) containing 10% FCS and penicillin-streptomycin at 37° C., 5% $CO_2$. Jurkat T cell lines with stable expression of CD26 (J.CD26) were cultured in RPMI-1640 medium containing 10% FCS and penicillin-streptomycin, containing 500 μg/ml G418 (Invitrogen, Carlsbad, Calif.) at 37° C., 5% $CO_2$, as described previously (Tanaka, et al., 1992).

Human peripheral monocytes were purified from peripheral blood mononuclear cells (PBMC), collected from healthy adult volunteers who were immunized with TT within one year before donation according to the methods described previously (Ohnuma, et al., 2001). Monocytes were cultured in Macrophage-SFM medium (Life Technologies Inc.) at 37° C., 5% $CO_2$, supplemented with penicillin-streptomycin. To avoid interference by non-specific activation of monocytes due to contamination, polymyxin B sulfate (20 IU/ml, Sigma-Aldrich) was added to all media and reagents used for APC/monocytes experiments. Purified monocytes were preincubated in the standard medium for 24 h to minimize the risk of potential interference from sCD26 present in human serum (Tanaka, et al., 1993).

(2) Antibodies and Reagents

Anti-human CD26 mouse monoclonal antibody (mAb) (1F7) was developed in the inventors' laboratory (Morimoto, et al., 1989). Anti-caveolin-1 rabbit polyclonal antibody (pAb), anti-IRAK rabbit pAb, anti-GST mAb, and Texas red-conjugated anti-immunoglobulin G (Ig) (anti-rabbit-Ig and anti-rat-Ig)) were purchased from Santa Cruz Biotechnology Inc. (Santa Cruz, Calif.). Anti-phospho-caveolin-1 mAb was obtained from BD Transduction (La Jolla, Calif.), anti-Tollip rat pAb from ALEXIS Biochemicals (San Diego, Calif.), and FITC-conjugated anti-CD86, PE-conjugated anti-CD14, Cy Chrome-conjugated anti-CD45 and isotype control mAbs were from BD PharMingen (San Diego, Calif.). Tetanus toxoid was purchased from Calbiochem (La Jolla, Calif.), and poly-L-lysine and ADA was from Sigma-Aldrich. Protein labeling with Texas red was made with FluoReporter Texas Red Protein Labeling Kit (Molecular Probes, Eugene, OG) according to the manufacturer's instruction.

(3) Constructions of Plasmids

GST-caveolin-1, HA-caveolin-1, and caveolin-1-EGFP were made by inserting caveolin-1 cDNA into pGEX6p1 (Amersham Pharmacia, Piscataway, N.J.), pCG-N-BL, and pEB6-CAG-EGFP (Tanaka, et al., 1999) vectors, respectively. A series of caveolin-1 deletion mutants were made by inserting cDNA fragments of mutated caveolin-1 generated by the polymerase chain reaction (PCR) into the respective vectors.

CD26-EGFP was made by inserting CD26 cDNA into pEB6-CAG-EGFP. Mutated CD26-EGFP constructions (del201-211) were generated by site-directed mutagenesis method, using the Gene-tailor mutagenesis kit (Invitrogen). GST-CD26 and its deletion mutants were made by inserting CD26 and its mutation cDNA into a mammalian GST expressing vector, pEBG vectors (Sanchez, et al., 1994). The inserted fragments of the deletion mutants (GST-CD26 D1, D 2, D 3) were generated by PCR, and the others (GST-CD26-del 201-211) were constructed by site-directed mutagenesis method using the Gene-tailor mutagenesis kit.

GST-Tollip, FLAG-Tollip, and VSV-IRAK-1 were made by inserting Tollip cDNA into pGEX6p1, pFLAG-CMV-2 (Sigma), and pCORON1000 VSV-G (Amersham Biosciences), respectively. The deletion mutants were constructed by inserting cDNA fragments generated by PCR.

Luciferase chimera of 5'-flanking region of human CD86 gene was generated by inserting PCR fragments of the promoter regions into Mlu I-Xho I sites of pGL3-basic vector (Promega, Madison, Wis.). PCR fragments of 5'-flanking region of human CD86 gene was made from ResGen's BAC RPC11 289N10 clone (Invitrogen) as a template with the sence oligonucleotides

```
the sense oligonucleotides
                             (SEQ ID NO:1)
5'-GGACGCGTTTTAGCATTTTGGTCTAAACTAATTTATAATTATTTAGC CTTATTTCTCCA-3' (for pGL3-Luc/1181), (SEQ ID NO:2)
5'-GGACGCGTTTGGAATTTAAAATGTTCAAAAT GATTTGT CTGGAT G-3' (for pGL3-Luc/783), (SEQ ID NO:3)
5'-GGACGCGTTTGGTTGTGGAAATTGG CAGGGTTAGGTGG-3' (for pGL3-Luc/409), (SEQ ID NO:4)
5'-GGACGCGTATTCAGGCTCATCTTAAC GTCATGTC TGG-3' (for pGL3-Luc/213)
and the antisense oligonucleotide
                             (SEQ ID NO:5)
5'-CGCTCGAGTGTGCTA GTCCCTGTTACAGCAGC-3'.
```

All constructs or cDNA fragments were confirmed by DNA sequencing.

(4) Production of GST Fusion Protein

To produce GST-Caveolin-1, GST-Tollip and their deletion mutants, the plasmid constructs were transformed into BL21 (DE3); pT-Trx E. coli (Yasukawa, et al., 1995). GST fusion proteins were induced with 0.1 mM isopropyl-β-D-thiogalactopyranoside (Amersham Pharmacia) for 10 hrs at 25° C., and purified using Glutathione Sepharose 4B FF (GSH) beads (Amersham Pharmacia).

GST-CD26 and its deletion mutants were produced by the mammalian cell line COS-7. To produce the fusion proteins, 20 μg of pEBG-CD26 or mutants vectors were transfected into $1.0 \times 10^7$ COS-7 using Lipofectamine 2000 reagent (Invitrogen), which were then grown for 24 hours and lysed on ice with lysis buffer (LB; 1% Nonidet P-40, 130 mM NaCl, 20 mM Tris-HCl (pH 8.0), 10 mM NaF, 2 mM sodium orthovanadate ($Na_3VO_4$), 1% aprotinin, 10 μg/ml leupeptin, 1 mM phenylmethylsulfonyl fluoride (PMSF), 1 mM EDTA), followed by clarification and incubation of the lysate with GSH beads at 4° C. for overnight. The beads were washed three times with LB, twice with 0.5 M LiCl, 20 mM Tris-HCl, pH 8.0, and twice with 0.5 M NaCl, 20 mM Tris-HCl, pH 8.0.

The recombinant proteins were obtained by elution from the beads with 10 mM reduced glutathione followed by dialysis in phosphate-buffered saline (PBS). Purification of full-length caveolin-1, mammalian expressed CD26 and its mutant proteins without GST were generated from GST fusion proteins using PreScission protease, followed by dialysis against PBS at 4° C. The predicted sizes of all the expressed proteins were verified by SDS-PAGE.

(5) Purification and Separation of CD26 Interacting Proteins

CD26-bound adenosine deaminase-Sepharose beads (ADA beads) were generated by the methods described previously (Tanaka, et al., 1993; Tanaka, et al., 1994). Total cell lysate of THP-1 monocytes cell lines was applied to the CD26-ADA beads columns. After extensive washes with wash buffer (50 mM Tris-HCl (pH=8.0), 1 mM EDTA, 0.1% NP-40, 50 mM NaCl, 1 mM DTT, 1 mM PMSF, 10 μg/ml aprotinin), bound proteins were eluted with high-salt buffer (10 mM Tris-HCl (pH 8.0), 1 mM EDTA, 0.1% NP-40, 1000 mM NaCl, 1 mM DTT, 0.5 mM PMSF, 10 μg/ml aprotinin).

CD26-ADA beads affinity-purified proteins were separated by SDS-PAGE and stained by silver. Peptide mass mapping was performed by recording peptide mass fingerprints of typical in-gel digests of the corresponding gel bands using MALDI-TOF MS (AXIMA-CFR plus; SHIMADZU BIOTECH, Kyoto, Japan) and subsequently searching the MASCOT database (Matrix Sciences, London, U.K.).

(6) GST Pull-down Assay

After preclearing by GST on GSH beads, J.CD26 cell lysates were incubated with GST-fused proteins on GSH beads at 4° C. for 8 h. Protein-beads complexes were washed extensively with beads with buffer (50 mM Tris-HCl (pH 8.0), 1 mM EDTA, 0.1% NP-40, 50 mM NaCl, 1 mM DTT, 1 mM PMSF), and submitted to SDS-PAGE analysis on an appropriate concentration gel under reducing condition using a mini-Protean II system (Bio-Rad Laboratories, Hercules, Calif.). Proteins were then transferred to a polyvinylidene difluoride membrane (Immobilon-P; Millipore, Bedford, Mass.). Specific antigens were probed by the corresponding mAbs, followed by HRP-conjugated anti-mouse Ig (Amersham Pharmacia). Western blots were visualized by the enhanced chemiluminescence technique (PerkinElmer Life Science, Boston, Mass.).

(7) Cell Stimulation

Freshly purified monocytes were cultured in Macrophage-SFM media for 24 h to diminish the effect of serum, and were preincubated with TT at a concentration of 0.5 μg/ml for an additional 24 h. After being washed with PBS, $1.0 \times 10^6$ of TT-loaded monocytes were stimulated for indicated periods with 0.5×06 particles of polystyrene latex beads (Molecular Probes) coated with rsCD26 wt or rsCD26 del 201-211 (1.0 µg/ml). Stimulated monocytes were subjected to confocal laser microscopy, immunoprecipitation assay, Western blotting analysis, or flow cytometry (FCM).

Freshly isolated T cells, using MACS Pan T cell isolation kit (Mitenyi Biotech, Auburn, Calif.), were cultured in 10% FCS-RPMI1640 media with PHA (10 ng/ml, Sigma-Aldrich) for 24 h. Thus, activated T cells expressing high levels of CD26 (Morimoto, et al., 1989) were subjected to cell-conjugation assay.

(8) Immunoprecipitation and Western Blot Analysis

Lysates were generated with RIPA lysis buffer (1% NP-40, 0.5% sodium deoxycholate, 0.1% SDS, 5 mM EDTA, 10 mM Tris-HCl (pH 7.4), 0.15 M NaCl, 1 mM PMSF, 0.5 mM NaF, 10 µg/ml aprotinin and 0.02 mM $Na_3VO_4$) from $1.0 \times 10^7$ of THP-1 cells incubated with recombinant soluble CD26 (rsCD26) or $1.0 \times 10^7$ of TT-loaded monocytes stimulated with rsCD26-coated beads. Then, lysates were clarified by 15,000×g for 30 min. Immunoprecipitates (IPs) were performed by incubating lysates with 2 µg of control immunoglobulins (Ig) and protein G-sepharose beads (Amersham Pharmacia) at 4° C. for 1 h. After centrifugation, supernatants were incubated with 2 µg of specific Ig at 4° C. for 2 h, followed by addition of protein G-sepharose beads for an overnight incubation. After washing four times with RIPA lysis buffer, beads were submitted to SDS-PAGE and Western blot analysis.

For studying interaction among endogenous caveolin-1, Tollip and IRAK-1 interaction, THP cells were lysed with RIPA lysis buffer (1% NP-40, 0.5% sodium deoxycholate, 0.1% SDS, 5 mM EDTA, 10 mM Tris-HCl (pH 7.4), 0.15 M NaCl, 1 mM PMSF, 0.5 mM NaF, 10 µg/ml aprotinin and 0.02 mM $Na_3VO_4$). Then, lysates were centrifuged for 30 min at 15,000×g. Immunoprecipitates (IPs) were performed by incubating lysates with 2 µg of control immunoglobulins (Ig) at 4° C. for 1 h. After centrifugation, supernatants were incubated with 2 µg of specific Ig at 4° C. for 2 h, followed by addition of protein G-sepharose beads for an overnight incubation. After washing four times with RIPA lysis buffer, beads were submitted to SDS-PAGE and Western blot analysis. For examining interacting domains with fusion proteins, COS cells ($1 \times 10^7$ cells) were transfected with 5 µg each of HA-caveolin-1, FLAG-Tollip and its deletion mutants, and VSV-IRAK-1 expressing plasmids using Lipofectamine 2000. After 24 h of transfection, cells were lysed with 500 µl of RIPA lysis buffer. Purification was performed by agitating 500 µl of the lysates with 20 µl of anti-Flag antibody M2 agarose beads (25% slurry) overnight at 4° C., washing the beads four times with RIPA buffer, and eluting the beads with 100 µl of Flag peptide (150 ng/ml). The protein beads were submitted to SDS-PAGE. Proteins were then transferred to a polyvinylidene difluoride membrane (Immobilon-P; Millipore, Bedford, Mass.). Specific antigens were probed by the corresponding mAbs, followed by HRP-conjugated anti-mouse Ig (Amersham Pharmacia). Western blots were visualized by the enhanced chemiluminescence technique (PerkinElmer Life Science, Boston, Mass.).

(9) Confocal Laser Microscopy

For fluorescent microscopy experiments using HEK293 cells, cells were preincubated in LAB-TEK 4-well chamber slide glass (Nalgen Nunc International, Naperville, Ill.) for 8 h prior to transfection. GFP fused constructs (GFP-CD26 wt, GFP-CD26 del 201-211, GFP-caveolin-1, or GFP-caveolin-1 del 82-101) were transfected with Lipofectamine 2000 reagent (Invitrogen), and 12 h later, incubated with Texas red conjugated recombinant proteins (caveolin-1 wt, caveolin-1 del 82-101, rsCD26 wt, or rsCD26 del 201-211) for 1 hr. After being washed with ice-cold PBS three times, cells were fixed in 4% paraformaldehyde in PBS, followed by mounting with Antifade Prolong kit (Molecular Probes). For blocking experiments using the competitive DPPIV inhibitor (valine-pyrrolidide (Ki=2.9 nM, IC50=13 nM), kindly provided by Japan Tobacco Inc., Tokyo, Japan), 1 µM of the valine-pyrrolidide was cultured for 15 min with HEK293 cells transfected with GFP fused constructs (GFP-CD26 wt, GFP-CD26 del 201-211, and GFP vector). After replaced fresh 10%-FCS RPMI1640 media, cells were subjected to incubation with Texas red conjugated recombinant proteins (caveolin-1 wt or ADA) for 1 h.

For T cell-APC conjugation assay as described elsewhere (Lee, et al., 2002), $1.0 \times 10^5$ of activated T cells were mixed with $1.0 \times 10^5$ of purified monocytes that had been pulsed with or without TT (0.5 µg/ml for indicated time periods), with further centrifugation. Thirty minutes later, cell mixtures were attached to microslide glass (Matsunami Glass Inc., Tokyo, Japan) coated with poly-L-lysine, and fixed with 4% paraformaldehyde in PBS for 15 min at room temperature. Cells were blocked with mouse and rabbit Ig isotypes (1 µg/ml) for 30 min at 4° C., followed by incubation with anti-CD26 mAb and anti-caveolin-1 rabbit pAb (each of 10 µg/ml) for 60 min at 4° C., then washed with ice-cold PBS twice and incubated with FITC conjugated anti-mouse Ig and Texas red conjugated anti-rabbit Ig antibodies (1:200) for 60 min at 4° C. Cells were mounted in coverslips with Antifade Prolong kit. Conjugates were first identified by direct observation under differential interference contrast and then confirmed by detecting the green fluorescence of anti-CD26 mAb in T cells and the red fluorescence of anti-caveolin-1 pAb in monocytes. The proportion of T cell-APC conjugation was calculated by random choice of 500 different cells in a coverslips from five independent experiments.

For detection of colocalization between caveolin-1 and Tollip, THP-1 cells, which were stably transfected with GFP-caveolin-1, were washed in ice-cold PBS twice, and attached to microslide glass, followed by fixation with acetone-methanol (1:1) for 2 min at room temperature. Then, cells were stained with anti-Tollip rat pAb (10 µg/ml) for 60 min at 4° C., followed by staining with Texas red conjugate anti-rat Ig antibody (1:200) for 60 min at 4° C.

For detecting the interaction among caveolin-1, Tollip, and IRAK, HEK cells were preincubated in LAB-TEK 4-well chamber slide glass (Nalgen Nunc International, Naperville, Ill.) for 8 h prior to transfection. GFP-caveolin-1, FLAG-Tollip and VSV-IRAK-1 constructs were transfected with Lipofectamine 2000 reagent (Invitrogen). 12 h later, cells were washed with ice-cold PBS 3 times, fixed in ice-cold 50% acetone in methanol, and incubated with anti-HA and anti-VSV antibodies at 4° C. for 8 h. After being washed with ice-cold 5% BSA-PBS, cells were incubated with specific second antibodies, followed by mounting with Antifade Prolong kit (Molecular Probes).

Confocal microscopy was performed with an Olympus IX70 confocal microscope with 60 objective lenses (Olympus, Tokyo, Japan), using laser excitation at 496 and 568 nm. The widths of Oregon green and Texas red emission channels were set to maximize specificity.

(10) Flow Cytometric Analysis

For assessment of cell surface caveolin-1 exposure, after purified monocytes were treated with TT (0.5 µg/ml) for 0, 6, 12, 24, and 48 h, cells were washed with ice-cold PBS three times, and stained with anti-caveolin-1 antibody (5 µg/ml) for 60 min at 4° C., followed by staining with FITC conjugated anti-rabbit Ig antibody (1:200) for 60 min at 4° C. To disturb caveolae, purified monocytes were treated with Filipin (1.0 µg/ml, Sigma-Aldrich) for 30 min at 37° C. Cells were then subjected to TT loading and to staining caveolin-1 as described above.

In experiments assessing the expression of CD86 on purified monocytes after preincubation with or without TT (0.5 µg/ml) for 24 hours, following incubation with rsCD26-coated beads for 24 h, FITC-conjugated CD86 mAb (10 µg/ml) were used with PE-conjugated anti-CD14 (10 µg/ml) and Cy Chrome-conjugated CD45 (10 µg/ml) to gate exclusively on the monocyte population. In experiments assessing the effect of siRNA against caveolin-1 in monocytes, purified monocytes were transfected with siRNA as described below, following incubation with rsCD26-coated beads for 24 h, and stained as described above.

Flow-cytometric analysis of 10,000 viable cells was conducted on Becton-Dickinson FACScalibur. Each experiment was repeated at least three times, and the results were provided in the form of a histogram of a representative experiment, or increased mean percent±standard error (SE) of mean-fluorescent intensity (MFI), compared to control or untreated cells.

(11) Small Interfering RNA (siRNA) Against Caveolin-1

To design target-specific siRNA duplexes, the present inventors selected sequences of the type AA(N19) (N, any nucleotide) from the open reading frame of human caveolin-1 (accession number=NM 001753) (Elbashir, et al., 2001). Moreover, the inventors added the sequences to the 2-nucleotide 3' overhangs of 2'-deoxythymidine (dTdT), in order to generate a symmetric duplex with respect to the sequence composition of the sense and antisense 3' overhangs. These symmetric 3' overhangs were reported to help to ensure that the siRNA were formed with approximately equal ratios of sense and antisense target RNA-cleaving siRNA (Elbashir, et al., 2001). Therefore, the present inventors selected two target sequences from 81 to 101 (ss1) and 138 to 153 (ss2) downstream of the start codon of caveolin-1 mRNA (sense1 siRNA (ss1-siRNA): 5'AACAACAAGGCCAUGG CAGACdTdT (SEQ ID NO: 6), and sense2 siRNA (ss2-siRNA): 5' AAG-GAGA UCGACCUGGUCAAC dTdT (SEQ ID NO: 7)). Moreover, mis-siRNA at 4 nucleotides was prepared to examine non-specific effects of siRNA duplexes (mis-siRNA: 5' UACAAGAAGGGCAUG GCAGACdTdT (SEQ ID NO: 8)). To visualize the efficiency of transfection, the inventors also prepared Texas red-conjugated missense siRNA (mis-siRNA-TR). These selected sequences also were submitted to a BLAST search against the human genome sequence to ensure that only one gene of the human genome was targeted. siRNAs were purchased from QIAGEN (Valencia, Calif.). Sixty pmole of siRNA duplexes were transfected into $0.5 \times 10^6$ cells, using HVJ-E vector (GenomeOne™; kindly provided by IHSIHARA SANGYO KAISHA LTD., Osaka, Japan). After 24 or 48 h of transfection, cells were prepared for examination.

(12) Small Interfering RNA (siRNA) Against Human Tollip

We selected two target sequences from 186 to 206 (ss1) and 774 to 794 (ss2) downstream of the start codon of caveolin-1 mRNA (sense1 siRNA (ss1-siRNA): 5' AAGUUGGCCAA-GAAUUACGGCdTdT (SEQ ID NO: 9), and sense2 siRNA (ss2-siRNA): 5' AACAAGGAUCCGCCAUCAACdTdT (SEQ ID NO: 10)). Moreover, mis-siRNA at 4 nucleotides was prepared to examine non-specific effects of siRNA duplexes (mis-siRNA: 5' UAGUUCGCCAAGUAUUAC-CGCdTdT (SEQ ID NO: 11)). These selected sequences also were submitted to a BLAST search against the human genome sequence to ensure that only one gene of the human genome was targeted. siRNAs were purchased from QIAGEN (alencia, CA). Sixty pmole of siRNA duplexes were transfected into $0.5 \times 10^6$ cells, using HVJ-E vector (GenomeOne™; kindly provided by IHSIHARA SANGYO KAISHA LTD., Osaka, Japan). After 48 h of transfection, cells were prepared for examination.

(13) Luciferase Assay

HEK 293 cells were plated on 6-cm diameter culture dishes (BD Bioscience, La Jolla, Calif.) to 30-50% confluence, and cell culture medium was replaced with Opti-MEM medium (Invitrogen) before transfection. Plasmid mixture was mixed with Lipofectamine 2000 transfection reagent and added to the culture. Total amount of the plasmids was kept constant by adding an irrelevant plasmid. After 6 h of incubation, the medium was replaced with fresh DMEM supplemented with 10% FCS, and the cells were further cultured in the presence or absence of various reagents for 24 h at 37° C. Luciferase enzyme activity was determined using a luminometer (Promega), and relative light units were normalized to the protein amount determined with protein assay reagent according to the manufacturer's instructions (Pierce Biotechnology, Rockford, Ill.) (Makino, et al., 1996).

(14) Nuclear Protein Extraction and DNA-binding Protein Assay

Nuclear protein extraction (NE) was obtained with Trans-Factor Extraction Kit (Clontech, Palo Alto, Calif.) from purified monocytes which were treated with TT, followed by rsCD26 stimulation. Each 6 µg NE (with or without the specific competitor oligonucleotides (500 ng)) was subjected to ELIZA-based DNA-binding protein assay, using Mercury TransFactor Kit (Clontech). DNA-binding protein activity was measured by the absorbance value at 655 nm with microtiter plate reader (Bio-Rad) with reference at 405 nm.

(15) Two-dimensional Polyacrylamide Gel Electrophoresis (2D-PAGE)

Membrane fraction from monocytes was extracted with ReadyPrep Protein Extraction Kit (Bio-Rad) according to the manufacturer's instruction. Then, membrane proteins were cleaned up to pellets with 2D Clean-up Kit (Bio-Rad) and were resuspended in rehydration lysis buffer (RHB; 8 M urea, 2 M thiourea, 4% CHAPS, 50 mM dithiothreitol, 0.5% ZOOM carrier ampholyte (pH range 3-10) (Invitrogen), 0.002% bromphenol blue) to a final concentration of 1 mg/ml. Wide range immobilized pH gradient (IPG) strips, pH 3-10 (Invitrogen), were rehydrated in 155 µl RHB containing 10 µg protein, and isoelectric focused for 1367 Vh on a ZOOM IPGRunner System (Invitrogen). Second dimension SDS-PAGE was performed using 4-12% NuPAGE Bis-Tris gels (Invitrogen). Analytical gels were stained with SilverQuest Silver Staining Kit (Invitrogen). Peptide mass mapping was performed by recording peptide mass fingerprints of typical in-gel digests of the corresponding gel bands using MALDI-TOF MS (AXIMA-CFR plus; SHIMADZU BIOTECH, Kyoto, Japan) and subsequently searching the MASCOT database (Matrix Sciences, London, U.K.).

(16) T Cell Proliferation Assay

Freshly isolated monocytes ($0.5 \times 10^6$/well) were transfected with siRNAs, preincubated with 0.5 µg/ml of TT for 16 hours, followed by 24-hour incubation with srCD26 (0.5 µg/ml). After washing with PBS, $1.0 \times 10^4$/well of the preincubated monocytes were then subjected to the assay with $1 \times 10^5$/well of purified T cells from the same donor. Proliferation of cells was monitored in all instances by measuring BrdU incorporation by ELIZA BrdU Kit (Roche) on day 7 of culture. Degree of proliferation is indicated as cpm in the ordinate. The experiments represent mean values±standard error calculated from 5 independently performed experiments.

(17) Statistics

Student's t test was used to determine whether the difference between control and sample was significant (p<0.05 being significant).

Example 2

Identification of CD26 Binding Protein

To identify CD26-interacting proteins in monocytes, the present inventors generated CD26-bound affinity columns with ADA-sepharose, since ADA is a CD26-binding protein (Kameoka, et al., 1993). Cellular extracts from the monocyte cell line THP-1 were applied to this CD26-ADA sepharose column. After vigorous washing, bound proteins were eluted using highly concentrated salt buffer. These proteins were then subjected to SDS-PAGE analysis. Non-specific multiple bands were found in lanes of lysate, elution of ADA (mock) column, and washout solution after eluting through CD26-ADA columns (lanes 1-3 in FIG. 1A). On the other hand, three major bands were revealed in the elution of CD26-ADA columns (lane 4 in FIG. 1A). The protein bands specifically bound to CD26 on ADA columns were subjected to peptide mass fingerprinting by matrix assisted laser desorption ionization time-of-flight mass spectrometry (MALDI-TOF MS). With searching of the MASCOT database, obtained masses and apparent molecular weights of the different polypeptides revealed that the fraction eluted from CD26-ADA sepharose columns contained three major bands, and these bands were determined to be CD26, ADA and Caveolin-1 (FIG. 1A). Since CD26-ADA beads were generated with passive conjugation, CD26 and ADA in the elution fraction might be contaminated from column beads. Caveolin-1 at approximately 20-25 kDa was strongly stained with silver in the elution fraction (lane 4), and was not detected specifically in the fraction through the mock ADA beads column (lane 2). These findings suggested that caveolin-1 was associated with the CD26 molecule.

To confirm the interaction between CD26 and caveolin-1 in living cells, coimmunoprecipitation experiments were performed. THP-1 cells cocultured with soluble CD26 (sCD26) were immunoprecipitated (IP) with either anti-caveolin-1 or anti-CD26 antibodies. Immune complexes were resolved by SDS-PAGE and immunoblotted with anti-CD26 or anti-caveolin-1. Membranes were stripped and reprobed with the indicated antibodies. CD26 was detected by its specific antibody in lysates coimmunoprecipitated with caveolin-1 specific antibody (left panel of FIG. 1B). Endogenous caveolin-1 was detected in THP-1 (lower of left panel in FIG. 1B). Caveolin-1 was detected specifically with Western blots of lysates coimmunoprecipitated with CD26 specific antibody (upper of right panel in FIG. 1B). Endogenous CD26 was not detected in THP-1 (lower of right panel in FIG. 1B). Thus, the above results showed that caveolin-1 is the binding protein to CD26 in THP-1.

To determine the binding domain of caveolin-1 to CD26, we performed a GST pull-down assay using a series of GST-fused deletion mutants of caveolin-1 (FIG. 1C), and CD26 transfected Jurkat T cells (J.CD26). GST-fused caveolin-1 and its mutants on glutathione sepharose (GSH) beads were incubated with J.CD26 cell lysate after preclearing with GST on GSH beads. Bound proteins and 1% amount of input lysate were resolved by SDS-PAGE and immunoblotted with anti-CD26 antibody, followed by stripping and reprobing with anti-GST antibody. As shown in FIG. 1D, CD26 was co-precipitated with GST-Cav-1 wt, Cav-1 (1-101), and Cav-1 (82-178), but not with GST-Cav-1 (1-82), Cav-1 (102-178) and Cav-1 (del82-101), indicating that residues 82-101 of caveolin-1 is the binding domain to CD26. This domain is known as the scaffolding domain (SCD) of caveolin-1 (Smart, et al., 1999). To confirm these findings in living cells, we constructed GFP-fused full-length caveolin-1 and caveolin-1 lacking the scaffolding domain (del 82-101). After the GFP-fused caveolin-1 and its mutant were transfected into HEK293 cells, which expressed neither CD26 nor caveolin-1, Texas red conjugated CD26 (sCD26-TR) was added to the transfectants. Full-length caveolin-1-GFP, which was detected in surface membrane and perinuclear area (FIG. 1E-a), was clearly merged with sCD26-TR (FIG. 1E-b, c). On the other hand, since caveolin residues 61-101 was demonstrated to be necessary for oligomerization (Smart, et al., 1999), caveolin (del 82-101)-GFP lacking its scaffolding domain was localized diffusely (FIG. 1E-d), and showed no evidence of interacting with sCD26-TR (FIG. 1E-e, f). Although CD26-TR was slightly detected in HEK293 cells transfected with GFP alone (FIG. 1E-g, h), CD26-TR was not associated with GFP (FIG. 1E-i).

To determine the region(s) in CD26 responsible for binding to caveolin-1, we performed a GST-pull down assay using a series of GST-fused deletion mutants of CD26 produced by COS-7 cells (FIG. 1F). To preserve the natural composition of CD26, we constructed a series of GST-fused deletion mutants of CD26 expressed in COS cells, using GST-fused proteins vector expressed in mammalian cells (Sanchez, et al., 1994). GST-fused CD26 and deletion mutants on GSH beads were incubated with THP-1 cell lysate after preclearing with GST on GSH beads. Bound proteins and 1% amount of input lysate were resolved by SDS-PAGE and immunoblotted with anti-caveolin-1 antibody, followed by stripping and reprobing with anti-GST antibody. As shown in FIG. 1G, caveolin-1 was co-precipitated with GST-CD26 wt, and CD26 D3 (residues 31-429), but did not coprecipitate with GST-CD26 D1 (residues 507-766), CD26 D2 (residues 267-584), and CD26 del 201-211. These results suggested that amino acids 201-211 of CD26 were required for binding of CD26 to caveolin-1. This region in CD26 contains a caveolin-binding consensus motif (CBD) (ϕXϕXXXXϕXXϕ; ϕ and X depict aromatic residue and any amino acid, respectively) (Smart, et al., 1999), specifically W<u>V</u>Y<u>EEE</u>EVFSA<u>Y</u> (SEQ ID NO: 12) (Tanaka, et al., 1992). Our previous report revealed that DPPIV enzymatic activity of CD26 was necessary to exert activation effect of TT-loaded monocytes (Ohnuma, et al., 2001). In this regard, caveolin-1 was not detected in complexes with GST-CD26 S630A, with DPPIV enzymatic activity being deleted (FIG. 1G). To confirm these findings in living cells, we constructed GFP-fused full-length CD26, mutant lacking CBD (del 201-211) and mutant lacking DPPIV enzymatic activity (S630A). After the GFP-fused CD26 and mutants were transfected into HEK293 cells, Texas red conjugated caveolin-1 (cav-TR) was added to the transfectants. CD26 wt-GFP, CD26 del201-211-GFP and CD26 S630A-GFP were localized in cell surface membrane (FIGS. 1H-a, d, g). Cav-TR was colocalized in HEK293 cells transfected with CD26-wt-GFP (FIGS. 1H-b, c). In CD26 (del201-211) as well as CD26 S630A-GFP transfected cells, however, cav-TR was not detected (FIGS. 1H-e, f, h, i). Cav-TR was not observed in HEK293 cells transfected with GFP alone (FIGS. 1H-j, k, l). To confirm the role of DPPIV active site in binding of CD26 to caveolin-1, we used the competitive inhibitor of DPPIV, valine-pyrrolidide (Val-Pyr). After GFP-CD26 wt transfected HEK293 cells were treated with Val-Pyr (FIG. 1H-*m*), cav-TR was added to the cells. Cav-TR was not observed in HEK293 cells transfected with GFP-CD26 wt after treatment with Val-Pyr (FIGS. 1H-*n*, *o*). To confirm CD26 binding activity other than DPPIV-related molecules, Texas red conjugated ADA was added to HEK293 cells transfected with GFP-fused wild type CD26 (wt) which were incubated with Val-Pyr (p-r). Since the binding of Texas red conjugated-ADA to CD26 was observed in HEK293 cells transfected with GFP-CD26 wt after treatment with Val-Pyr (FIGS. 1H-*p*, *q*, *r*), Val-Pyr did not change the nature of the transfectants as well as the binding activity of CD26. Taken together, CD26 is demonstrated to bind to caveolin-1 through CBD as well as the serine residue 630 in CD26 and the scaffolding domain in caveolin-1.

Example 3

CD26 on T Cells Interacts with Caveolin-1 on Monocytes

Caveolin-1 was demonstrated to be localized to the cytoplasmic membrane inner layer, toward the cytosolic side (Smart, et al., 1999). The inventors previously showed that rsCD26 upregulated CD86 on monocytes only after treatment with the recall antigen tetanus toxoid (TT) (Ohnuma, et al., 2001). Since TT was reported to be taken up by antigen presenting cells (APC) through caveolae (Montesano, et al., 1982; Pelkmans, et al., 2002), we examined a flip-flop event of caveolin-1 in monocytes after treatment with TT. After purified monocytes were incubated with or without TT for the indicated time periods in FIG. 2B, cell surface caveolin-1 was stained with anti-caveolin-1 antibody detecting the N terminal region, followed by staining with anti-rabbit Ig FITC, and analyzed for % positive cells by flow cytometry. Caveolin-1 was detected on cell surface of monocytes 12-24 hours after treatment with TT (FIG. 2A). On the other hand, caveolin-1 on untreated monocytes was not detected after 0-48 hours of culture. To further examine TT effect on caveolae, monocytes were treated with Filipin, which inhibits caveolae trafficking by dispersing cholesterol in cell membrane (Peiro, et al., 2000). Purified monocytes were preincubated with Filipin for 30 min, followed by incubation with or without TT for the indicated time periods, and then cell surface caveolin-1 was detected by the same method as described above. As shown in FIG. 2A, caveolin-1 was not detected on monocytes treated with Filipin, even after TT was loaded. These data demonstrated that certain populations of TT-loaded monocytes were found to express caveolin-1 on cell surface.

Since $CD26^{high}$ T cells strongly responded to memory antigens such as TT (Morimoto, et al., 1989), and activated $CD26^{high}$ T cells are accumulated in the inflammatory regions (Morimoto, et al., 1998; von Bonin, et al., 1998), the inventors hypothesized that activated memory T cell-antigen-loaded monocytes interacted directly via surface expressed CD26 on T cells and caveolin-1 on monocytes. To further characterize these points, we examined potential colocalization of CD26 and caveolin-1 in T cell-monocyte contact site. For this purpose, activated peripheral T cells were mixed with TT-loaded monocytes, and conjugate formation was then initiated by centrifuging these cell mixtures. Thirty minutes later, cells were prepared for confocal laser microscopy as described in Example 1. First, without centrifugation after mixing, activated T cells and TT-loaded monocytes were attached to coverslips, fixed without permeabilization, stained with anti-CD26 (FITC) and anti-caveolin-1 (Texas red) antibodies. In these experiments, CD26 was detected exclusively on activated T cells (FIG. 2B *a*), and cell surface caveolin-1 was detected exclusively on TT-loaded monocytes (FIG. 2B *b*, *c*). These results are consistent with previous report showing that T cells did not express caveolin-1 (Galbiati, et al., 2001) and resting monocytes did not express CD26 (Morimoto, et al., 1989). To form cell-cell conjugation, activated T cells and 24-hour TT-loaded monocytes were mixed, followed by centrifugation. Following incubation for 30 min, conjugates were attached to coverslips, fixed without permeabilization, stained with anti-CD26 (FITC) and anti-caveolin-1 (Texas red) antibodies. CD26 and caveolin-1 were recruited in the contact area of activated T cells and TT-loaded monocytes (FIG. 2C-*a* to *i*). Quantification of cell conjugation between T cells and monocytes was performed as follows. After purified monocytes were incubated with or without TT for the indicated time periods in FIG. 2D, T cell-monocyte conjugation was formed and stained as described in Example 1. For inhibition study of caveolae formation, purified monocytes were preincubated with Filipin for 30 min, followed by incubation with or without TT for the indicated time periods, and then subjected to T cell-monocyte conjugation assay by the same method as described above. The results are shown in FIG. 2D. As shown in caveolin-1 expression study (FIG. 2A), conjugation formation of activated T cells and TT-loaded monocytes was increased in monocytes with TT loaded for 12-24 hrs (solid circle in FIG. 2D). Cell conjugation was not detected in TT-untreated monocytes or with Filipin-treated monocytes (open circle, solid triangle, and open triangle in FIG. 2D). These data suggested that memory CD26+ T cells interacted with antigen-loaded monocytes through interaction of CD26 on T cells and caveolin-1 expressed on monocytes.

Example 4

Phosphorylation of Caveolin-1 Leads to Signal Transduction in Monocytes

The present inventors focused on caveolin-1-mediated signal transduction events and determined whether such events upregulate CD86 expression following CD26 binding to caveolin-1 on TT-loaded monocytes. To stimulate TT-loaded monocytes with CD26, we used CD26 coated polystyrene latex beads to mimic the physiological interaction of CD26 expressed on peripheral T cells and TT-loaded monocytes. TT-loaded monocytes were incubated with polystyrene latex beads coated with wild type CD26 (wt) or deletion mutant CD26 lacking the CBD (del201-211). After attachments to coverslips, conjugates were fixed without permeabilization and stained with anti-caveolin-1 antibody, followed by staining with anti-rabbit Ig FITC antibody. Cells and beads were visualized by confocal laser microscopy. FIG. 3A-*a* shows that beads coated with wild type CD26 engaged caveolin-1 on TT-loaded monocytes, whereas beads coated with mutant CD26 lacking CBD did not alter caveolin-1 expression on TT-loaded monocytes (FIG. 3A-*b*). It is reported that in signaling events via caveolin-1, phosphorylation of caveolin-1 was implicated (Smart, et al., 1999). For this purpose, at various time periods following stimulation of TT-loaded monocytes by these beads, cell lysates were prepared for analysis. Cell lysates were immunoprecipitated (IP) with anti-caveolin-1 antibody, and immune complexes were resolved by SDS-PAGE, immunoblotted with anti-phospho-caveolin-1 or anti-Tollip antibodies, followed by stripping and reprobing with anti-caveolin-1 antibody. Total cell lysates were also resolved by SDS-PAGE, immunoblotted with anti-IRAK antibody. 0.5-10 minutes following stimulation with CD26 wt-coated beads, caveolin-1 was phosphorylated (FIG. 3B), and the changes in intensity were shown as a bar graph in the bottom panel of FIG. 3B. The signaling cascade leading to CD86 upregulation appears to involve a number of proteins, such as MyD88, IRAK, and Tollip (Medzhitov, 2001). MyD88 and IRAK contain the Toll-IL-1-receptor domain and the death domain for interacting with each other or the IL-1 receptor or Toll-like receptor (Medzhitov, 2001). Tollip contains a C2 domain (Protein kinase C conserved region 2), which was predicted, but not yet clearly demonstrated, to be associated with membrane lipids (Burns, et al., 2000). The C2 domain is a region containing approximately 130 residues involved in binding phospholipids in a calcium dependent manner or calcium independent manner. C2 domains are found in over 100 different proteins with functions ranging from signal transduction to vesicular trafficking. Calcium binding to the C2 domain of synaptotagmin induces little conformational change in the C2 domain, but calcium induces a change in the electrostatic potential to enhance phospholipid binding, suggesting the C2 domain functions as an electrostatic switch. In addition to electrostatic interactions, side chains in the calcium binding loops influence the binding of different C2 domains to either neutral or negatively charged phospholipids. Tollip C2 domain was not reported to be associated with calcium dependent action in the IL-1 receptor or Toll-like receptor signaling (Medzhitov, 2001). We therefore examined the potential involvement of these proteins in signaling cascade via CD26-caveolin-1 interaction. As shown in FIG. 3B, Tollip was found in IP complexes with caveolin-1 pAb, and released from caveolin-1 2-5 minutes after CD26-caveolin-1 interaction (between 2 to 5 min, Tollip was not detected in IP complex with caveolin-1 pAb). At these time points, IRAK showed hyperphosphorylation (FIG. 3B) by Western blot analysis. It should be noted that neither MyD88 nor IRAK-4 was observed in the complexes (data not shown). On the other hand, caveolin-1 was not phosphorylated after stimulation with mutant CD26 (del201-211) beads, nor release of Tollip, nor shift of IRAK (FIG. 3C). These results suggested that the Tollip-IRAK cascade was triggered by CD26-caveolin-1 interaction.

Previous reports demonstrated that Tollip was present in a complex with IRAK, and that recruitment of Tollip-IRAK complexes to the activated IL-1 receptor or Toll-like receptor complexes led to activation of NF-κB (Cao, et al., 1996; Burns, et al., 2000). The above results suggested that Tollip in monocytes was present in a complex with caveolin-1. We next examined in detail the association between caveolin-1 and Tollip. IP study in monocytes shown in FIGS. 3B and C revealed that caveolin-1 was associated with Tollip. In living cells, Tollip was partially colocalized with caveolin-1 in THP-1 cells transfected with GFP-fused caveolin-1, especially in surface membrane (FIGS. 3D-a, b, and c). Endogenous caveolin-1 was detected by its specific antibody in THP-1 cell lysates coimmunoprecipitated with a Tollip specific antibody (left panel in FIG. 3E). Endogenous Tollip was also detected by anti-Tollip antibody in THP-1 cell lysates coimmunoprecipitated with caveolin-1 specific antibody (right panel in FIG. 3E). These results indicate that caveolin-1 on monocytes associates with endogenous Tollip in THP-1 cells.

To further determine the binding domains of Tollip-caveolin-1 complexes, we performed a GST-pulldown assay using a series of GST-fused caveolin-1 and GST-fused Tollip mutants (FIGS. 1C and 3F). GST-fused caveolin-1 and deletion mutants on GSH beads were incubated with THP-1 cell lysate after preclearing with GST on GSH beads. Bound proteins and 1% amount of input lysate were resolved by SDS-PAGE and immunoblotted with anti-Tollip antibody, followed by stripping and reprobing with anti-GST antibody. Similarly, using GST-fused Tollip and deletion mutants on GSH beads, immunoblotting with anti-caveolin-1 antibody was performed. As shown in FIG. 3F, Tollip was coprecipitated with GST-Cav-1 wt, Cav-1 (1-101), and Cav-1 (82-178), implying that the scaffolding domain of caveolin-1 (residues 82-101) was required for binding to Tollip. As shown in FIG. 3H, caveolin-1 was coprecipitated with GST-Tollip wt, Tollip (47-274), Tollip (1-178), and Tollip (47-178). These results revealed that the C2 domain of Tollip (residues 47-178) was associated with caveolin-1 interaction. Taken together, after ligation of caveolin-1 on TT-loaded monocytes by binding of CD26, caveolin-1 was phosphorylated and released Tollip, associated with phosphorylation of IRAK in monocytes.

Example 5

NF-κB Activation is Required for CD86 Upregulation after CD26-caveolin-1 Interaction The data above suggested that IRAK might play a role in CD86 upregulation in monocytes as a downstream event of CD26-caveolin-1 interaction. Previous studies reported that IRAK phosphorylation was associated with TRAF6 to induce activation of NF-κB, JNK (c-Jun N-terminal kinase) and p38 MAP kinase (Cao, et al., 1996). We next identified the transcriptional factors activated by CD26 in the presence of TT-loaded monocytes. TT-loaded monocytes were stimulated with CD26-coated beads for 2 hours or PMA, and harvested for extraction of nuclear proteins (NE). Each 6 µg of NE with or without the specific competitor oligonucleotides was subjected to ELIZA-based DNA-binding protein assay. In this experiment, we detected significant levels of p50 and p65 NF-κB components in nuclear extracts of TT-loaded monocytes stimulated with wild type CD26 (right panel of FIG. 4A). The increase in p50 and p65 NF-κB levels was inhibited by the specific competitor oligonucleotides (left panel of FIG. 4A). Levels of AP-1 (c-Fos and c-Jun) and STAT1 were not detected in nuclear extracts of TT-loaded monocytes stimulated with wild type CD26 (FIG. 4A). These results suggested that NF-κB was activated via IRAK phosphorylation after Tollip was released from caveolin-1. We next examined whether NF-κB binding sites were required in the human CD86 promoter regions for activation, since previous reports revealed that GAS elements (gamma-interferon activation sites) and NF-κB binding sites were present and required for activation of CD86 transcription (Li, et al., 1999). For this purpose, we constructed a series of luciferase chimera mutants of 5'-flanking promoter region of human CD86 (FIG. 4B). Using these luciferase mutants, we tested CD86 promoter activity after CD26-caveolin-1 interaction. Twelve hrs after HE 93 cells were cotransfected with CD86-promoter luciferase constructs and wild type caveolin-1 expressing vectors, wild type soluble CD26 (rsCD26 wt) or mutant rsCD26 del 201-211, lacking 201-211 residues, was added to the culture media, and incubated for an additional 20 hrs. Cells were harvested for measurement of luciferase activity and protein concentration. In the same manner, luciferase assay was performed using HEK293 cells cotransfected with pGL3-Luc/1181 or pGL3-Luc/basic, and wild type caveolin-1 expressing vectors, various concentrations of wild type soluble CD26 (rsCD26 wt) or mutant rsCD26 del 201-211, lacking 201-211 residues. In the presence or absence of GAS elements (pGL3-Luc/1181 and pGL3-Luc/783), luciferase activity was not affected following stimulation of TT-loaded monocytes with CD26 (FIG. 4C). On the other hand, two NF-κB binding sites in the promoter regions were required for activation of CD86 transcription following CD26 treatment in caveolin-1 expressed HEK293 cells (FIG. 4C). In contrast, significant activity in single NF-κB luciferase construct (pGL3-Luc/409) was not detected (FIG. 4C). It should be noted that no significant activity in NF-κB luciferase was observed in cells treated with rsCD26 or cells with caveolin-1 alone. Moreover, an enhancement in luciferase activity was observed with increasing doses of rsCD26 wt in HEK293 cells transfected with pGL3-Luc/1181 and caveolin-1 (FIG. 4D). This dose dependent luciferase activity was not observed following stimulation with CD26 del201-211. These results showed that NF-κB activation downstream of caveolin-1 resulted in the upregulation of CD86 in TT-loaded monocytes stimulated with CD26.

Figure 5:
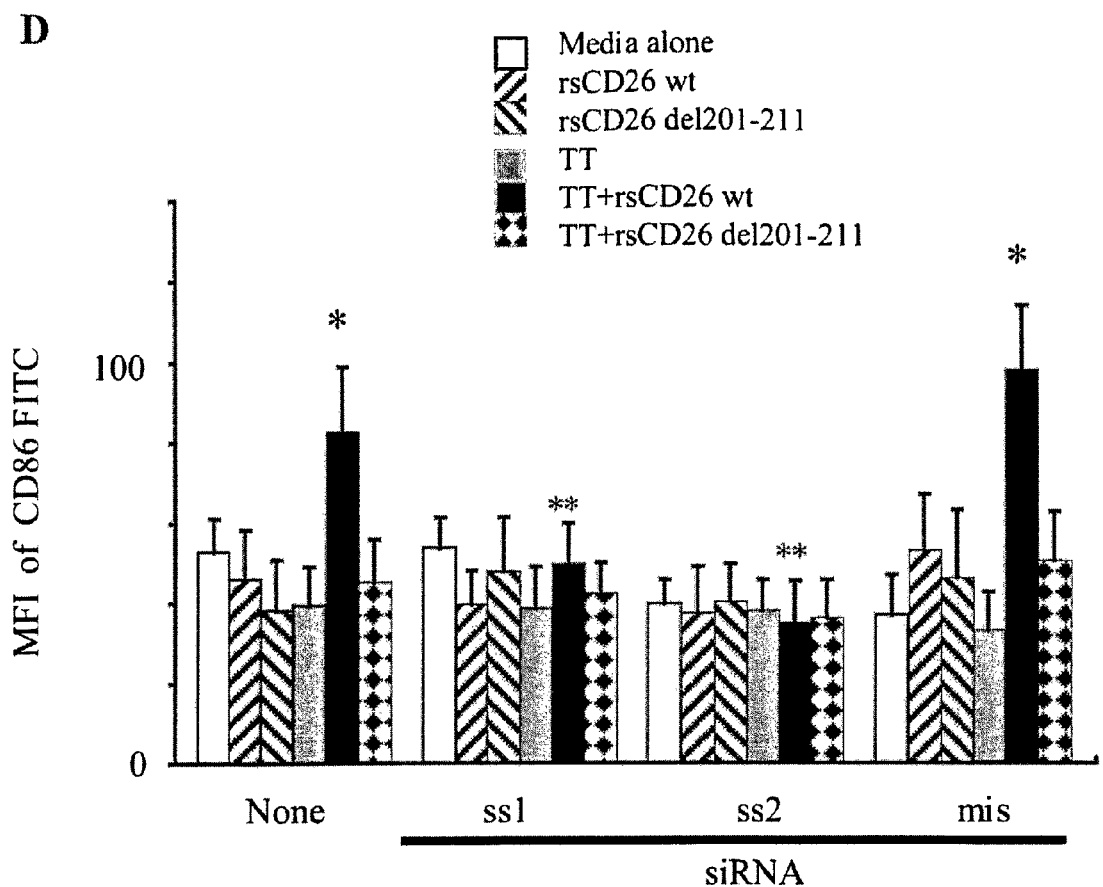
FIG. 5 shows that siRNA against caveolin-1 inhibited effect of CD26 on CD86 upregulation in TT-loaded monocytes.
Figure 6:
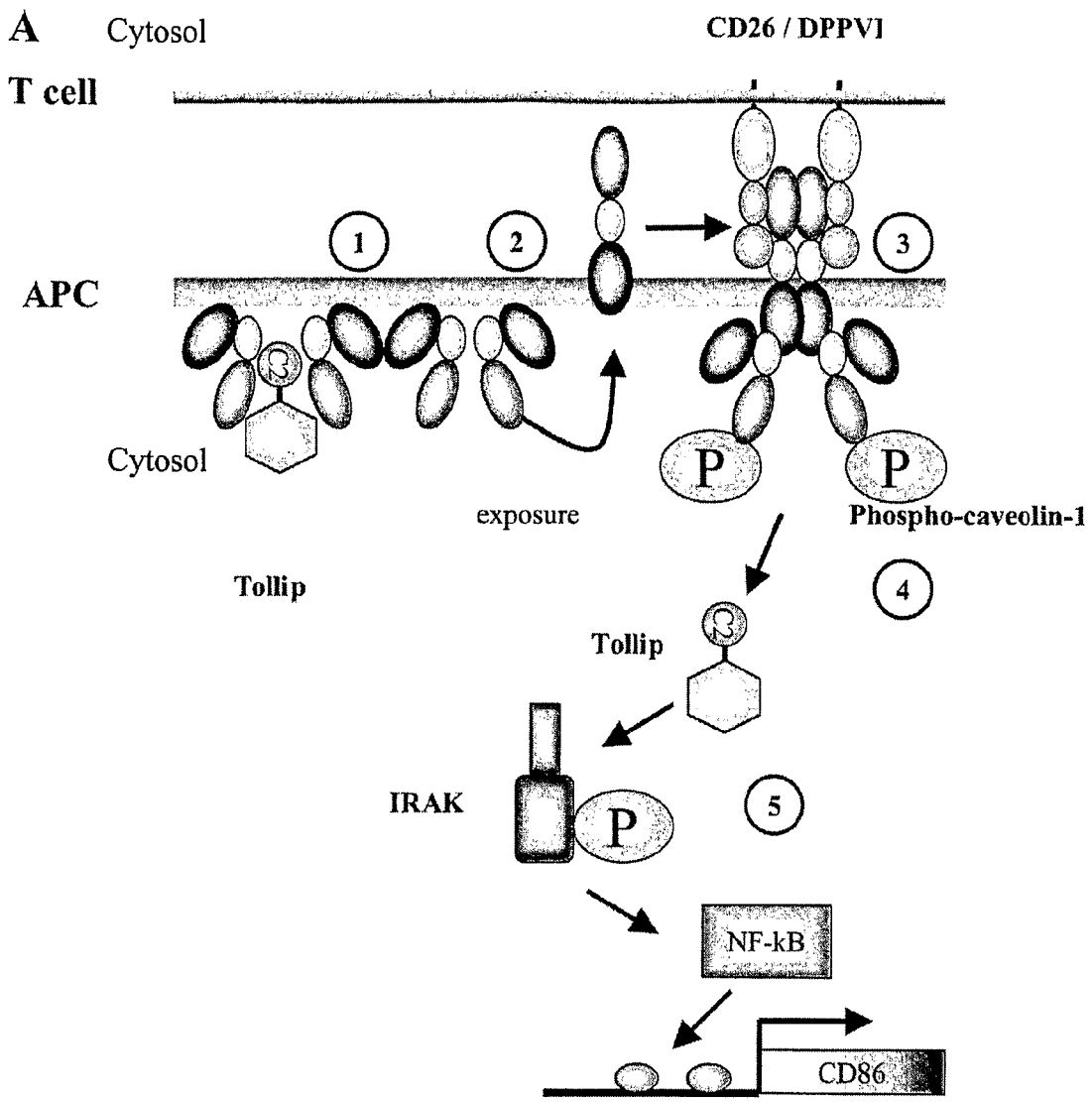
FIG. 6A shows model for CD26-caveolin-1 interaction leading to immune enhancement. (1) Caveolin-1 in monocytes (APC) resides at the inner membrane with or without Tollip presence. (2) After uptake of tetanus toxoid into monocytes via caveolae, some population of caveolin-1 flip-flop to be exposed on the outer cell surface of TT-loaded monocytes. (3) Migration of CD26 positive activated T cells to areas of antigen-loaded APCs results in contact with TT antigen-presenting APC and formation of immunological synapse, leading to association of CD26 and caveolin-1. Caveolin-1 is aggregated in contact area, followed by its phosphorylation. (4) Phosphorylated caveolin-1 (phospho-caveolin-1) releases complexed Tollip, presumably due to conformational changes, and Tollip in the cytosol then interacts with IRAK. (5) After IRAK is phosphorylated, NF-κB is activated to lead to upregulation of CD86.
FIG. 6B shows T cell-APC local interaction and immune response. (1) entry of recall antigens via caveolae into APC leads to presentation of antigen peptides on MHC class II molecules and exposure of caveolin-1. (2) Through formation of mature immunological synapse, APC stimulates memory T cell through TCR and costimulatory molecules such as CD86/CD80-CD28. At one time, caveolin-1 on APC is associated with CD26 on memory T cell, and CD86 is upregulated in APC and memory T cell is activated via CD26 costimulatory effect. (3, 4) CD86 upregulation results in greater T cell-APC interaction, which then leads to the development of memory activated T cells locally and activated immune response, resulting in potential autoimmune diseases, etc.
Figure 6:
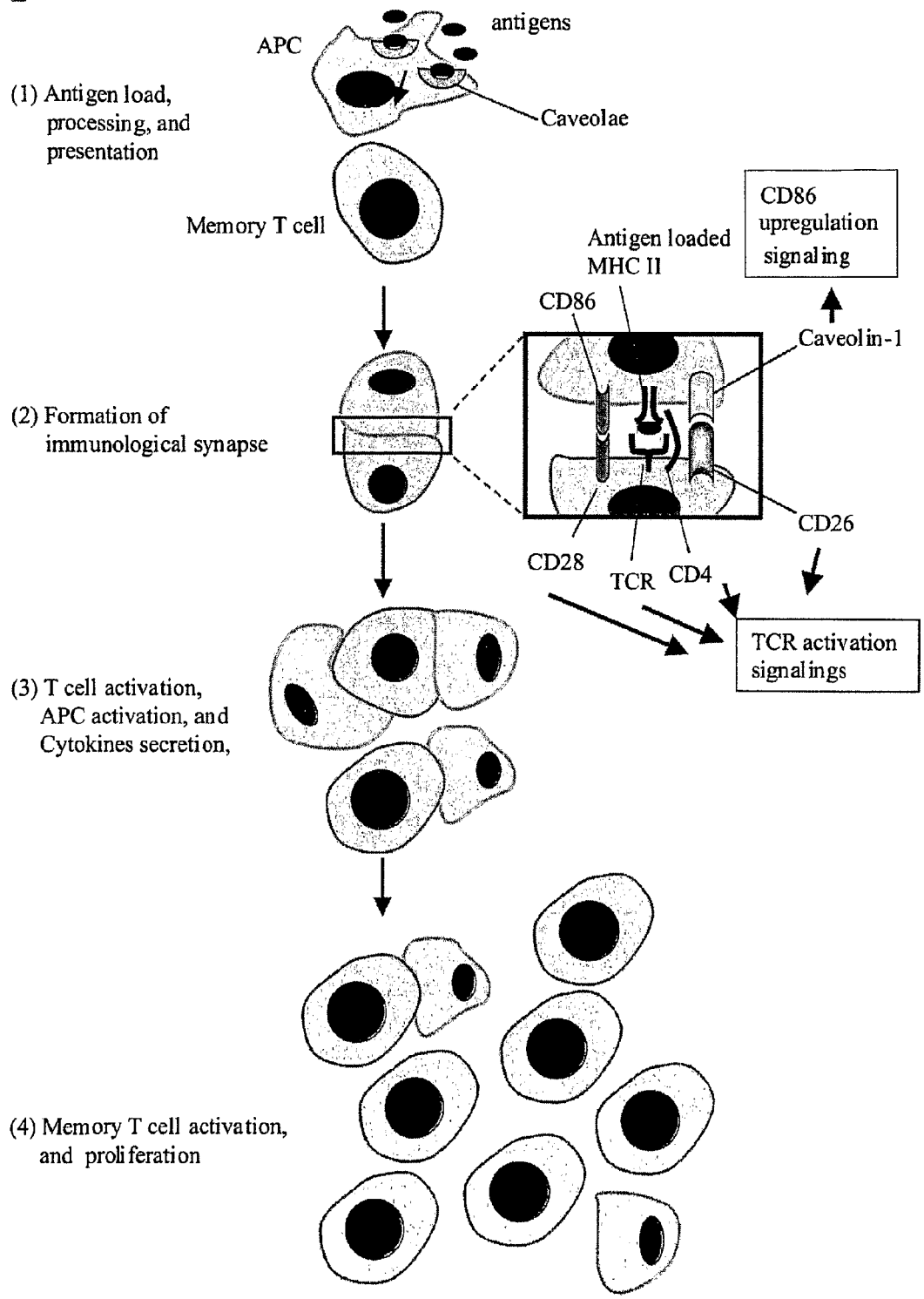

Example 6 siRNA Against Caveolin-1 in Monocytes Attenuates Upregulation of CD86 by CD26 Treatment To examine CD26-caveolin-1 interaction and its functional consequences more directly, we performed siRNA experiments utilizing freshly isolated monocytes. We first tested whether siRNA was successfully transfected into primary monocytes. Purified monocytes were transfected with Texas red conjugated mismatched siRNA (siRNA-TR), using HVJ-E vector. After 24 hrs of transfection, cells were attached to coverslips, fixed, stained with anti-CD14-FITC, and visualized by confocal laser microscopy. As shown in FIG. 5A, more than 95% of monocytes were transfected with siRNA-TR, using HVJ-E (Hemagglutinating Virus of Japan Envelope) vector and centrifugation method. We next examined by Western blot analysis whether siRNA against caveolin-1 was effective in knocking down caveolin-1 protein levels in transfected monocytes. We prepared 2 sets of specific siRNA against caveolin-1 (ss1 is targeted for +81 to +101 of caveolin-1 gene and ss2 for +138 to +158) as described in Example 1. Purified monocytes were transfected with or without sense-siRNA as described above or mismatched siRNA, using HVJ-E vector. 48 hrs later after transfection, cell lysates were prepared, resolved by SDS-PAGE, immunoblotted with anti-caveolin-1 antibody, followed by stripping and reprobing with anti-β-actin antibody. As shown in FIG. 5B, both of these siRNA effectively knocked down caveolin-1 expression in monocytes. Since caveolin-1 in monocytes was not significantly knocked down by mismatched siRNA or HVJ-E vector alone, this inhibitory effect by siRNA was specific. We next examined whether CD26 exerted its effect in monocytes in which caveolin-1 expression was knocked down by siRNA. Purified monocytes were transfected with or without siRNA using HVJ-E vector, followed by treatment with TT. After stimulation with CD26-coated beads, cells were subjected to analysis of surface CD86 expression by FCM. Monocytes were identified by gating of CD45-Cy Chrome and CD14-PE positive population. CD86 was upregulated among a significant population of TT-loaded monocytes stimulated with CD26 wt-coated beads (right of upper panels in FIG. 5C). On the other hand, sense siRNA (ss1 and ss2) inhibited this effect on CD86 upregulation in TT-loaded monocytes (middle and right of lower panels in FIG. 5C). Mismatched siRNA did not exhibit this inhibitory effect (left of lower panel in FIG. 5C). Changes in CD86 expression were clearly demonstrated in FIG. 5D, demonstrating that knockdown of the caveolin-1 expression resulted in the inhibition of CD86 upregulation in TT-loaded monocytes stimulated with CD26 (* and ** in FIG. 5D). These results suggested that caveolin-1 played an important role in signal transduction following CD26 binding to TT-loaded monocytes, leading to the upregulation of CD86 in monocytes.

Example 7

Interaction Among Caveolin-1, Tollip, and IRAK-1

Figure 7:
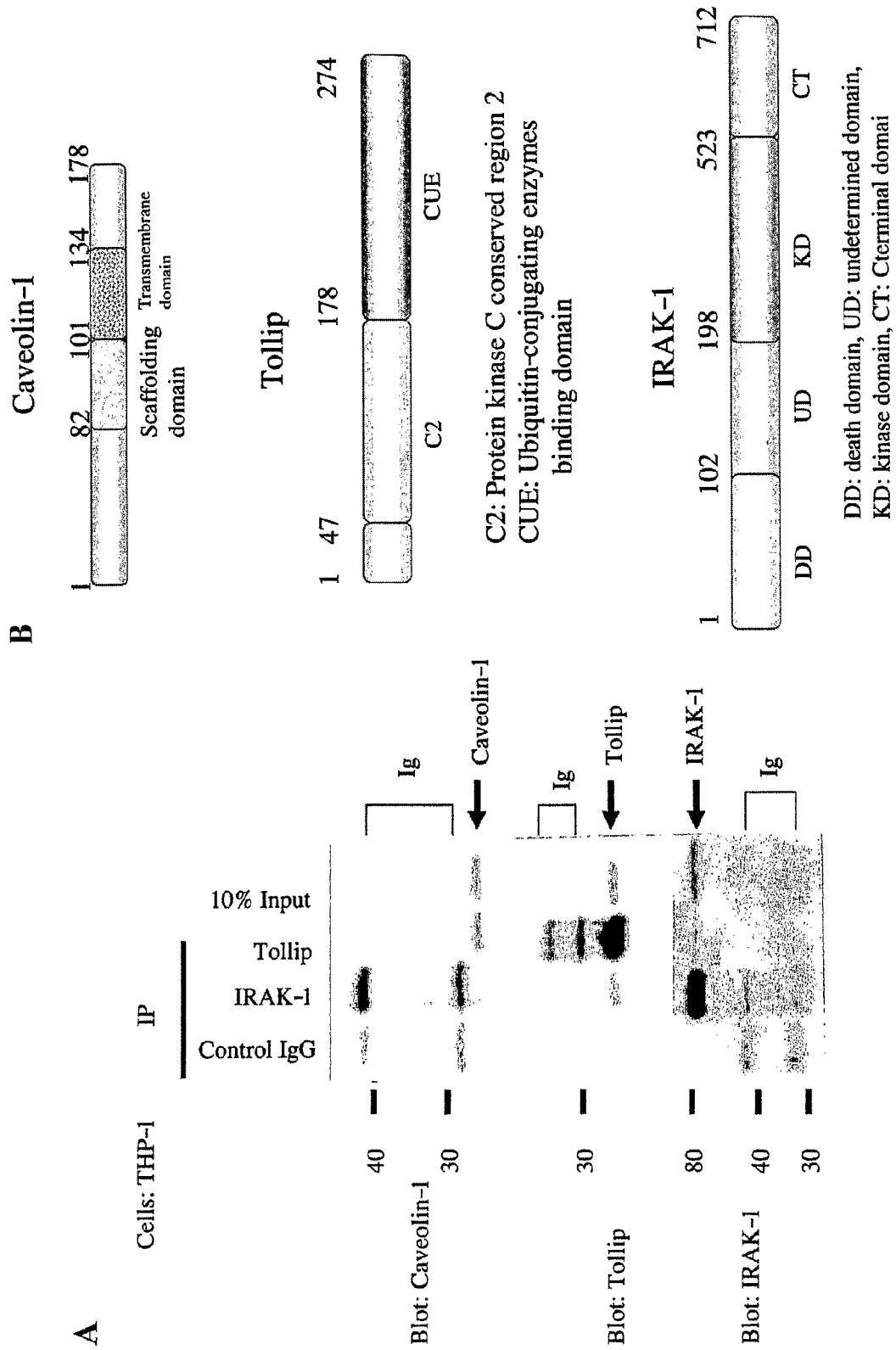
FIG. 7A presents photographs showing endogenous caveolin-1, Tollip, and IRAK-1 immunoprecipitated with a Tollip specific or IRAK-1 specific antibody.
FIG. 7B schematically shows the domain structures of caveolin-1, Tollip, and IRAK-1.
FIG. 7C presents photographs showing immuoblotting of Flag-tagged wild type Tollip and its deletion mutants, which were coexpressed with HA-tagged caveolin-1 and VSV-tagged IRAK-1, with the respective tag-specific antibodies.
FIG. 7D presents photographs showing immunoblotting of HA-tagged caveolin-1, Flag-tagged Tollip, VSV-tagged IRAK-1, and their deletion mutants, with the respective tag-specific antibodies.
Figure 7:
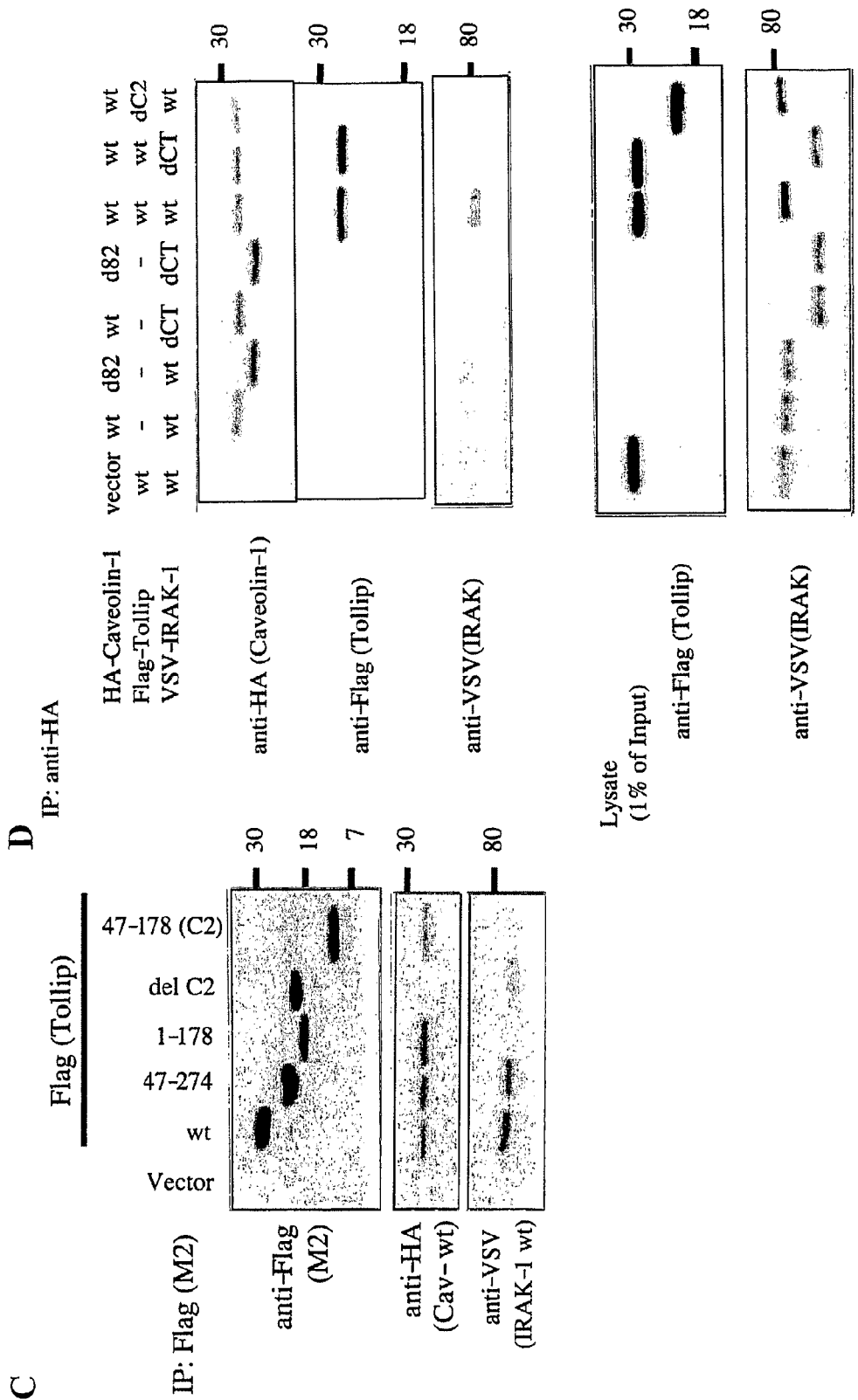

To confirm the association among endogenous caveolin-1, Tollip, and IRAK-1 in living cells, lysates of THP-1 cells were immunoprecipitated (IP) with an IRAK-1 specific antibody and a Tollip specific antibody. After SDS-PAGE, Caveolin-1 was detected by Western blotting (FIG. 7A). Tollip was also detected by its specific antibody in the immunoprecipitates with the IRAK-1 specific antibody (FIG. 7A), while IRAK-1 was detected by its specific antibody in the immunoprecipitates with the Tollip specific antibody (FIG. 7A). These results indicate that caveolin-1 and Tollip are complexed with IRAK-1 to form a triad.

Binding between Tollip and IRAK-1 has already been reported. The CUE domain of Tollip binds the CT domain of IRAK-1, and Tollip inhibits IRAK-1 phosphorylation. In other words, Tollip can be said to function as a negative regulator for IRAK-1. Furthermore, as shown in Example 5 above, Caveolin-1 scaffolding domain binds the Tollip C2 domain. Thus, to determine the binding domains of a complex among caveolin-1, Tollip, and IRAK-1 (FIG. 7B), the following experiments were carried out.

A full-length Tollip (wt) and deletion mutants (47-274, 1-178, delC2, 47-178 (C2)) were tagged with FLAG. In addition, a full-length caveolin-1 and a full-length IRAK-1 were tagged with HA (cav wt-HA) and VSV (IRAK-1 wt-VSV), respectively. These proteins were coexpressed in COS cells. Cell lysates were immunoprecipitated with anti-Flag antibody M2 agarose beads and were submitted to SDS-PAGE and Western blotting with anti-Flag antibody (Tollip), anti-HA tag antibody (caveolin-1) or anti-VSV tag antibody (IRAK-1). Caveolin-1 was not coprecipitated with delC2 Tollip mutant (FIG. 7C). IRAK-1 was not coprecipitated with either of 1-178 or 47-178 (C2) Tollip mutant, however, was coprecipitated with delC2 Tollip mutant. These results suggest that the possibility that the triad forms from the binding of the Tollip C2 domain to caveolin-1 and the Tollip CUE domain to IRAK-1.

Since it is also possible that caveolin-1 and IRAK-1 bind directly, the following experiments were performed. HA-tagged full-length caveolin-1 (HA-cav-wt), and HA-cav-d82 in which the scaffolding domain is deleted, were constructed. Also constructed were FLAG-tagged full-length Tollip (FLAG-Tollip-wt), and FLAG-Tollip-dC2 in which the C2 domain is deleted; and a VSV-tagged full-length IRAK-1 (VSV-IRAK-wt), and VSV-IRAK-dCT in which the CT domain is deleted. These proteins were coexpressed in COS cells and cell lysates were immunoprecipitated as described above. The results are shown in FIG. 7F. Tollip and IRAK both co-precipitated when all full-lengths were expressed. Tollip co-precipitated when IRAK-dCT was expressed, but IRAK did not. Neither Tollip nor IRAK-1 co-precipitated when Tollip-dC2 was expressed. Thus, it was strongly indicated that caveolin-1 and IRAK do not bind directly, and that the Tollip C2 domain binds caveolin-1, and the CUE domain binds IRAK-1.

Example 8 siRNA Against Tollip in Monocytes Attenuates TT-loaded T Cell Proliferation Induced by CD26

Figure 8:
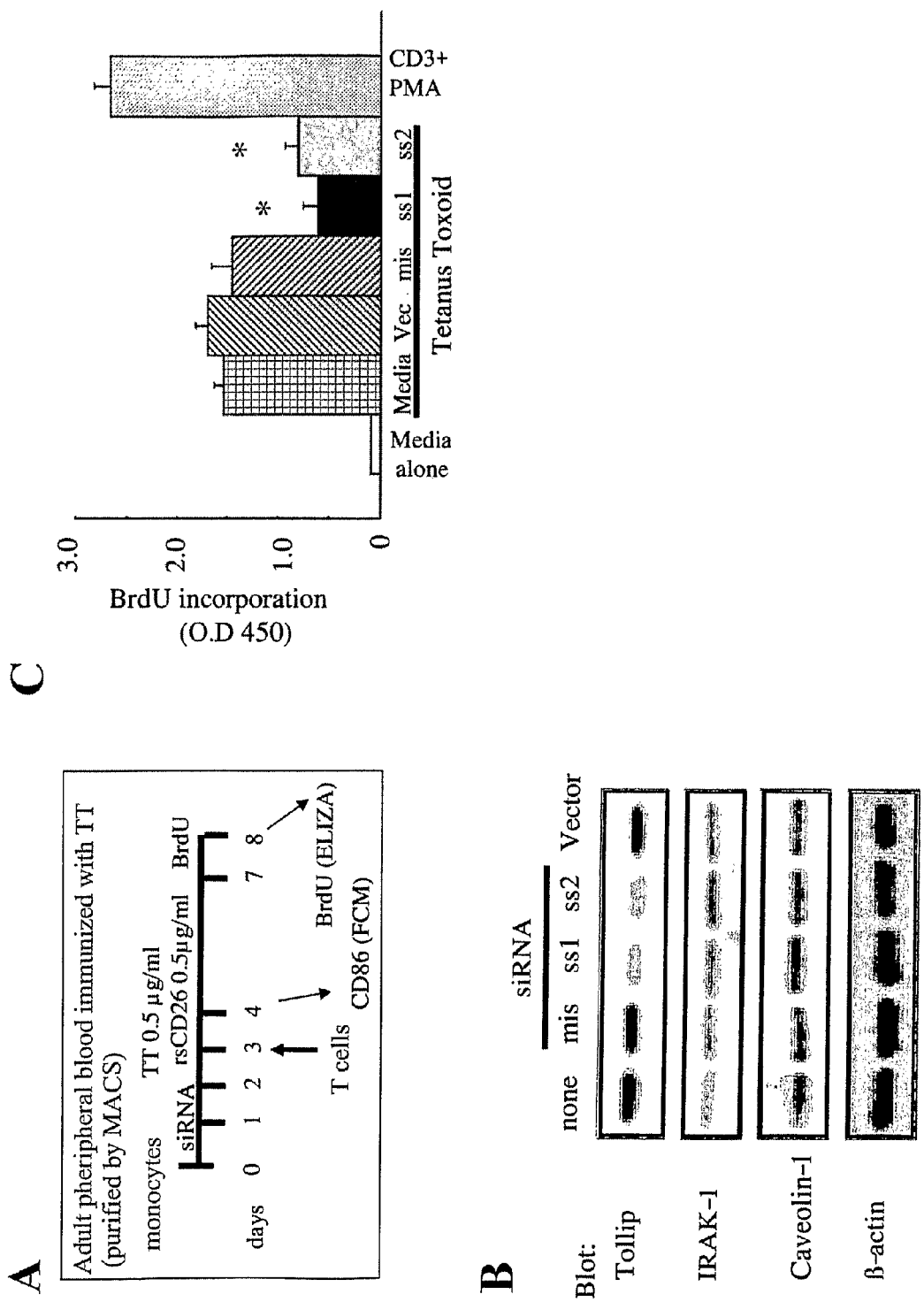
FIG. 8A shows the time table of the experiments of Example 8.
FIG. 8B presents photographs showing immunoblotting of lysates of cells in which Tollip has been knocked down by siRNAs against Tollip, with anti-Tollip antibody, anti-caveolin-1 antibody, and anti-IRAK-1 antibody, followed by stripping and reprobing with anti-β-actin antibody.
FIG. 8C presents bar graphs showing BrdU incorporation in T cells when incubated with monocytes transfected with siRNAs against Tollip.
Figure 9:
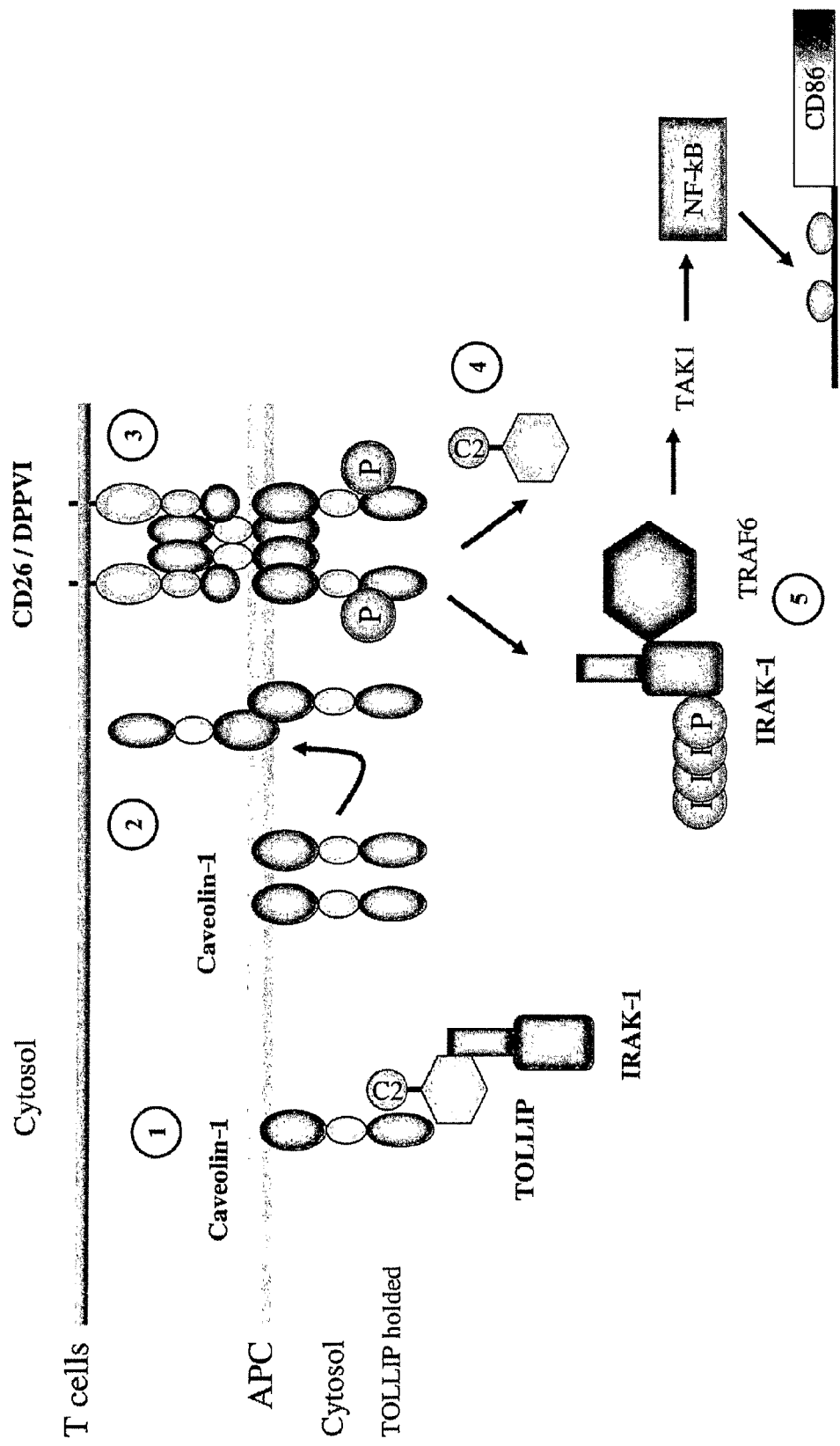
FIG. 9 shows a model for CD26 signaling pathway. (1) Caveolin-1 forms a triad with Tollip and IRAK-1 in APCs (2) After uptake of an antigen, caveolin-1 is exposed on the outer cell surface of the antigen-loaded APCs. (3) CD26 on activated T cells associated with caveolin-1 on the antigen-loaded APCs. Caveolin-1 molecules are aggregated in contact area, followed by its phosphorylation. (4) Phosphorylated caveolin-1 releases Tollip and IRAK-1, presumably due to conformational changes. (5) After IRAK is phosphorylated, it may interact with TRAF6 (TNF receptor-associated factor 6), leading to an activation of NF-κB through TAK1. The activation of NF-κB then leads to the upregulation of CD86.

To examine a role of Tollip in a signal transduction through CD26-caveolin-1 interaction, T cell proliferation assay was performed following the procedure shown in FIG. 8A. Western blot analysis showed that both of the siRNAs specifically knocked down the expression of endogenous Tollip (FIG. 8B). When monocytes were stimulated with tetanus toxoid (TT) and rsCD26, only Tollip knocked down cells inhibited T cell proliferation (FIG. 8C). These results suggest that Tollip plays an important role as a positive regulator in a signal transduction through CD26-caveolin-1 interaction.

From the above results, Tollip may recruit IRAK-1 to caveolin-1 and release IRAK-1 following stimulation with CD26, bringing about CD86, upregulation. When Tollip is reduced, recruitment of IRAK-1 to caveolin-1 may also be reduced, and thus signal transduction induced by CD26 may be reduced.

INDUSTRIAL APPLICABILITY

The present invention involves the discovery that CD26-caveolin-1 interaction plays a role in the upregulation of CD86 on antigen-loaded monocytes and subsequent engagement with CD28 on T cells, leading to antigen-specific T cell activation. CD86 upregulation resulted in potent T cell-APC interaction, leading to the development of activated memory T cells locally and activation of the immune response, and the consequence of various inflammatory diseases. The present invention provides a new approach to the treatment of autoimmune diseases or other immune-mediated disorders by directly interfering with activated memory T cell and APC interaction. Moreover, targeting the interaction of the pocket structure of CD26 and the scaffolding domain of caveolin-1, the interaction between the scaffolding domain of caveolin-1 and the C2 domain of Tollip, and/or the interaction between the CUE domain of Tollip and the CT domain of IRAK-1, may lead to novel therapeutic approaches utilizing agonists or antagonists regulating antigen-specific immune response in not only immune-mediated disorders, but also cancer immunotherapy and viral vaccination as strategies to enhance an immune response.

REFERENCES

Azuma, M., Ito, D., Yagita, H., Okumura, K., Phillips, J. H., Lanier, L. L., and Somoza, C. (1993). B70 antigen is a second ligand for CTLA-4 and CD28. Nature 366, 76-79.

Berberish, I., Shu, G. L., and Clark, E. A. 1994. Cross-linking CD40 on B cells rapidly activates nuclear factor-κB. J Immunol. 153, 4357-4366.

Bucci, M., Gratton, J. P., Rudic, R. D., Acevedo, L., Roviezzo, F., Cirino, G., and Sessa, W. C. (2000). In vivo delivery of the caveolin-1 scaffolding domain inhibits nitric oxide synthesis and reduces inflammation. Nature Med. 6, 1362-1367.

Burns, K., Clatworthy, J., Martin, L., Martinon, F., Plumpton, C., Maschera, B., Lewis, A., Ray, K., Tschopp, J., and Volpe, F. (2000). Tollip, a new component of the IL-1RI pathway, links IRAK to the IL-1 receptor. Nature Cell Biol. 2, 346-351.

Cao, Z., Henzel, W. J., and Gao, X. (1996). IRAK: a kinase associated with interleukin-1 receptor. Science 271, 1128-1131.

Carver, L. A., and Schnitzer, J. E. (2003). Caveolae. Mining little caves for new cancer target. Nature Rev. Cancer. 3, 571-581.

Caux, C., Vanbervliet, B., Massacrier, C., Azuma, M., Okumura, K., Lanier, L. L., and Banchereau, J. (1994). B70/B7-2 is identical to CD86 and is the major functional ligand for CD28 expressed on human dendritic cells. J. Exp. Med. 180, 1841-1847.

Chambers, C. A. (2001). The expanding world of co-stimulation: the two-signal model revisited. Trends Immunol. 22, 217-223.

Croft, M., Duncan, D. D., and Swain, L. S. (1992). Response of naive antigen-specific CD4+ T cells in vitro: characteristics and antigen-presenting cell requirements. J. Exp. Med. 176, 1431-1437.

Drab, M., Verkade, P., Elger, M., Kasper, M., Lohn, M., Lauterbach, B., Menne, J., Lindschau, C., Mende, F., Luft, F. C., Schedl, A., Haller, H., and Kurzchalia, T. V. (2001). Loss of caveolae, vascular dysfunction, and pulmonary defects in caveolin-1 gene-disrupted mice. Science 293, 2449-5242.

Eguchi, K., Ueki, Y, Shimomura, C., Otsubo, T., Nakao, H., Migita, K., Kawakami, A., Matsunaga, M., Tezuka, H., Ishikawa, N., and Nagatuki, S. (1989). Increment in the Ta1+ cells in the peripheral blood and thyroid tissue of patients with Graves' disease. J. Immunol. 142, 4233-4240.

Elbashir, S. M., Harborth, J., Lendeckel, W., Yalcin, A., Weber, C., and Tuschl, T. (2001). Duplexes of 21-nucleotide RNAs mediate RNA interference in cultured mammalian cells. Nature 411, 494-498.

Fleischer, B. (1994). CD26: surface protease involved in T-cell activation. Immunol. Today 15, 180-184.

Fraser, J. D., and Weiss, A. (1992). Regulation of T-cell lymphokine gene transcription by the accessory molecule CD28. Mol Cell Biol. 12, 4357-4363.

Freeman, G. J., Gribben, J. G., Bousiotis, V. A., Ng, J. W., Restivo, V. A., Lombard, L. A., Gray, G. S., and Nadler, L. M. (1993). Cloning of B7-2: a CTLA-4 counter-receptor that costimulates human T cell proliferation. Science 262, 909-911.

Galbiati, F., Razani, B., and Lisanti, M. P. (2001). Emerging themes in lipid rafts and caveolae. Cell 106, 403-411.

Gordon, S. (2002). Alternative activation of macrophages. Nature Rev. Immunol. 3, 23-35.

Grakoui, A., Bromley, S. K., Sumen, C., Davis, M. M., Shaw, A. S., Allen, P. M., Dustin, M. L. (1999). The immunological synapse: a molecular machine controlling T cell activation. Science 285, 221-227.

Hafler, D. A., Fox, D. A., Manning, M. E., Schlossman, S. F., Reinherz, E. L., and Weiner, H. L. (1985). In vivo activated T lymphocytes in the peripheral blood and cerebrospinal fluid of patients with multiple sclerosis. N. Engl. J. Med. 312, 1405-1411.

Hakamada-Taguchi, R., Kato, T., Ushijima, H., Murakami, M., Uede, T., and Nariuchi, H. (1998). Expression and co-stimulatory function of B7-2 on murine CD4+ T cells. Eur. J. Immunol. 28, 865 873.

Hathcock, K. S., Laszlo, G., Pucillo, C., Linsley, P., and Hodes, R. J. (1994). Comparative analysis of B7-1 and B7-2 costimulatory ligands: expression and function. J. Exp. Med. 180, 631-640.

Hegen, M., Kameoka, J., Dong, R-P., Schlossman, S. F., and Morimoto, C. (1997). Cross-linking of CD26 by antibody induces tyrosine phosphorylation and activation of mitogen-activated protein kinase. Immunology 90, 257-264.

Huppa, J. B., Gleimer, M., Sumen, C., and Davis, M. M. (2003). Continuous T cell receptor signaling required for synapse maintenance and full effector potential. Nature Immunol. 4, 749-755.

Ikushima, H., Munakata, Y, Ishii, T., Iwata, S., Terashima, M., Tanaka, H., Schlossman, S. F., and Morimoto, C. (2000). Internalization of CD26 by mannose 6-phosphate/insulin-like growth factor II receptor contributes to T cell activation. Proc. Natl. Acad. Sci. USA. 97, 8439-8444.

Iwata, S., Yamaguchi, N., Munakata, Y., Ikushima, H., Lee, J. F., Hosono, O., Schlossman, S. F., and Morimoto, C. (1999). CD26/dipeptidyl peptidase IV differentially regulates the chemotaxis of T cells and monocytes toward RANTES: possible mechanism for the switch from innate to acquired immune response. Int. Immunol. 11, 417-426.

Kameoka, J. Tanaka, T., Nojima, Y., Schlossman, S. F., and Morimoto, C. (1993). Direct association of adenosine deaminase with a T cell activation antigen, CD26. Science 261, 466-469.

Krummel, M. F., and Allison, J. P. (1995). CD28 and CTLA-4 have opposing effects on the response of T cells to stimulation. J. Exp. Med. 182, 459-465, 1995.

Lee K. H., Holdorf, A. D., Dustin, M. L., Chan, A. C., Allen, P. M., and Shaw, A. S. (2002). T cell receptor signaling precedes immunological synapse formation. Science 295, 1539-1542.

Lenschow, D. J., Walunas, T. L., and Bluestone, J. A. (1996). CD28/B7 system of T cell costimulation. Annu. Rev. Immunol. 14, 233-258.

Li, J., Liu, Z., Jiangu, S., Cortesini, R., Lederman, S., and Suciu-Foca, N. (1999). T suppressor lymphocytes inhibit NF-□B-mediated transcription of CD86 gene in APC. J. Immunol. 163, 6386-6392.

Makino, Y., Okamoto, K., Yoshikawa, N., Aoshima, M., Hirota, K., Yodoi, J., Umesono, K., Makino, I., and Tanaka, H. (1996). Thioredoxin: a Redox-regulating Cellular Cofactor for Glucocorticoid Hormone Action Cross Talk between Endocrine Control of Stress Response and Cellular Antioxidant Defense System. J. Clin. Invest. 98, 2469-2477.

Manickasingham, S. P., Anderson, S. M., Burkhart, C., and Wraith, D. C. (1998). Qualitative and quantitative effects of CD28/B7-mediated costimulation on naive T cells in vivo. J. Immunol. 161, 3827-3835.

McAdam, A. J., Schweitzer, A. N., and Sharpe, A. H. (1998). The role of B7 co-stimulation in activation and differentiation of CD4+ and CD8+ T cells. Immunol. Rev. 165, 231-247.

Medzihitov, R. (2001). Toll-like receptors and innate immunity. Nature Rev. Immunol. 1, 135-145.

Mizokami, A., Eguchi, K., Kawakami, A., Ida, H., Kawabe, Y., Tsukada, T., Aoyagi, T., Maeda, K., Morimoto, C., and Nagataki, S. (1996). Increased population of high fluorescence 1F7 (CD26) antigen on T cells in synovial fluid of patients with rheumatoid arthritis. J. Rheumatol. 23, 2022-2026.

Montesano, R., Roth, J., Robert, A., and Orchi, L. (1982). Non-coated membrane invaginations are involved in binding and internalization of cholera and tetanus toxins. Nature 296, 651-653.

Morimoto, C., Torimoto, Y., Levinson, G., Rudd, C. E., Schrieber, M., Dang, N. H., Letvin, N. L., and Schlossman, S. F. (1989). 1F7, a novel cell surface molecule involved in helper function of CD4 cells. J. Immunol. 143, 3430-3439.

Morimoto, C., and Schlossman, S. F. (1998). The structure and function of CD26 in the T-cell immune response. Immunol. Rev. 161, 55-70.

Ohnuma, K., Munakata, Y., Ishii, T., Iwata, S., Kobayashi, S., Hosono, O., Kawasaki, H., Dang, N. H., and Morimoto, C. (2001). Soluble CD26/dipeptidyl peptidase IV induces T cell proliferation through CD86 up-regulation on APCs. J. Immunol. 167, 6745-6755.

Oravecz, T., Pall, M., Roderiquez, G., Gorrell, M. D., Ditto M., Nguyen, N. Y., Boykins, R., Unsworth, E., and Norcross, M. A. (1997). Regulation of the receptor specificity and function of the chemokine RANTES (Regulated on Activation, Normal T cells Expressed and Secreted) by dipeptidyl peptidase IV (CD26)-mediated cleavage. J. Exp. Med. 186, 1865-1872.

Peiro, S., Comella, J. X., Enrich, C., Martin-Zanca, D., and Rocamora, N. (2000). PC12 cells have caveolae that contain TrkA, Caveolae-disrupting drugs inhibit nerve growth factor-induced, but not epidermal growth factor-induced, MAPK phosphorylation. J. Biol. Chem. 275, 37846-37852.

Pelknans, L., and Helenius, A. (2002). Endocytosis via caveolae. Traffic 3, 311-20.

Rasmussen, H. B., Branner, S., Wiberg, F. C., and Wagtoman, N. (2003). Crystal structure of human dipeptidyl peptidase IV/CD26 in complex with a substrate analog. Nature Struct. Biol. 10, 19-25.

Riemann, D., Hansen, G. H., Niels-Christiansen, L. L., Thorsen, E., Immerdal, L., Santos, A. N., Kehlen, A., Langner, J., and Danielsen, E. M. (2001). Caveolae/lipid rafts in fibroblast-like synoviocytes: ectopeptidase-rich membrane microdomains. Biochem. J. 354, 47-55.

Sanchez, I., Hughes, R. T., Mayer, B. J., Yee, K., Woodgett, J. R., Avruch, J., Kyriakis, J. M., and Zon, L. I. (1994). Role of SAPK/ERK kinase-1 in the stress-activated pathway regulating transcription factor c-Jun. Nature 372, 794-798.

Smart, E. J., Graf, G. A., McNiven, M. A., Sessa, W. C., Engleman, J. A., Sherper, P. E., Okamoto, T., and Lisanti, M. P. (1999). Caveolins, liquid-ordered domains, and signal transduction. Mol. Cell. Biol. 19, 7289-7304.

Tanaka, T., Camerini, D., Seed, B., Torimoto, Y, Dang, N. H., Kameoka, J., Dahlberg, H. N., Schlossman, S. F., and Morimoto, C. (1992). Cloning and functional expression of the T cell activation antigen CD26. J. Immunol. 149, 481-486.

Tanaka, T., Kameoka, J., Yaron, A., Schlossman, S. F., and Morimoto, C. (1993). The costimulatory activity of the CD26 antigen requires dipeptidyl peptidase IV enzymatic activity. Proc. Natl. Acad. Sci. USA. 90, 4583-4590.

Tanaka, T., Duke-Cohan, J. S., Kameoka, J., Yaron, A., Lee, I., Schlossman, S. F., and Morimoto, C. (1994). Enhancement of antigen-induced T-cell proliferation by soluble CD26/dipeptidyl peptidase IV. Proc. Natl. Acad. Sci. USA. 91, 3082-3086.

Tanaka, J., Miwa, Y., Miyoshi, K., Ueno, A., and Inoue, H. (1999). Construction of Epstein-Barr virus-based expression vector containing MiniOriP. Biochem. Biophy. Res. Com. 264, 938-943.

Turley, S. J., Inaba, K., Garrett, W. S., Ebersold, M., Unternaehrer, J., Steinman, R. M., and Mellman, I. (2000). Transport of peptide-MHC class II complexes in developing dendritic cells. Science 288, 522-527.

von Bonin, A., Huhn, J., and Fleischer, B. (1998). Dipeptidyl-peptidase IV/CD26 on T cells: analysis of an alternative T-cell activation pathway. Immunol. Rev. 161, 43-53.

Walunas, T. L., Lenschow, D. J., Bakker, C. Y., Linsley, P. S., Freeman, G. J., Green, J. M., Thompson, C. B., and Bluestone, J. A. (1994). CTLA-4 can function as a negative regulator of T cell activation. Immunity 1: 4405-413.

Yasukawa, T., Kanei-Ishii, C., Maekawa, T., Fujimoto, J., Yamamoto, T., and Ishii, S. (1995). Increase of solubility of foreign proteins in *Escherichia Coli* by coproduction of the bacterial thioredoxin. J. Biol. Chem. 270, 25328-25331.

Yi-qun, Z., Joost van Neerven, R. J., Kasran, A., de Boer, M., and Ceuppens, J. L. (1996). Differential requirements for co-stimulatory signals from B7 family members by resting versus and recently activated memory T cells towards soluble recall antigens Int. Immunol. 8, 37-44.

Yokochi, T., Holly, R. D., and Clark, E. A. (1982). B lymphoblast antigen (BB-1) expressed on Epstein-Barr virus-activated B cell blasts, B lymphoblastoid cell lines, and Burkitt's lymphomas. J. Immunol. 128, 823-827.

Zhang, G., and Ghosh, S. (2002). Negative regulation of Toll-like receptor-mediated signaling by Tollip. J. Biol. Chem. 277, 7059-7065.

The invention claimed is:

1. A method for identifying a substance that down-regulates an immune response in an animal, comprising determining whether said substance inhibits an interaction between factors in the CD26 signaling pathway, wherein said substance inhibits the interaction between CD26 and caveolin-1.

2. The method of claim 1, wherein said interaction is protein:protein binding.

3. The method of claim 1, wherein said interaction is determined by one or more assay(s) selected from the group consisting of immunoprecipitation, Western blotting, affinity chromatography, fluorescence microscopy, and two hybrid assay.

4. The method of claim 1, comprising contacting cells or extracts from cells with said substance.

5. The method of claim 4, wherein said cells are T cells or monocytes.

6. The method of claim 4, wherein said cells recombinantly express a factor in the CD26 signaling pathway.

7. The method of claim 4, wherein said cells comprise a reporter gene the expression of which is responsive to a factor in the CD26 signaling pathway.

8. The method of claim 1, wherein said substance is part of a library of substances.

9. A kit for identifying a substance that down-regulates an immune response in an animal, comprising at least one agent for determining whether a substance inhibits the interaction between CD26 and caveolin-1.

* * * * *